United States Patent
Wang et al.

(10) Patent No.: US 10,151,720 B2
(45) Date of Patent: Dec. 11, 2018

(54) INTERFACIAL NANOFIBRIL COMPOSITE FOR SELECTIVE ALKANE VAPOR DETECTION

(71) Applicant: University of Utah Research Foundation, Salt Lake City, UT (US)

(72) Inventors: Chen Wang, Salt Lake City, UT (US); Ling Zang, Salt Lake City, UT (US); Benjamin Bunes, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 210 days.

(21) Appl. No.: 15/342,957

(22) Filed: Nov. 3, 2016

(65) Prior Publication Data
US 2017/0122893 A1    May 4, 2017

Related U.S. Application Data

(60) Provisional application No. 62/285,628, filed on Nov. 3, 2015, provisional application No. 62/403,478, filed on Oct. 3, 2016.

(51) Int. Cl.
*G01N 27/12* (2006.01)
*G01N 33/00* (2006.01)

(52) U.S. Cl.
CPC ......... *G01N 27/128* (2013.01); *G01N 27/126* (2013.01); *G01N 27/127* (2013.01); *G01N 33/0031* (2013.01); *G01N 33/0057* (2013.01)

(58) Field of Classification Search
None
See application file for complete search history.

(56) References Cited

U.S. PATENT DOCUMENTS

| | | |
|---|---|---|
| 5,571,401 A | 11/1996 | Lewis et al. |
| 8,105,538 B2 | 1/2012 | Ramamurthy et al. |
| 8,178,157 B2 | 5/2012 | Wei et al. |
| 8,486,708 B2 | 7/2013 | Zang et al. |
| 8,573,030 B2 | 11/2013 | Gole |
| 8,809,063 B2 | 8/2014 | Zang et al. |
| 8,889,420 B2 | 11/2014 | Zang et al. |
| 9,212,055 B2 | 12/2015 | Zhou et al. |
| 9,291,586 B2 | 3/2016 | Neikirk et al. |
| 2007/0120095 A1 | 5/2007 | Gruner |

(Continued)

FOREIGN PATENT DOCUMENTS

WO    WO 2016/029003 A1    2/2016

OTHER PUBLICATIONS

Addabbo et al, "Gas Sensing Properties and Modeling of $YCoO_3$ Based Perovskite Materials." Sensors and Actuators B; Elsevier; Dec. 31, 2015; vol. 221; pp. 1137-1155.

(Continued)

*Primary Examiner* — Xiaoyun R Xu
(74) *Attorney, Agent, or Firm* — Thorpe North & Western, LLP

(57) ABSTRACT

A nanofiber composite sensor for detecting alkanes can include a network of contacting nanofibers having multiple contact points. Each contact point can form an interfiber interface of interdigitated alkyl chains. Alkanes can be adsorbed at the interfiber interface which results in an increased interfiber distance between first and second nanofibers and a decreased charge transfer efficiency. The detected alkanes can be in a vapor or liquid phase.

22 Claims, 41 Drawing Sheets

(56) References Cited

U.S. PATENT DOCUMENTS

| | | |
|---|---|---|
| 2009/0233374 A1 | 9/2009 | Zang et al. |
| 2012/0108465 A1 | 5/2012 | Duoss et al. |
| 2013/0183766 A1 | 7/2013 | Zang et al. |
| 2014/0223997 A1 | 8/2014 | Gole |
| 2014/0235493 A1 | 8/2014 | Zang et al. |
| 2015/0123073 A1 | 5/2015 | Lei et al. |

OTHER PUBLICATIONS

Allen et al, "Carbon Nanotube Field-Effect-Transistor-Based Biosensors." Advanced Materials; Wiley; Apr. 30, 2007; vol. 19 Issue 11; pp. 1439-1451.

Bunes et al, "Photodoping and Enhanced Visible Light Absorption in Single-Walled Carbon Nanotubes Functionalized With a Wide Band Gap Oligomer." Advanced Materials; Material Views; Jan. 2015; vol. 27 Issue 1; pp. 162-167.

Che et al, "Interfacial Engineering of Organic Nanofibril Heterojunctions Into Highly Photoconductive Materials." Journal of the Chemical Society; American Chemical Society; Dec. 23, 2010; vol. 133 Issue 4; pp. 1087-1091.

Chen et al, "Enhancement of Visible-Light-Driven Photocatalytic $H_2$ Evolution From Water Over g-$C_3N_4$ Through Combination With Perylene Diimide Aggregates." Applied Catalysis A: General; Elsevier; Jun. 5, 2015; vol. 498; pp. 63-68.

Clarke et al, "Charge Photogeneration in Organic Solar Cells." Chemical Reviews; American Chemical Society; Jan. 11, 2010; vol. 110 Issue 11; pp. 6736-6767.

Giberti et al, "Tin (IV) Sulfide Nanorods as a New Gas Sensing Material." Sensors and Acutators B; Elsevier; Feb. 2016; vol. 223; pp. 827-833.

Holcombe et al, "Steric Control of the Donor/Acceptor Interface: Implications in Organic Photovoltaic Charge Generation." Journal of the American Chemical Society; American Chemical Society; Jun. 20, 2011; pp. 12106-12114.

Huang et al, "Morphology Control of Nanofibril Donor-Acceptor Heterojunction to Achieve High Photoconductivity: Exploration of the New Molecular Design Rule." Journal of the American Chemical Society; American Chemical Society; Oct. 4, 2013; vol. 135 Issue 44; pp. 16490-16496.

Jang et al, "Carbon Nanofiber/Polypyrrole Nanocable as Toxic Gas Sensor." Sensors and Actuators B; Elsevier; Mar. 8, 2007; vol. 122 Issue 1; pp. 1-13.

Kauffman et al, "Carbon Nanotube Gas and Vapor Sensors." Angewandte Chemie International Edition; Wiley; Jul. 18, 2008; vol. 47 Issue 35; pp. 6550-6570.

Kisner et al, "Probing the Effect of Surface Chemistry on the Electrical Properties of Ultrathin Gold Nanowire Sensors." Nanoscale; Royal Society of Chemistry; Mar. 4, 2014; Issue 10; pp. 5146-5155.

Laminack et al, "Sulfur-$H_z(CH_x)_y$(Z=0,1) Functionalized Metal Oxide Nano structure Decorated Interfaces: Evidence of Lewis Base and Bronsted Acid Sites—Influence on Chemical Sensing." Materials Chemistry and Physics; Elsevier; Jun. 15, 2015; vol. 160; pp. 20-31.

Lopez-Andarias et al, "Highly Ordered n/p-Co-Assembled Materials With Remarkable Charge Mobilities." Journal of the Chemical Society; American Chemical Society; Dec. 21, 2014; vol. 137 Issue 2; pp. 893-897.

Prasanthkumar et al, "Organic Donor-Acceptor Assemblies Form Coaxial p-n Heterojunctions With High Photoconductivity." Angewandte Chemie International Edition; Wiley; Nov. 27, 2014; vol. 54 Issue 3; pp. 946-950.

Ronot et al, "Optimization and Performance of a Specifically Coated Intrinsic Optical-Fibre Sensor for the Detection of Alkane Compounds" Sensors and Actuators A Physical; Elsevier; Apr. 1994; vol. 42 Issues 1-3; pp. 529-534.

Snow et al, "Chemical Vapor Detection Using Single-Walled Carbon Nanotubes." Chemical Society Reviews; Royal Society of Chemistry; May 24, 2006; vol. 35 Issue 9; pp. 790-798.

Wang et al, "Sulfonated Poly(Ether Ether Ketone)/Polypyrrole Core-Shell Nanofibers: A novel Polymeric Adsorbent/Conducting Polymer Nanostructures for Ultrasensitive Gas Sensors." Applied Materials & Interfaces; American Chemical Society; Oct. 22, 2012; vol. 4 Issue 11; pp. 6080-6084.

Wang et al, "Interfacial Donor-Acceptor Nanofibril Composites for Selective Alkane Vapor Detection." ACS Sensors; American Chemical Society; Mar. 9, 2016; vol. 1 Issue 5; pp. 552-559.

Yiu et al, "Side-Chain Tunability of Furan-Containing Low-Band-Gap Polymers Provides Control of Structural Order in Efficient Solar Cells." Journal of American Chemical Society; American Chemical Society; Dec. 22, 2011; vol. 134 Issue 4; pp. 2180-2185.

Zang, "Interfacial Donor-Acceptor Engineering of Nanofiber Materials to Achieve Photoconductivity and Applications." Accounts of Chemical Research; American Chemical Society; Sep. 28, 2015; vol. 48 Issue 10; pp. 2705-2714.

Zeng et al, "Hydrothermal Synthesis, Characterization of h-$WO_3$ Nanowires and the Gas Sensing of Thin Film Sensor Based on this Powder." Thin Solid Films; Elsevier; Jun. 1, 2015; vol. 584; pp. 294-299.

Zhang et al, "Organic Nanofibrils Based on Linear Carbazole Trimer for Explosive Sensing." Chem. Commun. ; The Royal Society of Chemistry; Jun. 24, 2010; vol. 46; pp. 5560-5562.

Zang; "Interfacial Nanofiber Composites for Trace Alkane Detection"; Ustar; (Sep. 16, 2015); 3 pages; [retrieved on Jun. 20, 2017], Retrieved from the internet: <URL: https://ustar.org/interfacial_nanofiber_news>.

International search report dated Sep. 1, 2017, for PCT Application No. PCT/US16/60382, filed Nov. 3, 2016, 4 pages.

INTERFACIAL NANOFIBRIL COMPOSITE FOR SELECTIVE ALKANE VAPOR DETECTION

RELATED APPLICATIONS

This application claims priority to U.S. Provisional Application No. 62/285,628, filed Nov. 3, 2015, and U.S. Provisional Application No. 62/403,478, filed Oct. 3, 2016, each of which is incorporated herein by reference.

GOVERNMENT INTEREST

This invention was made with government support under Grant No. 2009-ST-108-LR0005 awarded by U.S. Department of Homeland Security, Grant No. CHE0931466 awarded by National Science Foundation, and Grant No. NNX12AM67H awarded by NASA. The government has certain rights in the invention.

FIELD OF THE INVENTION

This invention relates to the field of vapor or gas detection using specific nanomaterials. Accordingly, the invention involves the fields of organic chemistry, chemical engineering, and nanotechnology.

BACKGROUND

Alkanes, the most common products from the fossil fuel, are the main components of power oil and a primary source of energy for modern society. They are also important industrial crude materials and solvents. While serving people, the prevalence of alkanes poses a risk to security, environment, and health. Alkanes are flammable and their vapors are extremely explosive when mixed with oxygen. They are also used to make ammonium nitrate/fuel oil (ANFO), a powerful improvised explosive, which is hard to detect. Improper and malicious use of alkanes and their products have brought numerous disasters in recent years, including the Oklahoma City Bombing in 1995. Additionally, according to the Criteria Documents (No. 77-141B) from NIOSH, alkane vapors could lead to toxicity to human nervous and skin system. Such alkane vapors can also be odorless which introduces additional inadvertent exposure risk. Therefore, a reliable, quick, and portable detection method for alkane vapor is necessary for public safety and industrial control. Because of their high volatility, alkanes produce significant vapor, which creates a potential for nondestructive detection by sensors and analytical instruments. However, current technologies still face great challenges on alkane vapor detection, particularly with trace level sensitivity and real-time monitoring. Traditional spectroscopy methods, such as gas chromatography-mass spectrometry (GC-MS) and ion mobility spectroscopy (IMS), are slow, expensive, and complicated to operate. The chemical inertness of alkanes limits the effectiveness of sensing techniques based on direct chemical reactions or interactions, such as electrochemistry, reaction-based fluorescence, and chemiresistors.

SUMMARY

A nanofiber composite sensor for detecting alkanes can comprise of a network of contacting nanofibers having multiple contact points. Each contact point can form an interfiber interface of interdigitated alkyl chains, wherein the alkanes are adsorbed at the interfiber interface to increase an interfiber distance between first and second nanofibers and decrease charge transfer efficiency. The detected alkanes can be in a vapor or liquid phase.

A complimentary method of detecting alkanes can comprise exposing a network of contacting nanofibers having multiple contact points, where the contact points can form an interfiber interface of interdigitated alkyl chains, to a suspected target compound source. The method can further include measuring an electrical response of the network of nanofibers caused by the alkanes adsorbing at the interfiber interface and increasing an interfiber distance between first and second nanofibers which decreases the charge transfer efficiency. The method can further include displaying a detection metric based on the electrical response. In some cases, the first and second nanofibers can be donor nanofibers and acceptor nanofibers, and in other cases the first and second nanofibers can be carbon nanotubes.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

FIG. 6A shows a high magnification image of the ACTC nanofibers. FIG. 6B shows a large area image of the ACTC nanofibers.

FIG. 7C are the PTCDI-$C_6$ nanofibers and FIG. 7D are the ACTC/PTCDI-$C_6$ nanofibril composite; FIG. 7E are images of the PTCDI-PE nanofibers and FIG. 7F are the ACTC/PTCDI-PE nanofibril composite. All scale bars are 50 µm.

(FIG. 11B) (1) ethanol, (2) acetonitrile, (3) tetrahydrofuran, (4) ethyl acetate, (5) dichloromethane, (6) water, (7) acetone, and (8) hexylamine at room temperature.

FIG. 12A is a graph of the relative absorption of the ACTC nanofibers, PTCDI-DD nanofibers, and ACTC/PTCDI-DD composite. FIG. 12B is a graph of the relative absorption of the ACTC nanofibers, PTCDI-$C_6$ nanofibers, and ACTC/PTCDI-$C_6$ composite. FIG. 12C is a graph of the relative absorption of the ACTC nanofibers, PTCDI-PE nanofibers, and ACTC/PTCDI-PE composite. In each case, 2 ml of ethanol was added to 1 mL of the original quasi-uniform mixture of PTCDI nanofibers, ACTC nanofibers, or ACTC/PTCDI 1:1 composites while shaking. The spectra of ACTC/PTCDI composite and ACTC nanofibers were normalized to 1. The highest peaks are located at around 320 nm, indicating the similar stacking mode of the pure ACTC nanofibers and the ACTC/PTCDI composite. The spectra of PTCDI nanofibers were normalized and their maxima peak values were set to the same values as the first peak of the PTCDI in the ACTC/PTCDI composites for ease of comparison.

Figure 19A:
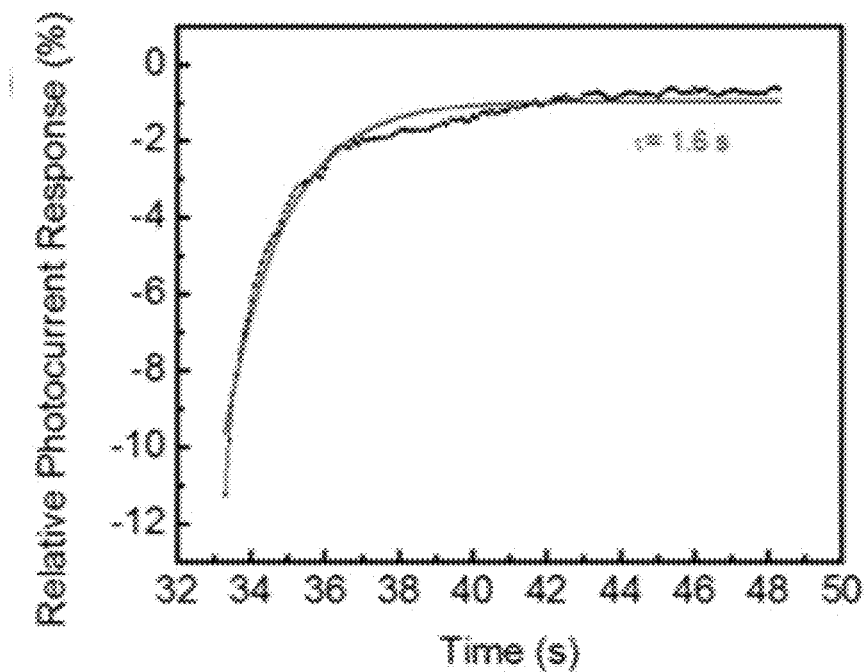
FIG. 19A-19E are graphs showing the kinetics fitting of the photocurrent recovery for alkanes. The fitting equation is relative photocurrent response $$\left(\frac{I_0 - I_t}{I_0} \cdot 100\%\right) = A \cdot \exp\left(-\frac{t - t_0}{\tau}\right) + B,$$
Figure 19B:
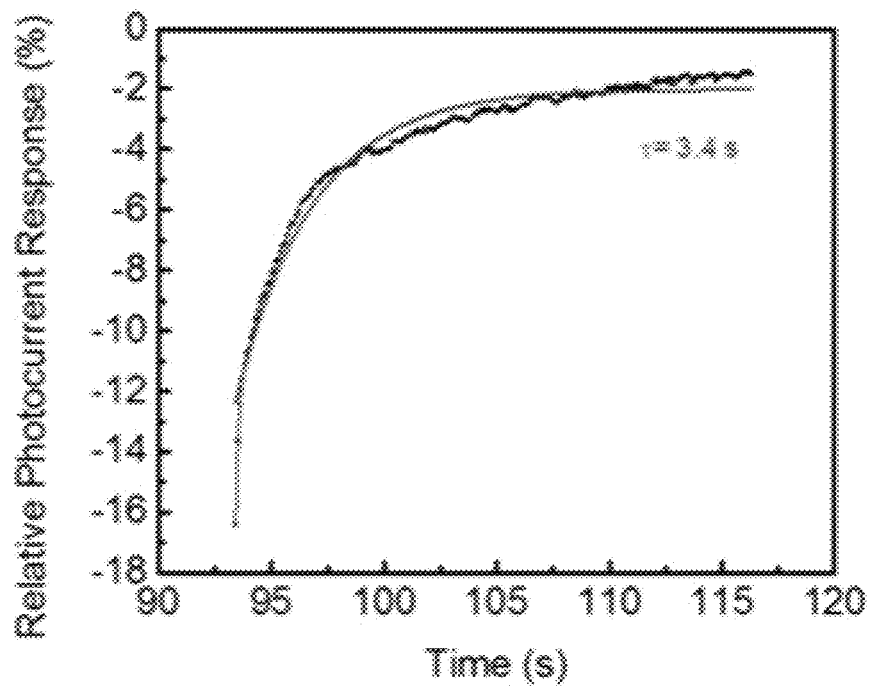
Figure 19C:
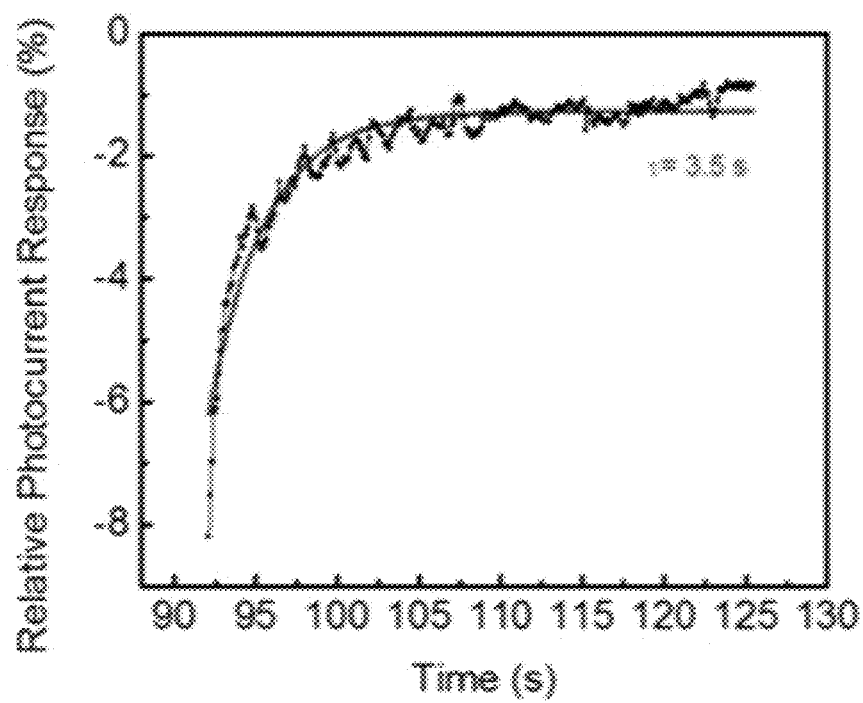
Figure 19D:
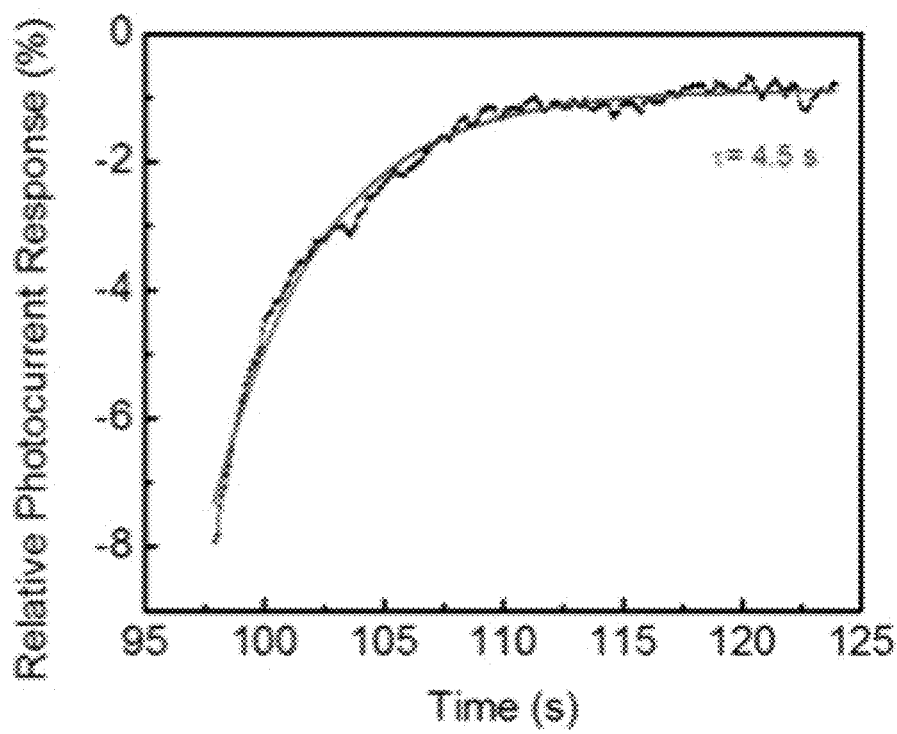
Figure 19E:
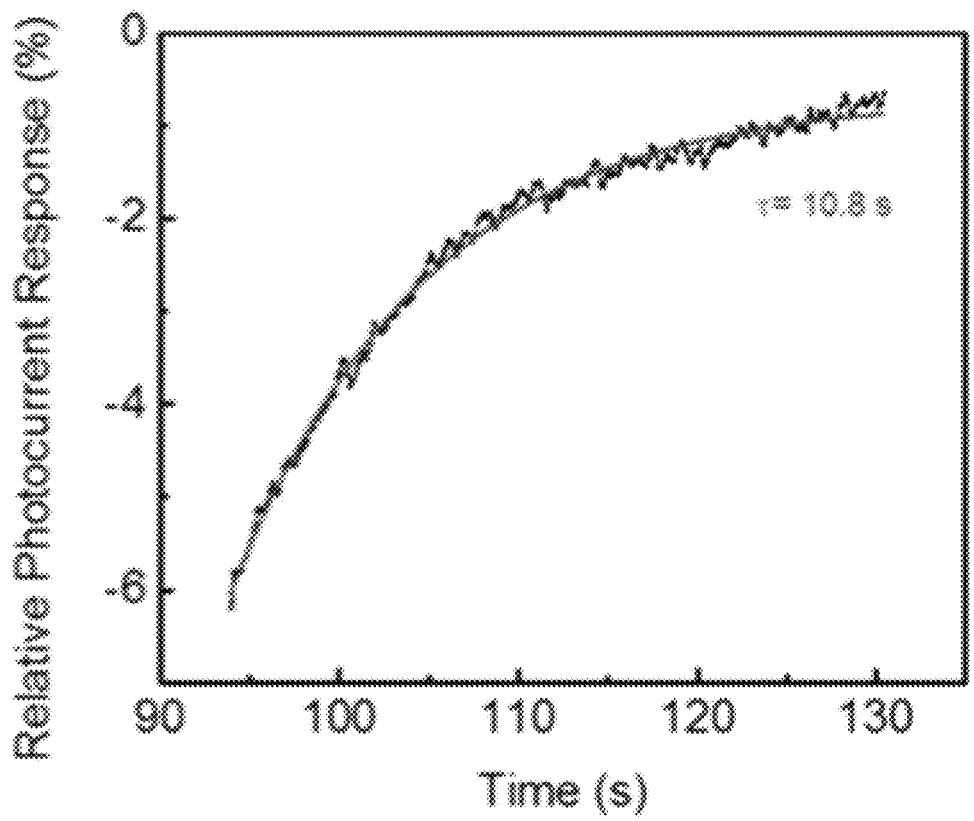

where t represents the elapsed time in the experiment; $t_0$ represents the time when the alkane flow is stopped; $\tau$ represents the recovery time term; A and B represent constants related to the alkane species. The range of the data for fitting is from the termination of the alkane vapor exposure to 90% photocurrent recovery. The photocurrent recovery time fittings for saturated vapor of (FIG. 19A) n-hexane ($C_6H_{14}$), (FIG. 19B) cyclohexane ($C_6H_{12}$), (FIG. 19C) n-octane ($C_8H_{18}$), (FIG. 19D) n-decane ($C_{10}H_{22}$), and (FIG. 19E) n-dodecane ($C_{12}H_{26}$).

Figure 20A:
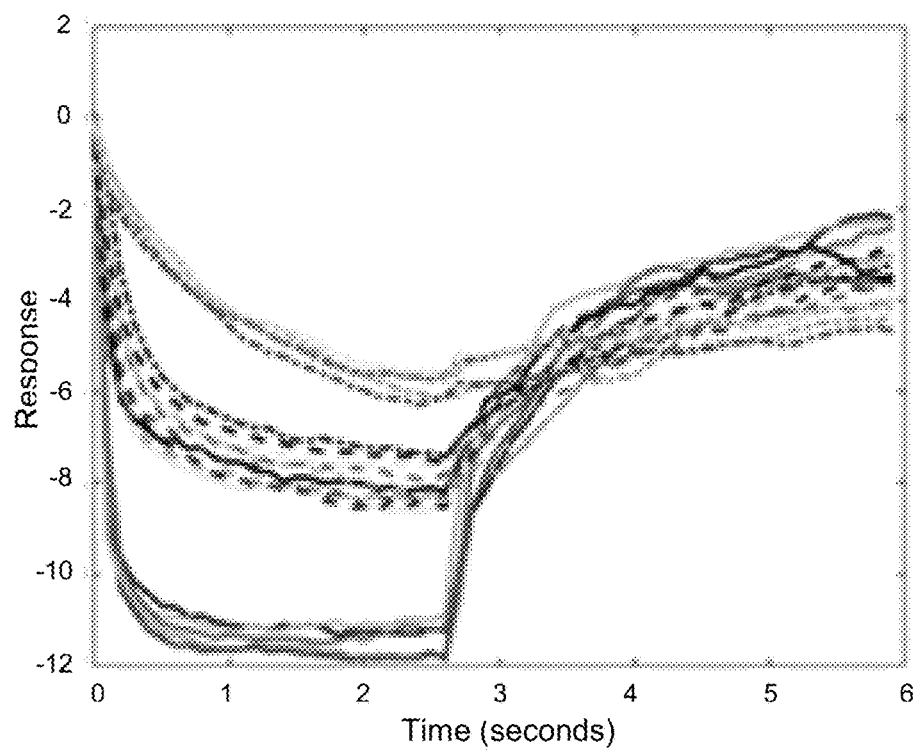
Figure 20B:
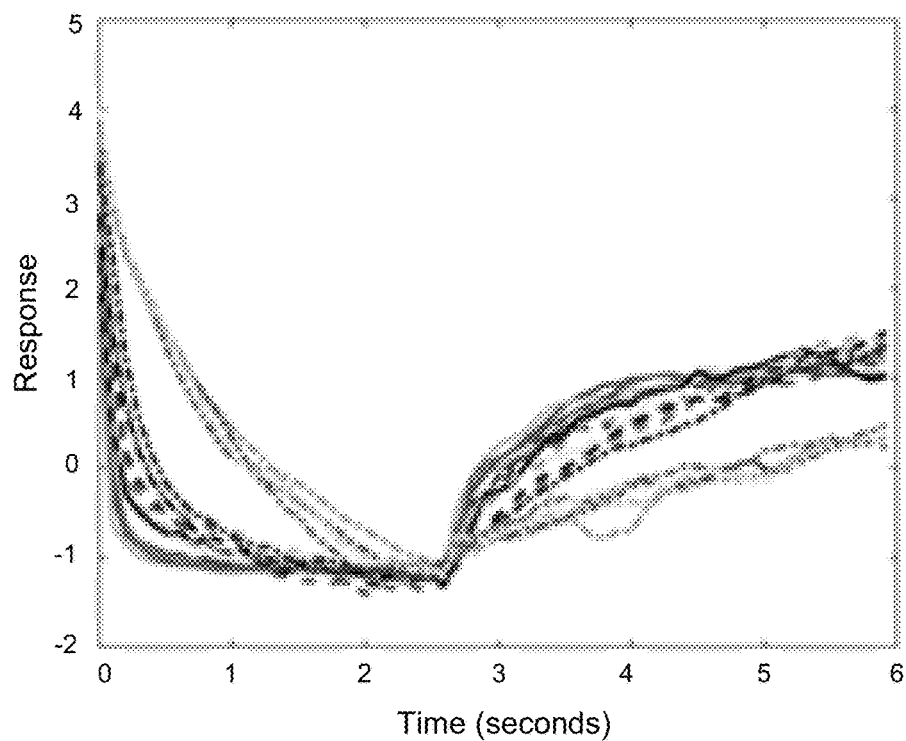

FIG. 20A-20B are graphs showing a processing method in the principle component analysis (PCA). Each exposure (20 in total) were replotted together in FIG. 20A. For each exposure, the data for the first 6 seconds were used for modeling. In FIG. 20B the data were re-scaled prior to analysis, i.e., each response curve was centered on its average value and thereafter scaled to a standard deviation of one. Then PCA was performed using the statistics package in Matlab 2014b for the pretreated data in FIG. 20B and the first two components show clear separation between the different alkanes.

Figure 21A:
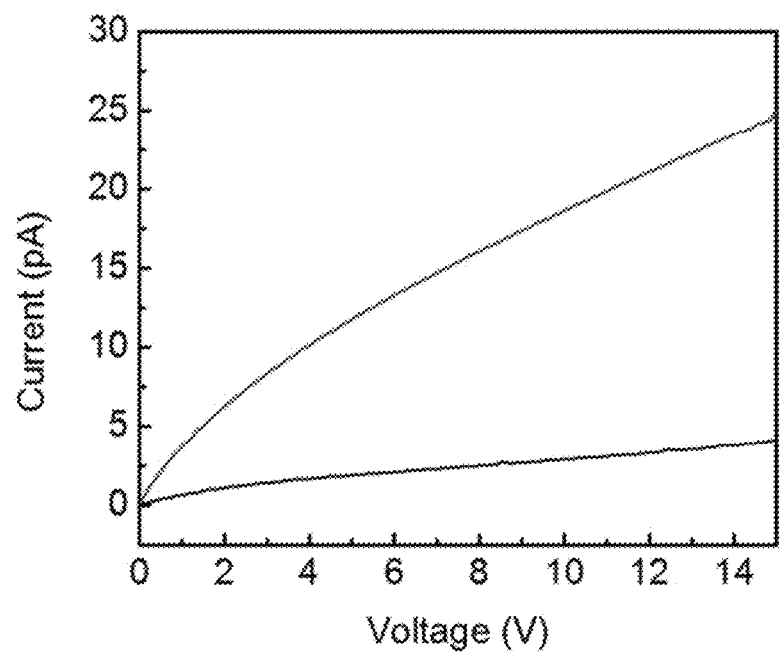

FIG. 21A is a graph of the photocurrent enhancement and sensor performance measured on a post-mixing fibril composite of ACTC and PTCDI-DD. The dark current (lower) and photocurrent (upper) are shown in a typical post-mixing composite.

Figure 21B:
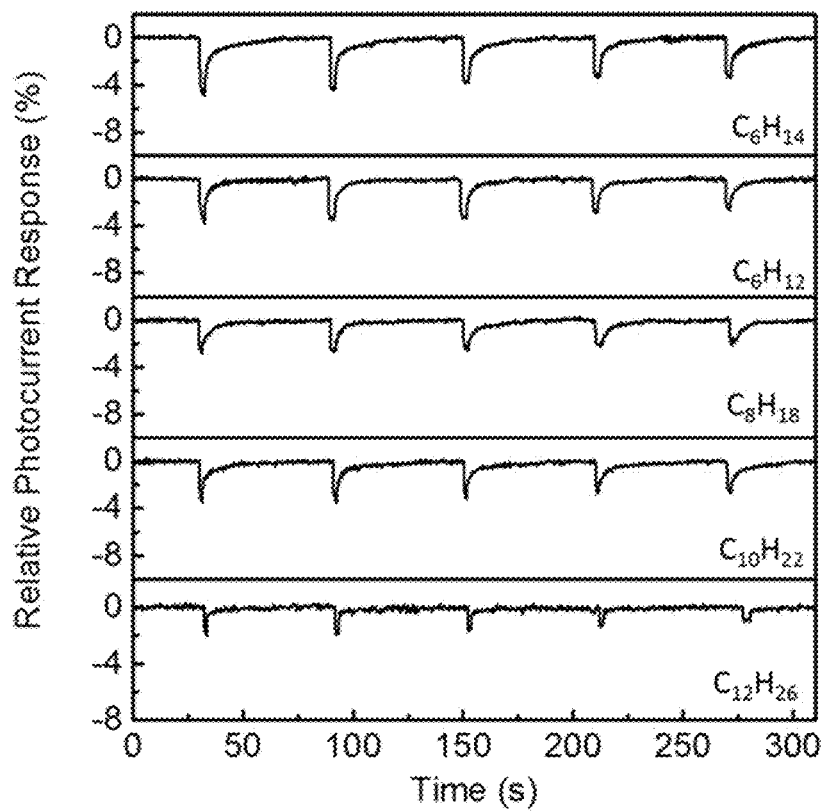

FIG. 21B is a graph showing sensor performance of the post-mixing composite from FIG. 21A. Relative photocurrent response (baseline corrected) toward saturated vapors of n-hexane ($C_6H_{14}$), cyclohexane ($C_6H_{12}$), n-octane ($C_8H_{18}$), n-decane ($C_{10}H_{22}$), and n-dodecane ($C_{12}H_{26}$), at room temperature.

Figure 22A:
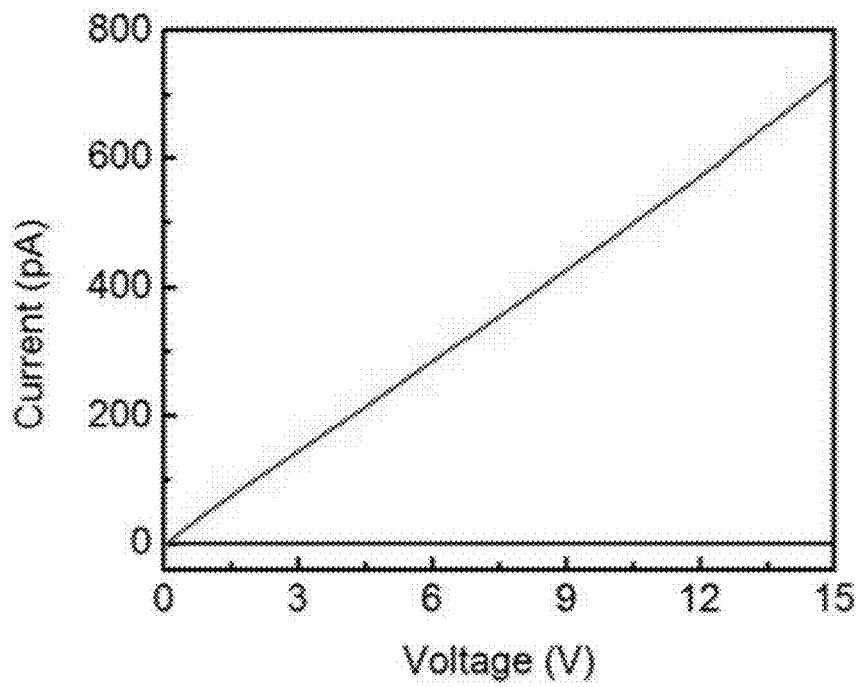

FIG. 22A is a graph of the photocurrent enhancement and sensor performance measured on an ACTC drop casting composite. The dark current (lower) and photocurrent (upper) are shown in a typical ACTC drop casting composite.

Figure 22B:
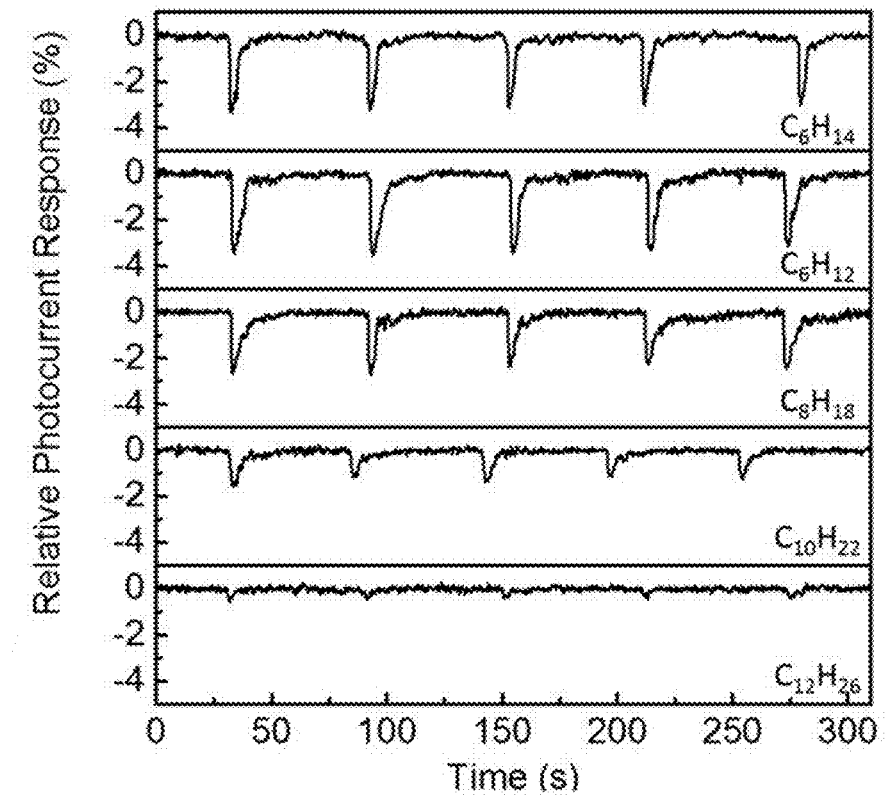

FIG. 22B is a graph of sensor performance of the ACTC drop casting composite of FIG. 22A. Relative photocurrent response (baseline corrected) toward saturated vapors of n-hexane ($C_6H_{14}$), cyclohexane ($C_6H_{12}$), n-octane ($C_8H_{18}$), n-decane ($C_{10}H_{22}$), and n-dodecane ($C_{12}H_{26}$), at room temperature.

Figure 23A:
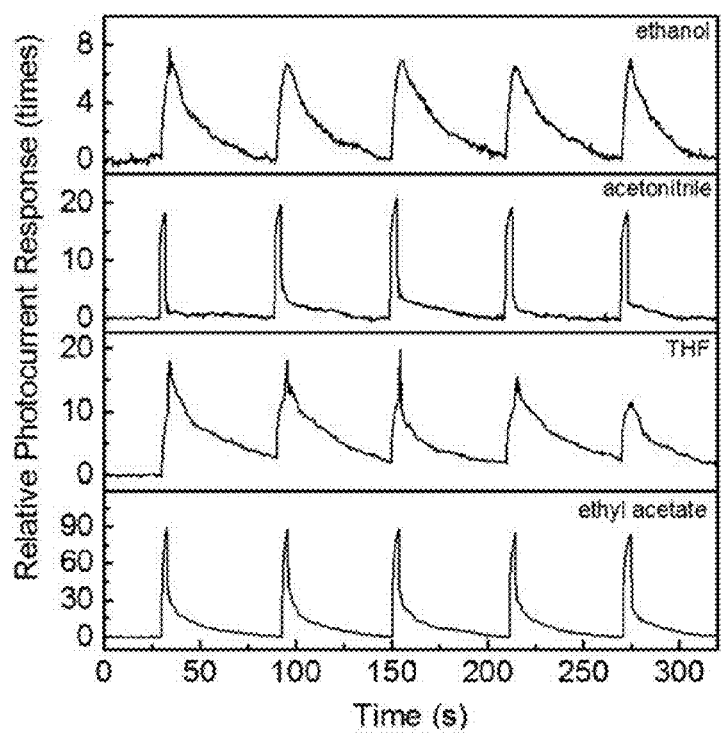
Figure 23B:
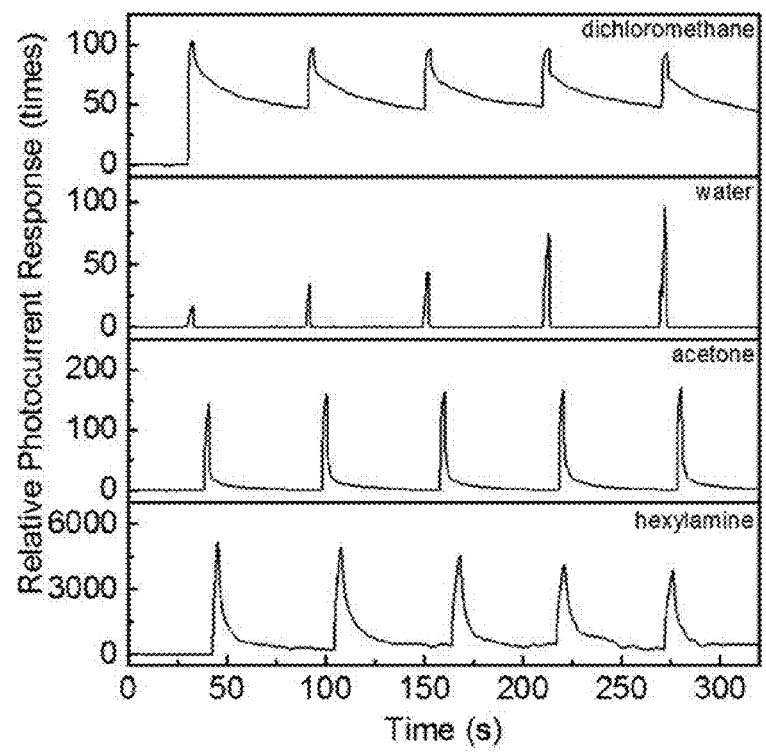

FIGS. 23A and 23B shows the relative photocurrent responses (baseline corrected) measured on an ACTC/PTCDI-DD composite toward interferent vapors at room temperature. The ratio of ACTC to PTCDI-DD is 1:2. From the top to bottom, each curve represents the relative photocurrent response to a saturated vapor of (FIG. 23A) ethanol, acetonitrile, tetrahydrofuran (THF), and ethyl acetate; while FIG. 23B shows dichloromethane, water, acetone, and hexylamine.

Figure 24:
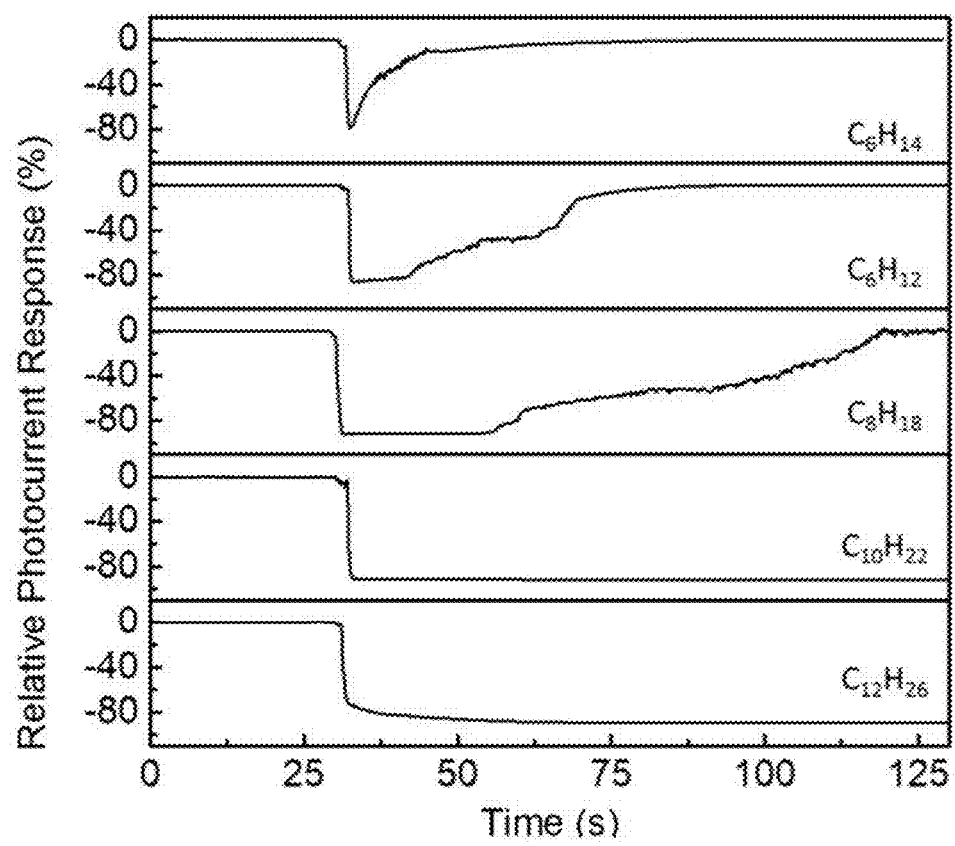

FIG. 24 is a graph of the relative photocurrent responses (baseline corrected) measured on an ACTC/PTCDI-DD composite exposed to droplet of alkane liquid. From the top to bottom, the curves represent the relative photocurrent response to 5 µL of liquid of pure n-hexane ($C_6H_{14}$), cyclohexane ($C_6H_{12}$), n-octane ($C_8H_{18}$), n-decane ($C_{10}H_{22}$), and n-dodecane ($C_{12}H_{26}$).

Figure 25A:
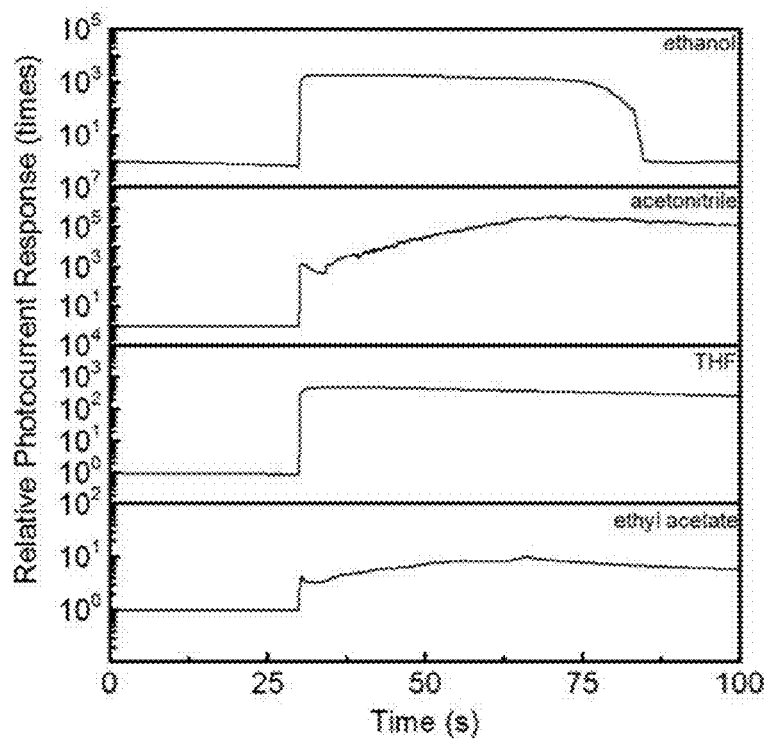
Figure 25B:
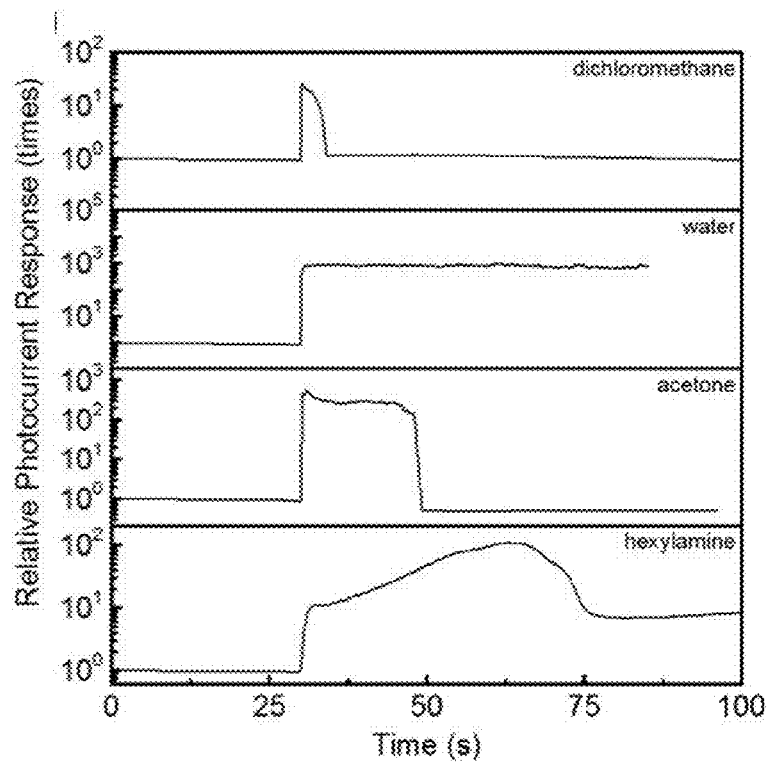

FIGS. 25A and 25B are graphs of the relative photocurrent responses (baseline corrected) measured on an ACTC/PTCDI-DD composite exposed to a droplet of interferent liquid. From the top to bottom, the curves represent the relative photocurrent response to 5 µL of liquid of pure (FIG. 25A) ethanol, acetonitrile, THF, and ethyl acetate; while FIG. 25B shows dichloromethane, water, acetone, and hexylamine.

Figure 26:
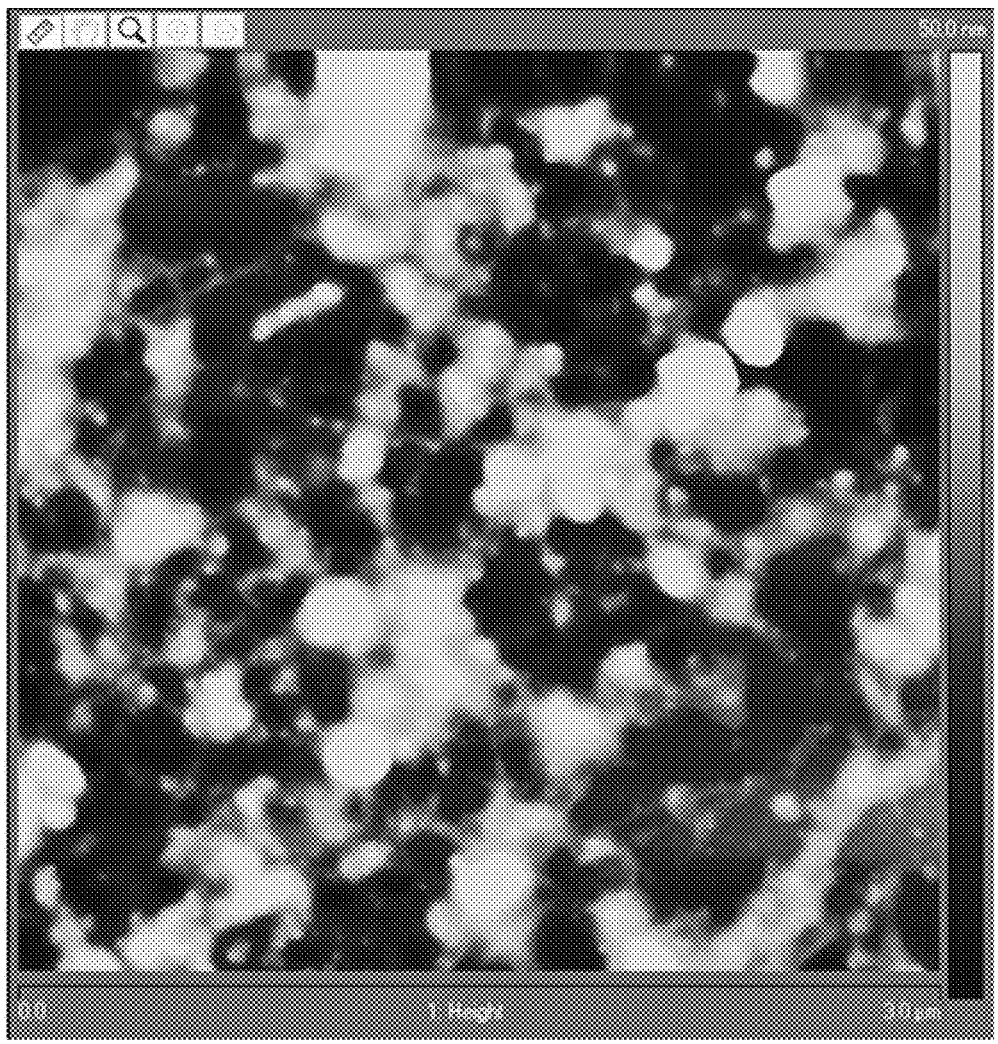

FIG. 26 is an atomic force micrograph of carbon nanotubes coated with poly-3-hecylthiophene in accordance with one example of the present invention.

Figure 27A:
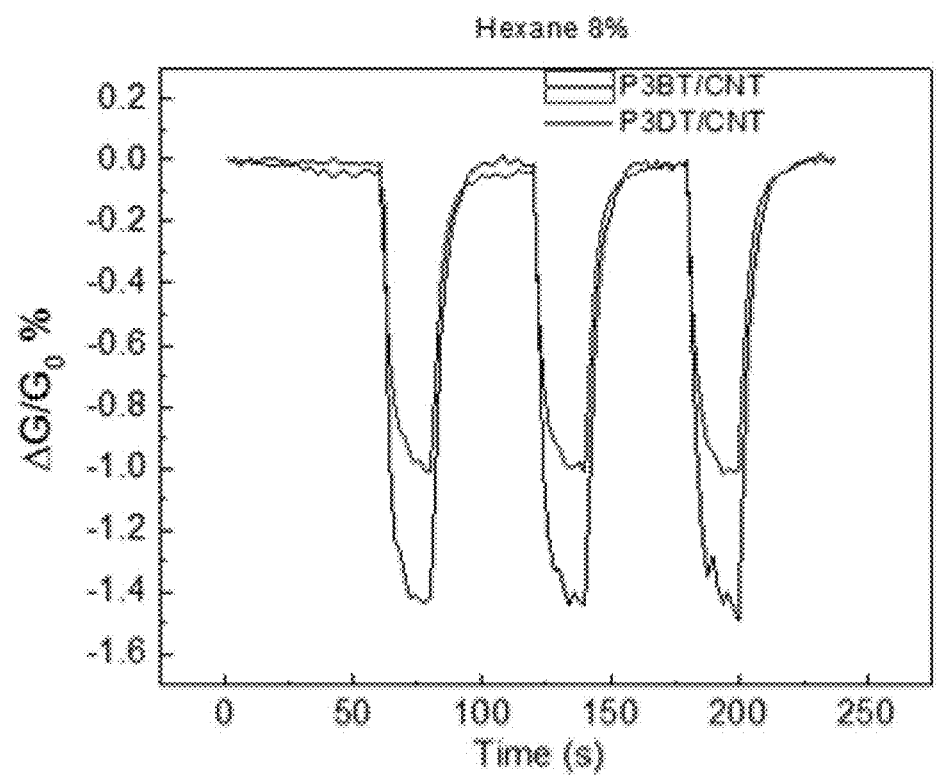
Figure 27B:
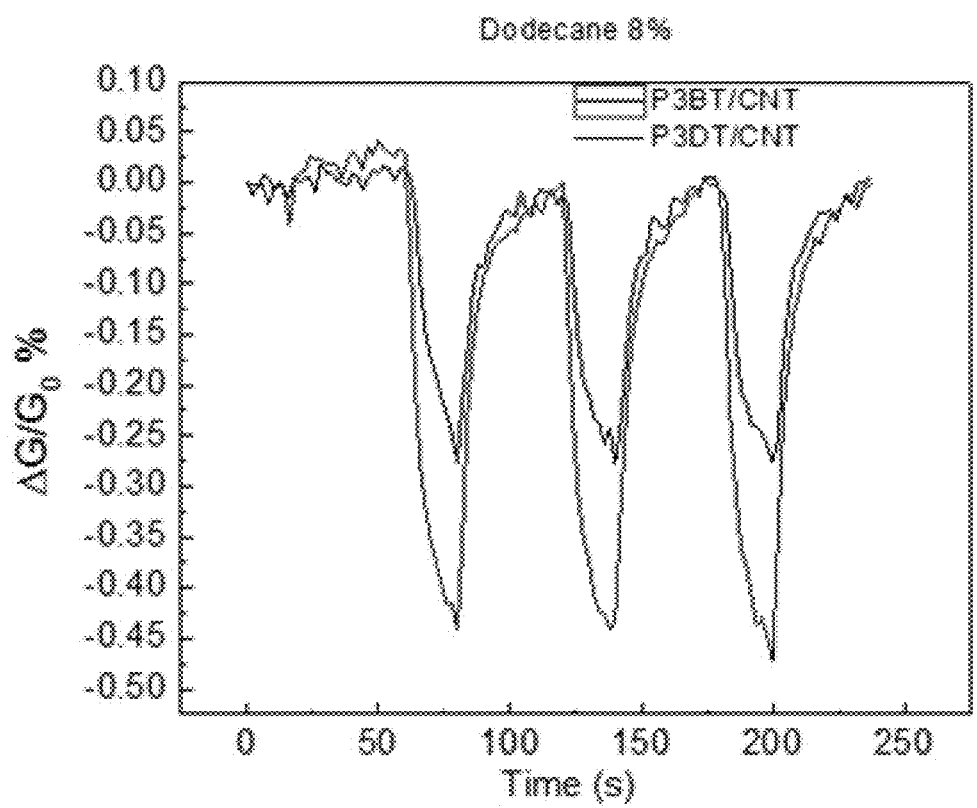

FIGS. 27A and 27B are graphs of sensor response to hexane vapor for four different sensor materials.

Figure 27C:
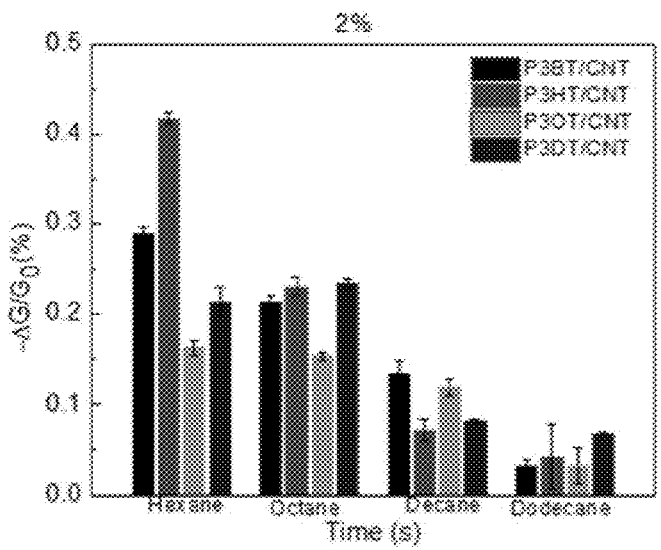
Figure 27D:
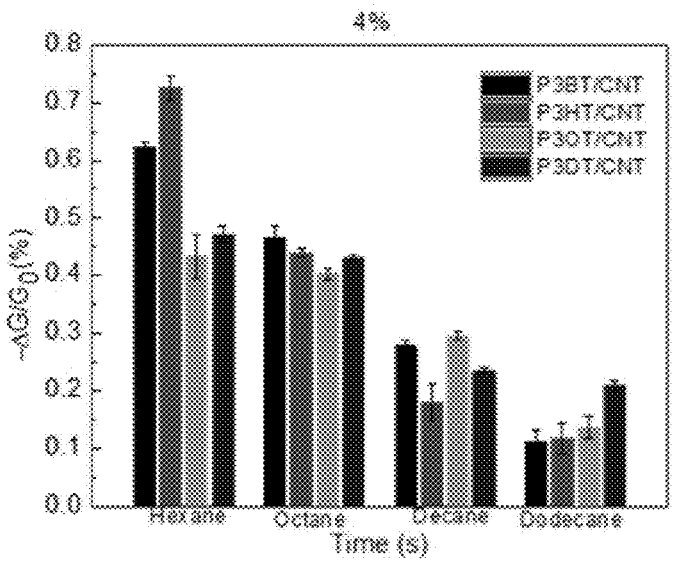
Figure 27E:
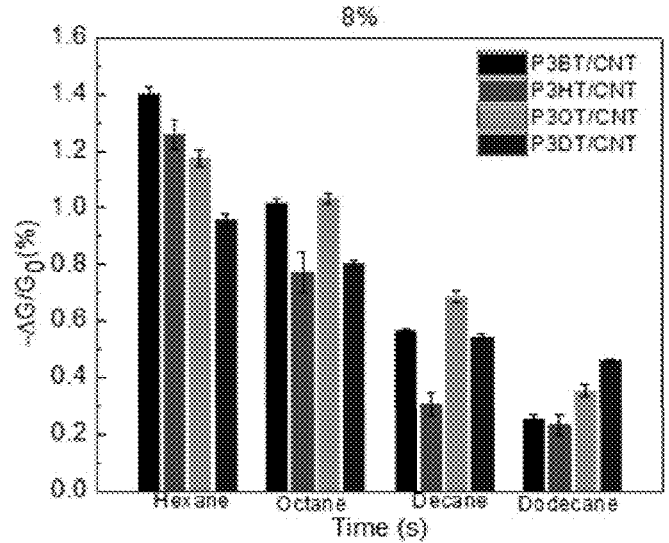

FIG. 27C-E illustrate the selectivity of each sensor to different analytes.

Figure 27F:
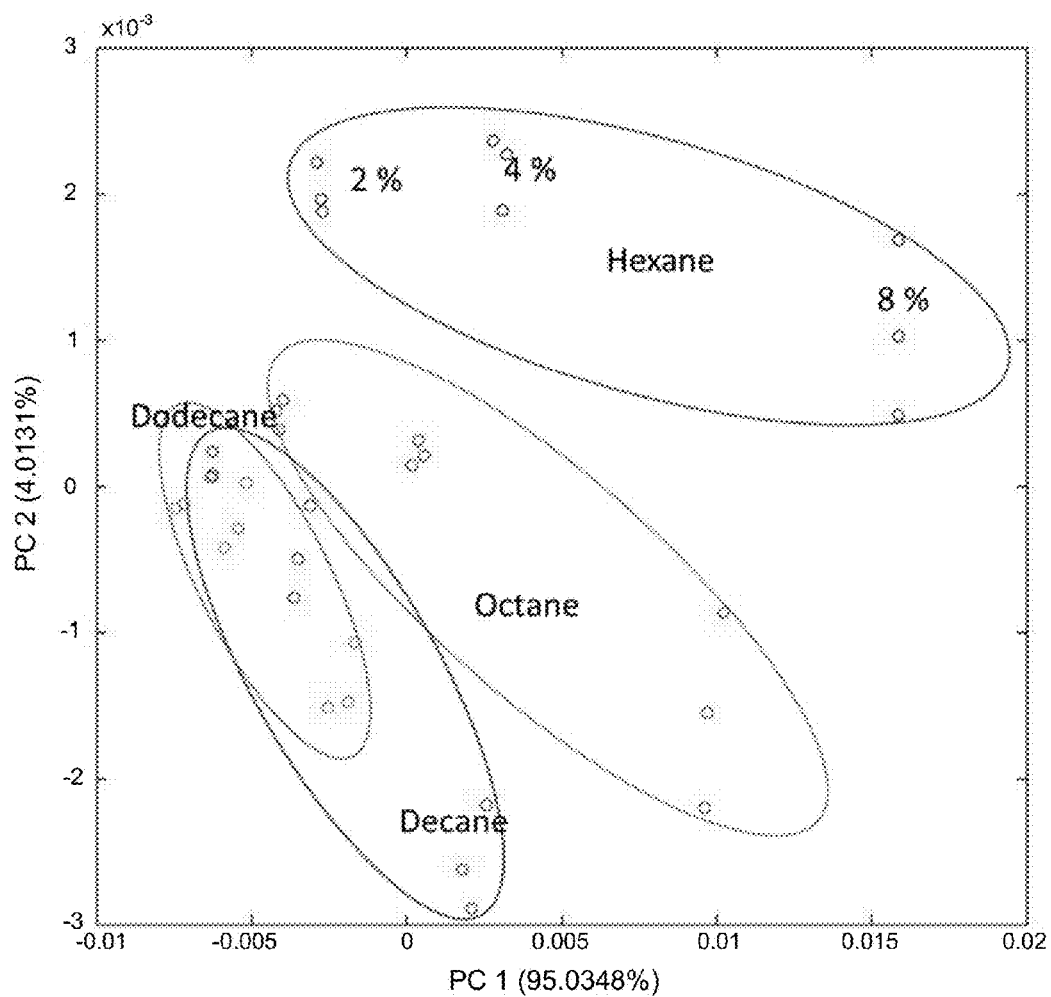

FIG. 27F is a graph of principal component analysis results of the sensor responses.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a fiber" includes reference to one or more of such materials and reference to "exposing" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Interfacial Nanofibril Composites for Selective Alkane Vapor Detection

An initial overview of invention embodiments is provided below and specific embodiments are then described in further detail. This initial summary is intended to aid readers in understanding the technological concepts more quickly, but is not intended to identify key or essential features thereof, nor is it intended to limit the scope of the claimed subject matter.

A sensor material based on an organic nanofibril composite that can detect alkanes with both high sensitivity and selectivity when employed in a chemiresistive sensor is described herein. More specifically, a nanofiber composite sensor for detecting alkanes can include a network of contacting nanofibers having multiple contact points. Each of the plurality of contact points can form an interfiber interface of interdigitated alkyl chains. Alkanes can be adsorbed at the interfiber interface to increase an interfiber distance between the contacting nanofibers, which can decrease the charge transfer efficiency between the contacting nanofibers.

A complimentary method of detecting alkanes can include exposing a network of contacting nanofibers to a suspected target compound source. As described above, the contacting nanofibers can have multiple contact points, where each of the plurality of contact points can form an interfiber interface of interdigitated alkyl chains. The method can further include measuring an electrical response of the network of nanofibers. Alkanes adsorbing at the interfiber interface can increase an interfiber distance between the contacting nanofibers, which can decrease the charge transfer efficiency between the contacting nanofibers. The method can further include displaying a detection metric based on the electrical response kinetics.

In further detail, the nanofiber composite can form a nanofiber film having a large surface area and three-dimensional porosity. In some examples, the large surface area and three-dimensional porosity of the nanofiber film can enhance the adsorption, accumulation, and diffusion of gas molecules, resulting in high detection sensitivity.

Further, the unique interfiber interface, composed of interdigitated alkyl chains, can provide preferential adsorption sites for alkanes through solvophilic (van der Waals) interactions. When alkane molecules are adsorbed at the interface, the original side-chain interdigitation can be fractionally interrupted, leading to an increase in the interfiber distance. This increase in interfiber distance tends to weaken the interfiber charge transfer and thus decrease the interfiber electrical conductivity. Furthermore, alkanes of different sizes demonstrate unique and distinguishable kinetic characteristics in the signals they invoke, which can provide a measurable discrimination between the alkanes themselves.

Figure 1A:
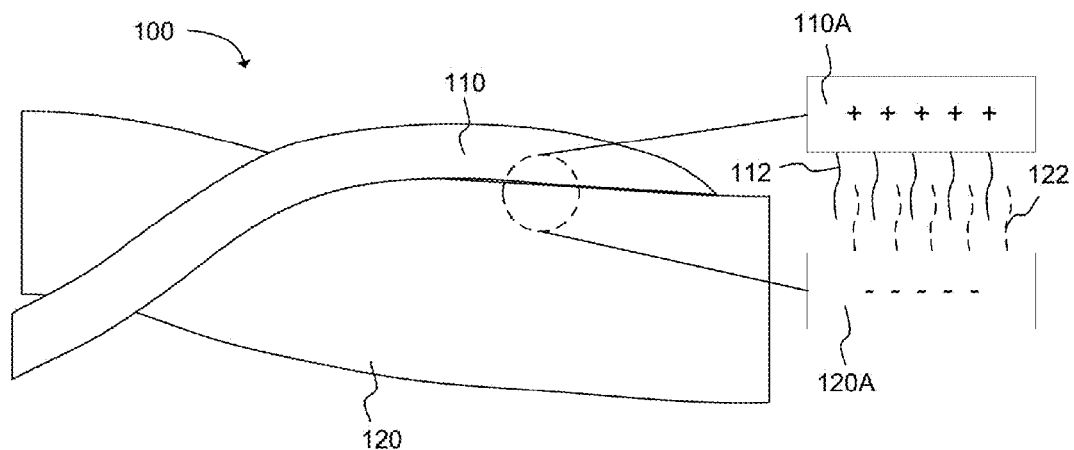
FIG. 1A is a graphical representation of the process of an alkane interacting at the donor-acceptor interface of a coassembly from donor and acceptor molecules, in accordance with one example of the present invention.
Figure 1B:
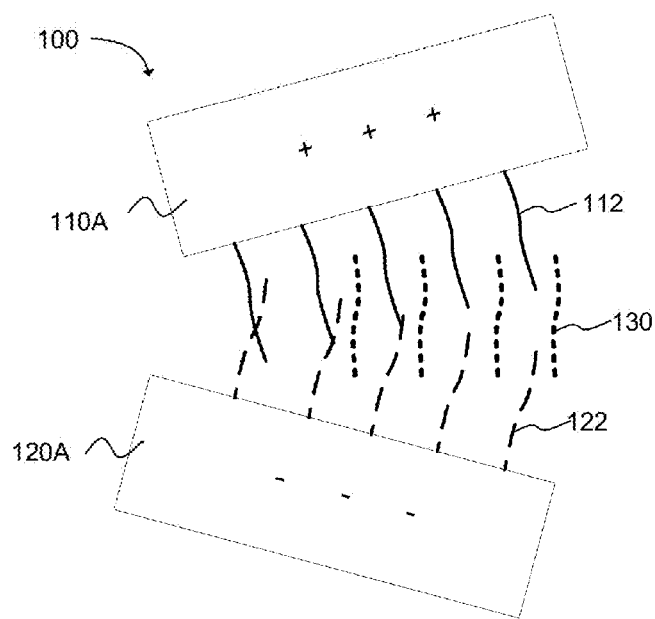
FIG. 1B is an expanded view of the donor-acceptor interface of FIG. 1A showing alkanes interacting with and disrupting interdigitation of alkyl side groups.

This process is generally depicted in FIGS. 1A and 1B. As illustrated in FIG. 1A, a nanofiber composite 100 can include a first nanofiber 110 and a second nanofiber 120. In some examples, the first nanofiber 110 can be a donor nanofiber and the second nanofiber 120 can be an acceptor nanofiber, or vice versa. Regardless, the first nanofiber 110 and the second nanofiber 120 can contact one another at a plurality of contact points. One such area of contact is graphically magnified as part of FIG. 1A merely for illustration purposes. This magnified view depicts a first nanofiber section 110A having alkyl chains 112 and second nanofiber section 120A having alkyl chains 122. The first nanofiber section 110A (donor nanofiber) is indicated as being positively charged and the second nanofiber section 120A (acceptor nanofiber) is indicated as being negatively charged. The alkyl chains 112 and alkyl chains 122 at the area of contact are interdigitated.

However, as illustrated in FIG. 1B, when the nanofiber composite 100 is exposed to alkanes 130, the adsorption of alkanes 130 at an interfiber contact area can cause the nanofibers to separate. For example, in the region illustrated by FIG. 1B, adsorption of alkanes 130 at the interfiber interface can increase the interfiber distance between a first nanofiber section 110A and a second nanofiber section 120A. This separation can decrease the charge transfer between the interconnected nanofibers, which can be detected as a decrease in current across the sensor material. It is noted that the detected alkanes 130 can be in a vapor phase, liquid phase, or a combination thereof.

The nanofiber composite can include a variety of nanofiber materials. As previously discussed, in some examples, the nanofiber composite can include donor nanofibers, acceptor nanofibers, or combinations thereof. In one specific example, the contacting nanofibers can include a first nanofiber as a donor nanofiber formed of a donor molecule and a second nanofiber is an acceptor nanofiber formed of an acceptor molecule. In some further examples, the first and second nanofibers can have an induced charge transfer process between them, such as a photo-induced, thermally induced, or otherwise induced charge transfer process. In yet some additional examples, the first and second nanofibers can interact to create a homogeneous donor-acceptor interface at the interfiber interface. In some examples, a homogeneous interface can result from interdigitation of alkyl side chains to form a continuous or uniform film which is not phase separated such that the interface is substantially only or consists essentially of the alkyl side chains.

A variety of donor molecules can be used to prepare donor nanofibers. Non-limiting examples of donor molecules can include thiophenes (e.g. oligothiophene, polythiophene), oligofluorene, polyfluorene, oligocarbazole, polycarbazole, arylene-ethynylene tetracycline, dithiophene, [1]benzothieno[3,2-b][1]benzothiophene, anthracene, tetracene, pentacene, phthalocyanines, pyrene, perylene, oligo(p-phenylene vinylene) (OPV), poly(p-phenylene vinylene) (PPV), the like, or combinations thereof. In some specific examples, the donor molecules can include

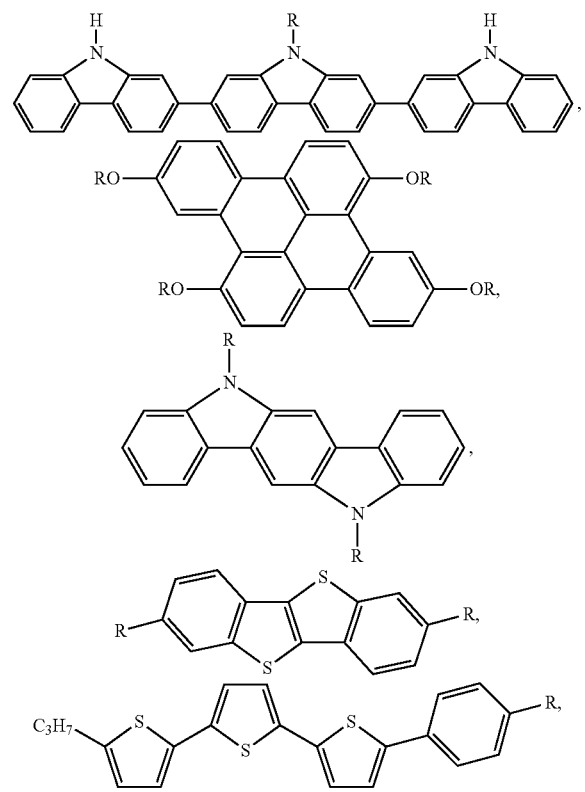

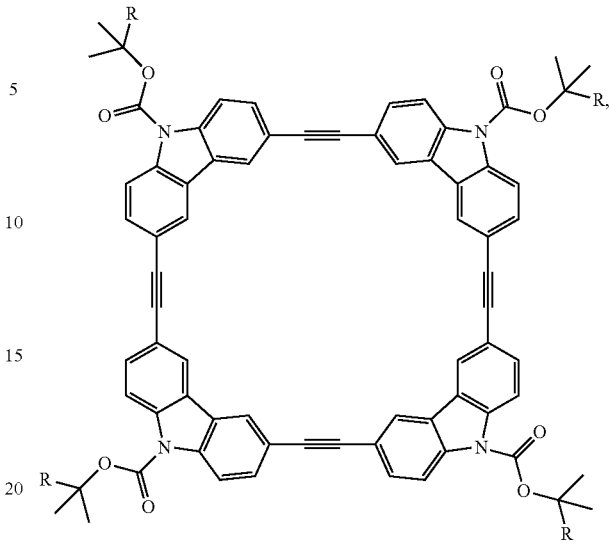

the like, or combinations thereof. In this particular example, R can generally be $C_nH_{2+1}$ or $O—C_nH_{2n+1}$ where n=1-30, or in some cases n=4-20 or n=6-16. However, in some other examples, R can be an alkyl group selected from the group consisting of butyl, pentyl, hexyl, heptly, octyl, nonyl, decyl, undecyl, dodecyl, tridecyl, tetradecyl, and combinations thereof.

In one specific example, the donor nanofiber can be a long alkyl-substituted arylene-ethynylene tetracycle (ACTC where alkyl side chain has n greater than 8 and in some cases is 12). In other examples, the donor interface of interdigitated alkyl chains can include or be formed of a member independently selected from the group consisting of thiophenes (e.g. oligothiophene, polythiophene), oligofluorene, polyfluoene, oligocarbazole, polycarbazole, arylene-ethynylene tetracycline, dithiophene, [1]benzothieno[3,2-b][1]benzothiophene, anthracene, tetracene, pentacene, phthalocyanines, pyrene, perylene, oligo(p-phenylene vinylene) (OPV), poly(p-phenylene vinylene) (PPV), and combinations thereof.

The acceptor nanofibers can similarly be formed from a variety of acceptor molecules. Non-limiting examples can include 3,4,9,10-perylenedicarboximide (PTCDI), naphthalene diimide (NDI), pyrrolo[3,4-c]pyrrole-1,4-dione (PPO), the like, or combinations thereof. In some specific examples, the acceptor molecules can include

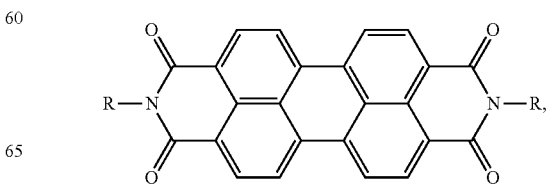

-continued

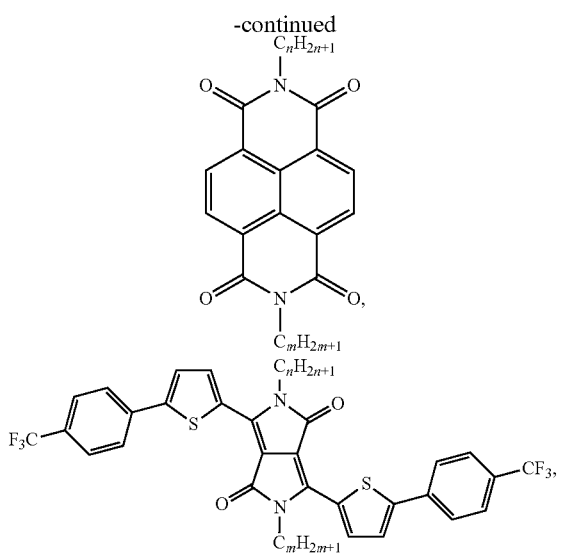

the like, or combinations thereof, where m and n are independent integer variables ranging from 1-30, or in some examples from 8-16, and where R can be a substituted or unsubstituted, linear, branched, or cyclic $C_1$-$C_{30}$ alkyl group. In one specific example, the acceptor nanofiber can be made of a perylene-3,4,9,10-tetracarboxylic-3,4,9,10-diimide (PTCDI) compound.

Figure 2A:
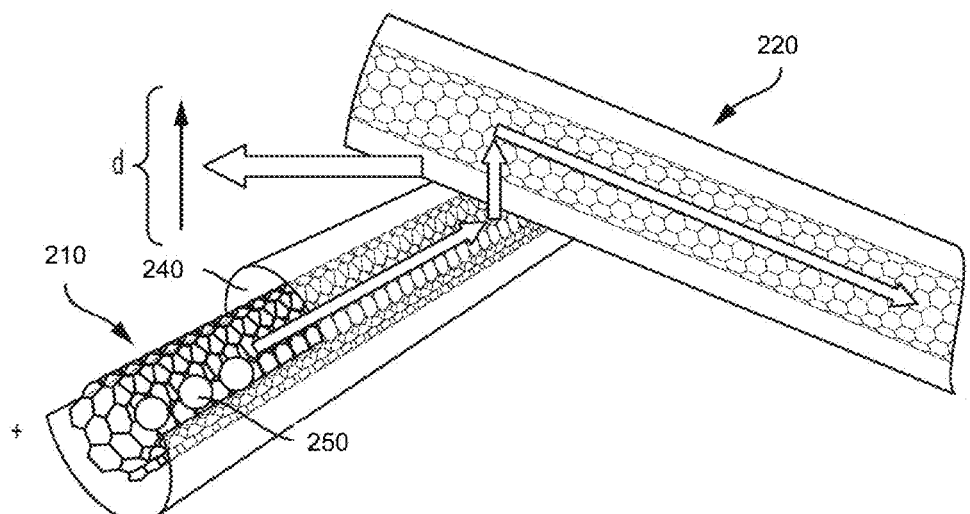
FIG. 2A is a graphical representation of adjacent contacting carbon nanotubes non-covalently bonded with a dispersant having hydrophobic alkyl groups, in accordance with one example of the present invention.
Figure 2B:
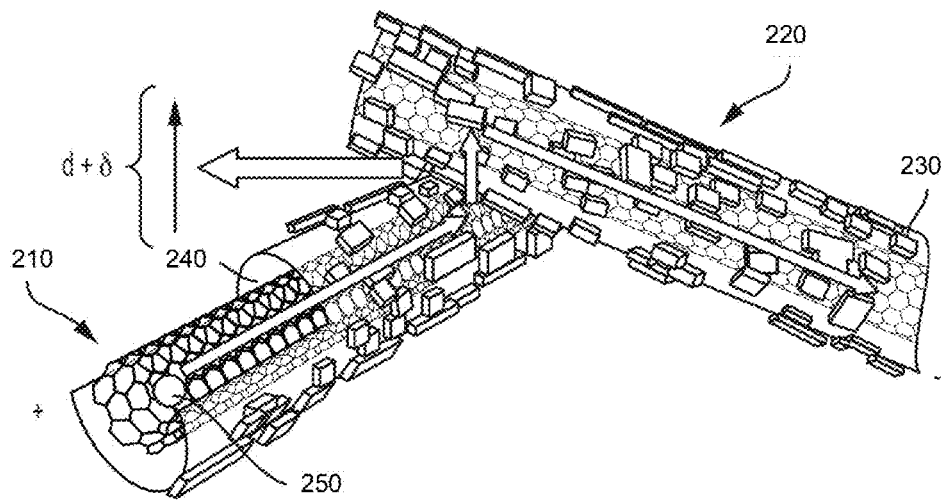
FIG. 2B is a graphical representation of the contacting carbon nanotubes of FIG. 2A having an alkanes adsorbed on surfaces of the carbon nanotubes which increases interfiber distance in accordance with one example.

In yet other examples, shown generally in FIG. 2A, the first nanofiber 210 and the second nanofiber 220 can be carbon nanotube fibers, such as single-wall or multiple-wall carbon nanotube fibers. In some examples, the carbon nanotubes can be covalently or non-covalently modified. In some specific examples, the carbon nanotubes can be non-covalently modified with a carbon nanotube dispersant 240, which can include or provide interdigitated alkyl chains. Non-covalent modification can be advantageous in some examples because non-covalent modification can help preserve the band structure of the carbon nanotubes. In some examples, the first nanofiber 210 and the second nanofiber 220 can be compositionally homogeneous. In yet other examples, the first nanofiber 210 and the second nanofiber 220 can be compositionally distinct. In either case, the first and second nanotube fibers can contact one another to form a variable charge transfer efficiency at the interfiber interface between contacting fibers. Thus, as illustrated in FIG. 2B, adsorption of a target compound at an area of interfiber interface can cause the dispersant coating to swell and increase the interfiber distance between the first and second nanofibers, which can reduce the charge transfer efficiency between the contacting nano fibers.

In further detail, the conductivity of the nanofiber composite can be from the carbon nanotube network itself, without need of further energy activation. The dispersant coating 240 can provide charge carrier tunnel barriers at the various junctions of the carbon nanotube fiber network. The charge carrier (holes) 250 in the carbon nanotube network can tunnel through the interfaces formed by the dispersant coating 240. However, when the dispersant coating 240 is exposed to a target compound, the coating can swell and increase the tunnel barrier in the CNT network, thus reducing the conductivity of the sensor material.

A variety of dispersants can be used to form the dispersant coating. Non-limiting examples can include a monomer, oligomer, or polymer of thiophene, pyrene, carbazole, fluorene, phenylene, arylene, vinylene, aniline, imine, azole, pyrrole, porphyrin, phthalocyanine, acenes, DNA, naphthalene, anthracene, perylene, styrene, the like, or a combination thereof. In some specific examples, the carbon nanotube dispersant can include

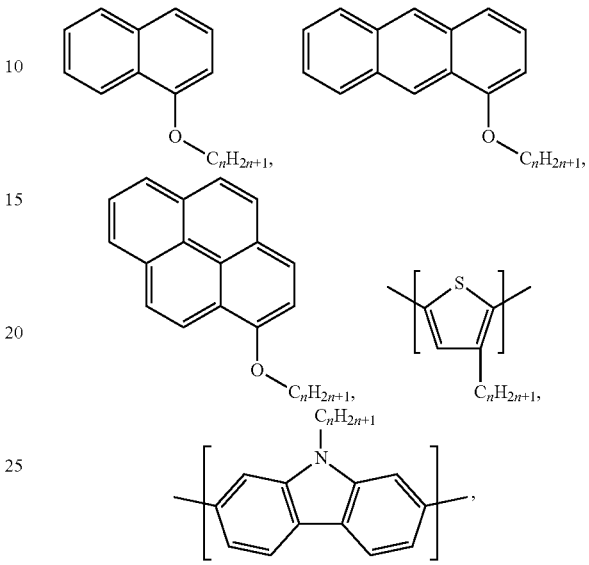

the like, or combinations thereof, where n is 1-30, or in some cases n=4-20 or n=6-16. In yet other examples, the carbon nanotube dispersant can include

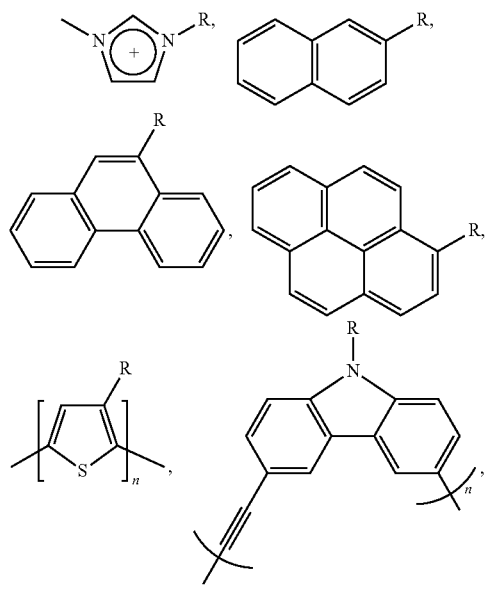

the like, or combinations thereof, where R can generally be $C_nH_{2n+1}$ or O—$C_nH_{2n+1}$ where n=1-30, or in some cases n=4-20 or n=6-16. In some specific examples, R can be an alkyl group selected from the group consisting of butyl, pentyl, hexyl, heptyl, octyl, nonyl, decyl, undecyl, dodecyl, tridecyl, tetradecyl, and combinations thereof.

It is noted that a variety of R groups or interdigitated alkyl chains can be used with the nanofibers described herein, such as those discussed above. Generally, the interdigitated alkyl chains can include at least one substituted or unsubstituted, branched, cyclic, or straight hydrophobic alkyl chain (e.g. $C_nH_{2n+1}$, $O-C_nH_{2n+1}$, or the like, for example), wherein n=1-30, or in some additional examples n=4-20 or n=6-16. Non-limiting examples of straight chain alkyls can include ethyl, butyl, pentyl, hexyl, heptyl, octyl, nonyl, decyl, etc. Non-limiting examples of branched alkyls can include hexyl-heptyl, heptyl-octyl, octyl-nonyl, nonyl-decyl, etc. Non-limiting examples of cyclic alkyls can include cyclopentyl, cyclohexyl, etc.

Coverage of the interdigitated alkyl chains can vary across surfaces of the nanofibers. In some aspects, the interdigitated alkyl chains can be distributed across substantially an entire surface of the nanofibers. However, the interdigitated alkyl chains can alternatively cover a portion of the nanofiber surfaces such as from 50% to 99% and in some cases from 75% to 95% of the nanofiber surfaces.

Therefore, a variety of nanofiber materials can be used to prepare the nanofiber composite material of the chemiresistive sensor. In some cases, each nanofiber can be prepared from a common starting compound. However, in some cases each nanofiber may be formed from mixtures of two or more starting compounds. Further, depending on the particular nanofiber materials selected, the nanofiber composite material can be employed somewhat differently to detect a target compound, such as an alkane.

Figure 3A:
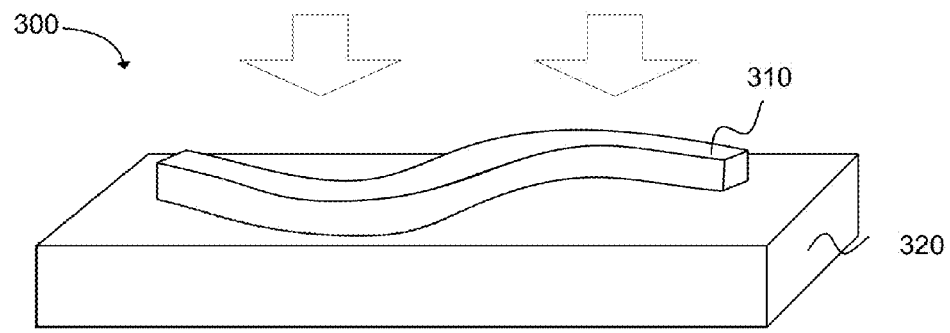
FIGS. 3A and 3B are graphical representations of an alkane interacting at the donor-acceptor interface of a coassembly of nanofiber materials made from donor and acceptor molecules, in accordance with one example of the present invention.
Figure 3B:
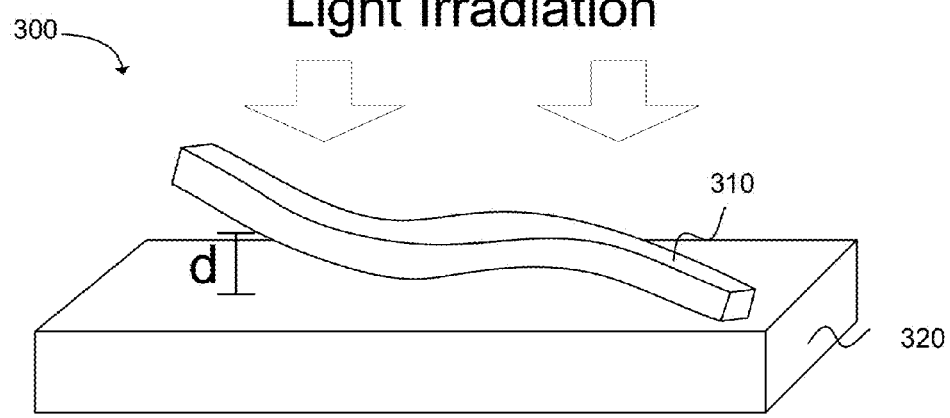

For example, as discussed above, where a donor and acceptor nanofiber are used in combination, it can often be advantageous to induce a current between the contacting nanofibers. General reference will be made herein to a photoinduced current for the sake of brevity and clarity. However, this is not intended to be limiting unless specified, as other methods of inducing current can also be used. With that in mind, FIGS. 3A and 3B generally illustrate how the donor-acceptor nanofiber composite can be used. In this particular example, the nanofiber composite 300 can be irradiated with light to generate a photocurrent across the donor nanofiber 310 and the acceptor nanofiber 320. However, as illustrated in FIG. 3B, upon adsorption of a target compound the interfacial distance between the two nanofiber materials can increase by a distance d. This increased distance between the two nanofibers can cause a decrease in charge transfer between the two fibers resulting in a detectable decrease in photocurrent across the nanofiber composite material. Thus, the efficiency of photoinduced charge transfer (PCT) can be strongly dependent on the interfiber distance at the interface. Notably, for the donor-acceptor nanofiber interface illustrated in FIGS. 3A and 3B, the conductivity (or electrical current) can be initiated by a photoinduced electron transfer from donor to acceptor fiber through the interface, thus creating charge separation, i.e., generating charge carriers (with electrons in the acceptor fiber and holes in the donor fiber). Absorption of alkanes at the interface interrupts the charge transfer space (considering both distance and configuration), thereby changing the current. Thus, donor and acceptor fibers can be used to facilitate photoinduced charge transfer (photoconductivity).

This is distinct from the carbon nanotube system illustrated in FIG. 2A in which no photo-illumination is generally needed to enhance the conductivity, as carbon nanotubes are intrinsically highly conductive. In this system, adsorption of an alkane pushes adjacent nanofibers apart at the interfiber interface, which reduces the charge transfer (decreasing the current). The two sides of the interdigitated alkyl interface are side chains of polymers on opposing carbon nanotubes. The backbones of the polymers sit on the carbon nanotubes surface. In order for a charge to move from one electrode to the other (i.e., for an electric current to exist), the charge transfers from one carbon nanotube to the next through these polymer/alkyl junctions. Adsorption of an alkane pushes the carbon nanotubes apart, which reduces the number of charges that can move through the junction at the interfiber interface, which increases the resistance. In this case, no photoexcitation is required, although may be used depending on the particular materials and configuration to enhance response of the fibers. This effect can also be realized through multi-walled carbon nanotubes covalently or non-covalently modified or functionalized to include alkyl groups such as those previously enumerated.

The nanofiber composites described herein can be prepared via a number of methodologies. In one specific example, an interfacial donor-acceptor (D-A) nanofibril composite can be fabricated from donor (D) and acceptor (A) molecules simultaneously via one-step self-assembly in a solution. In some examples, the D molecule can be based on alkyl-substituted arylene-ethynylene tetracycle (ACTC) and the A molecule can be based on perylene-3,4,9,10-tetracarboxylic-3,4,9,10-diimide (PTCDI). Both molecules (ACTC and PTCDI) can form well-defined nanofibers, though in different sizes. By tuning the side groups of PTCDI among different molecular structures, such as dodecyl (-DD), cyclohexyl (-C6), and propoxyethyl (-PE), for example, the impact of the D-A interface on the photocurrent generation, as well as the chemiresistive sensing to alkanes can be observed. Additionally, beyond the molecular modification, by tuning the D-A interfacial structure via various fabrication methods, the relationship between the D-A interface and desired sensor performance can be determined. Through these investigations, an interfacial D-A composite composed of bulk-heterojunctions of two nanofibers co-assembled from PTCDI-DD and ACTC can be formed. By monitoring the change in photocurrent, alkanes of different sizes can be distinguished based on their unique kinetics of photocurrent responses. Moreover, the sensor can provide opposite response trends to alkanes over common solvents, which can provide good general selectivity for practical applications.

Alternatively, a carbon nanotube network can be formed by drop or spin casting a solution of carbon nanotubes coated with a dispersant, the latter of which forms a uniform thin film on the surface of the carbon nanotube. These nanofibers can be also be tuned and evaluated in a similar manner to the D-A nanofibers described above.

Additionally, the composite sensor can typically include a pair of electrodes electrically associated with the nanofiber network such that a carrier injection process occurs across the network and the sensing material can be fabricated into chemiresistors such that the alkane vapor can be detected via monitoring the electrical current change. Thus, the electrodes can be electrically connected to a charge measurement module (e.g. a voltage meter, current meter, etc) which relays changes in current to a display, computing device or other module which can trigger a visual notice or electronic signal. Typically, the composite sensor can be activated by introducing energy (e.g. photoactivation). However, for configurations using carbon nanotube fibers, charge transfer and sensitivity can be effective in the absence of an activation energy, although an activation energy can in some cases improve performance.

A complimentary method of detecting alkanes can include exposing a network of contacting nanofibers having multiple contact points, where the contact points can each form an interfiber interface of interdigitated alkyl chains, to a suspected target compound source. The method can further include measuring an electrical response of the network of nanofibers caused by the alkanes adsorbing at the interfiber interface and increasing an interfiber distance between first and second nanofibers which can decrease the charge transfer efficiency. The method can further include displaying a detection metric based on the electrical response. As described above, the first and second nanofibers can be either donor nanofibers and acceptor nanofibers, or carbon nanotubes.

Although functional detection temperature can vary considerably depending on the specific materials, in one embodiment, the detection temperature can be −20 to 75° C.

Most often the sensor can be reusable. Also, the limit of detection of the method can generally be below a 5%, 1%, or 0.5% saturated vapor pressure of the target compound. In one embodiment, the electrical response of the network of nanofibers can be discernible between alkanes of different lengths. In another embodiment, the electrical response can distinguish between alkanes in less than 10, 5, or 3 seconds and can provide the detection metric which can be reported within 90, 60, or 30 seconds, depending on device and sensor configurations. The detection metric can be selected from the group consisting of a change in conductivity, change in resistance, change in voltage, change in current, rates of change thereof, and combinations thereof.

Examples

Fabrication of PTCDI, ACTC Nanofibers and ACTC/PTCDI Nanofibril Composites.

ACTC nanofibers, PTCDI nanofibers, and ACTC/PTCDI composites were fabricated using a solution-based method. For single component nanostructures, a 0.1 mM chloroform solution of the building block molecule was prepared. For ACTC/PTCDI composites, the concentration ratios of ACTC and PTCDI were equal to their desired molar ratios and the sum concentration was fixed at 0.2 mM in chloroform solution. 1 mL of the prepared solution was quickly added to 9 mL of ethanol at room temperature while shaking. Then, the over-saturated solution was kept at 4° C. for 12 hours. Some reddish (for PTCDI and ACTC/PTCDI) and pale white (for ACTC) aggregates formed at the bottom of the test tubes. The top clear solution (ca. 9 mL) was carefully removed from the test tubes, leaving the samples in ca. 1 mL solvent. The remaining materials were shaken to form a quasi-uniform mixture, which was ready to be transferred to substrates or electrodes.

SEM Characterization.

The above prepared materials were drop cast onto silicon wafers and left in a vacuum oven to dry at room temperature. The SEM characterization was performed with an FEI Nova Nano 630 (FEI Corporation) equipped with a helix detector.

Photocurrent Measurement.

The photocurrent measurements were carried out using a two-probe method on a Signatone S-1160 Probe Station combined with an Agilent 4156C Precision Semiconductor Parameter Analyzer as partially shown in FIG. 5, FIG. 14, FIG. 21, and FIG. 22. The measurements took place in a shielded dark box to eliminate unwanted light and electromagnetic radiation. The electrodes were fabricated using photolithography on a silicon wafer covered with a 300 nm $SiO_2$ layer. The gold electrode pair was 15 µm in width and 5 µm in gap, and fully covered with the sensor materials via drop casting. A tungsten lamp (Quartzline, 21V, 150 W) was used as the light source for the photocurrent enhancement measurement. The light was guided by an optical fiber and the intensity reaching the sample surface was 60 mW~cm-2, as measured by a Melles Griot broadband power/energy meter (model: 13PEM001).

Vapor and Liquid Sensing Measurement.

The electrodes used in the sensing experiment were interdigitated electrodes fabricated on a quartz wafer, with 20 fingers on each electrode. Each gold electrode pair was about 5 mm in total width, 100 µm in gap. The total chip area was about 5 mm×5 mm in size. For ACTC/PTCDI composites, about 0.2 mL of the quasi-uniform mixture was drop cast onto the electrode and dried in a vacuum oven at room temperature. For the post-mixing composite, 1 mL of the quasi-uniform PTCDI nanofiber suspension and 0.5 mL ACTC nanofiber suspension were mixed and shaken for 4 hours. Then ca. 0.3 mL of the post-mixture was drop cast and dried on an electrode with a similar procedure. For the ACTC drop casting composite, about 0.2 mL of quasi-uniform PTCDI nanofibers was drop cast and dried on an electrode. Then 0.1 mL of 0.1 mM ACTC chloroform solution was drop cast on the PTCDI nanofiber layer. The composite was dried in a vacuum oven at room temperature. After the deposition, the electrodes were connected to an Agilent 4156C Precision Semiconductor Parameter Analyzer for photocurrent measurement. The electrode was fixed in a transparent holder, and was kept 5 cm away from the optical-fiber head, which delivered visible light from a tungsten lamp (Fiber-Lite Fiber Optic Illuminator Model 190, Dolan-Jenner Industries, Lawrence, Mass., 01843). The illumination intensity on the electrode was set at ~20 $mW \cdot cm^{-2}$. In a typical vapor preparation, 50 mL of pure liquid was sealed in a 4 L amber glass bottle for one day at room temperature to reach the liquid-vapor equilibrium state. Before the measurement, the vapor was removed with a 50 mL glass syringe with a 20 cm metal needle. The vapor was also diluted with the same syringe by mixing dry air. The syringe was mounted to a syringe pump (Model: NE-4000, New Era Pump System. Inc.) and fitted with a 5 mm needle. The needle end was fixed 1 cm away from the top of the electrode by a holder. In an alkane exposure test, 5 mL of vapor was pumped from the syringe at a speed of 110 $mL \cdot min^{-1}$, so each exposure time is ca. 3 seconds. The next exposure occurs 1 min after the previous exposure. In the liquid sensing experiment, an Eppendorf Reference Physio Care pipette was used to transfer 5 µL of pure liquid onto the surface of the nanofibers quickly.

Morphology and Photoconductivity.

Figure 4A:
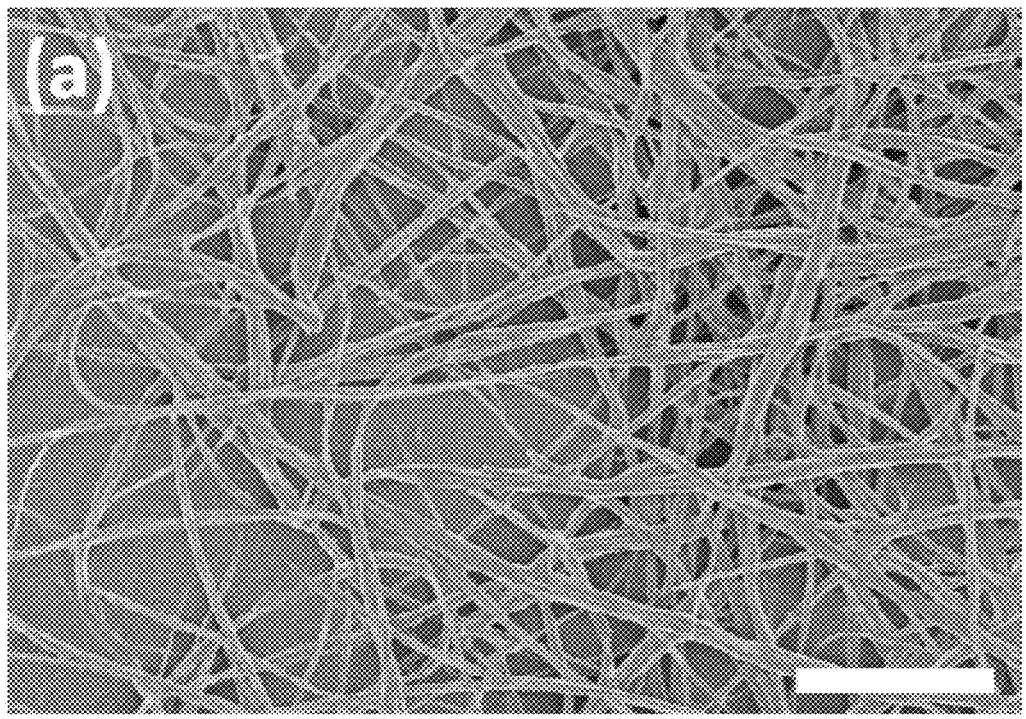
FIG. 4A is an SEM images of PTCDI-DD nanofibers. Scale bar=5 μm.
Figure 4B:
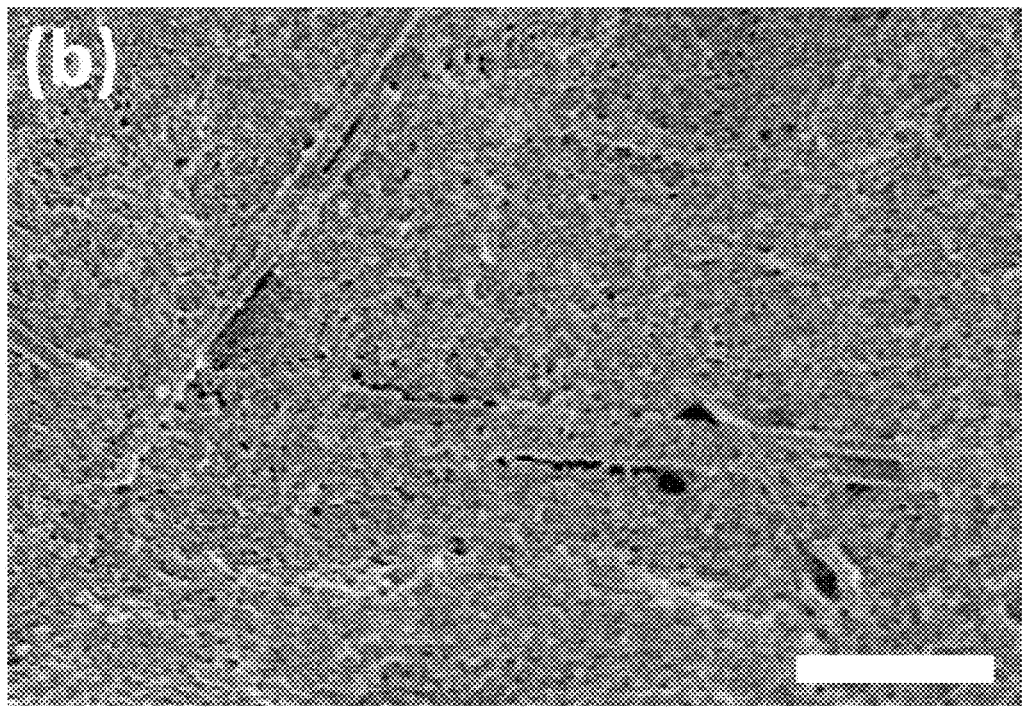
FIG. 4B is an SEM image of ACTC/PTCDI-DD nanofibril composite. Scale bar=5 μm.
Figure 4C:
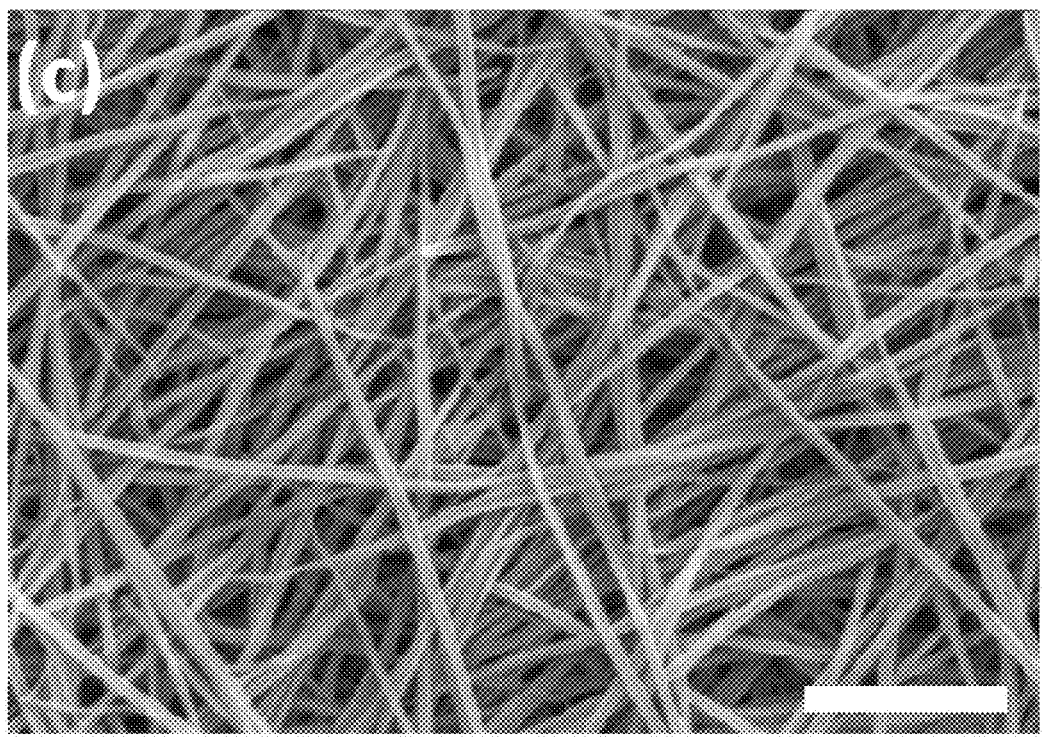
FIG. 4C is an SEM image of PTCDI-$C_6$ nanofiber. Scale bar=5 μm.
Figure 4D:
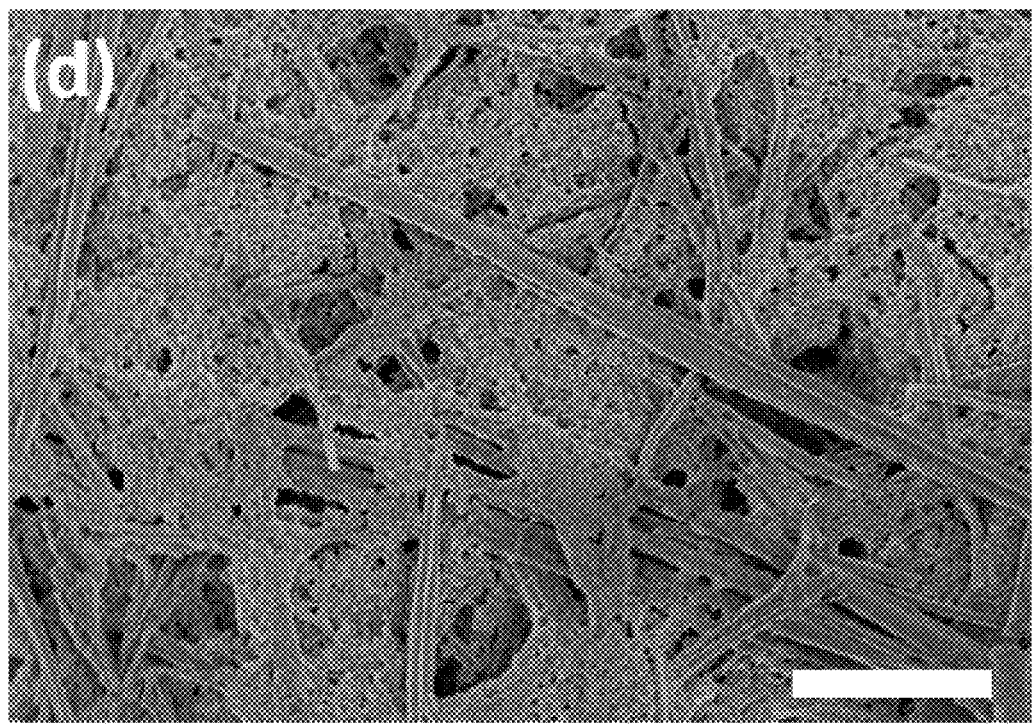
FIG. 4D is an SEM image of ACTC/PTCDI-$C_6$ nanofibril composite. Scale bar=5 μm.
Figure 4E:
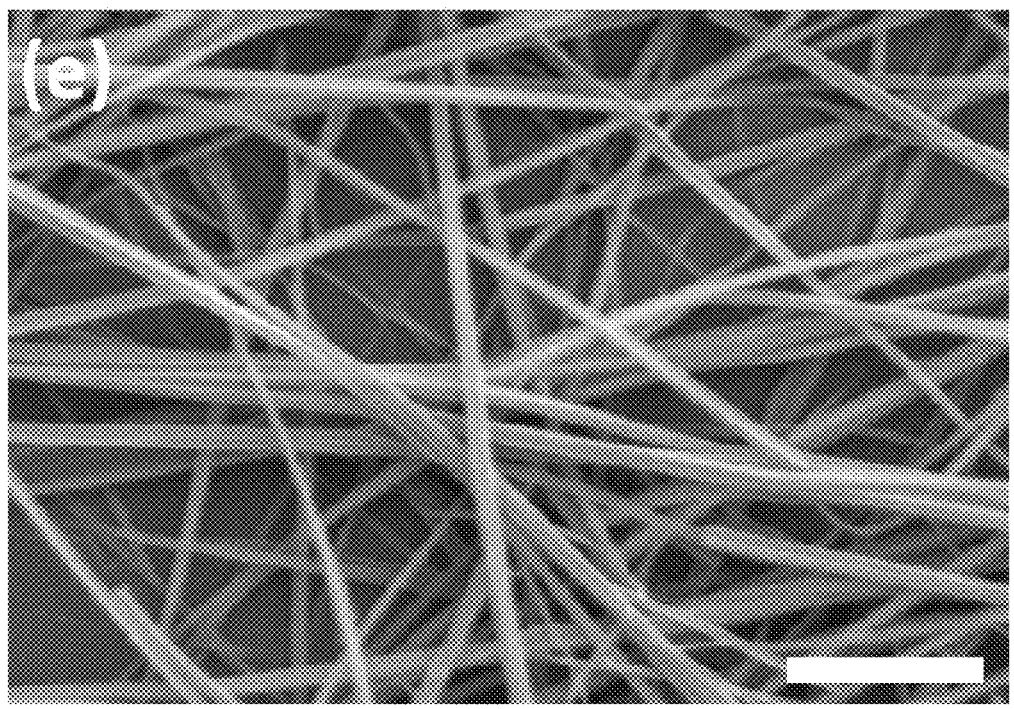
FIG. 4E is an SEM image of PTCDI-PE nanofibers. Scale bar=5 μm.

Nanofibers comprised of PTCDI-DD, PTCDI-C6 and PTCDI-PE, with SEM images shown in FIGS. 4A, 4C, and 4E, respectively, were fabricated via a previously reported solution-based self-assembly method. These nanofibers are tens of micrometers long and hundreds of nanometers wide. They appear to be rigid structures without significant bending or intertwining (also see the optical microscopy images in Supplementary FIGS. 4B, 4D, and 4F for the morphologies). The one dimension growth of these fibril structures results from the strong π-π stacking interaction between PTCDI molecules along the long axial direction, which is dominant over the relatively weak interaction in the lateral direction. The extended π-π stacking results in effective π-electron delocalization, which in turn leads to enhanced charge migration along the nanofiber's backbone. The end-substituted groups (here -DD, -C6 and -PE) comprise the surface of the PTCDI nanofibers. In comparison, the nanofibers assembled from ACTC molecules are much thinner. These nanofibers are several micrometers long and tens of nanometers wide. They twist and merge to form a spatial network with nanometer size porosity, which make the ACTC nanofibers relatively soft and fluffy, which ensures the ease of the D-A distance changing after alkane adsorption. Meanwhile, the much smaller size of the ACTC fibers is conducive to constructing a large area D-A interface area by allowing more ACTC fibers to attach to the surface of the PTCDI fiber. A large D-A interface can be beneficial for efficient photo-induced charge separation.

Figure 4F:
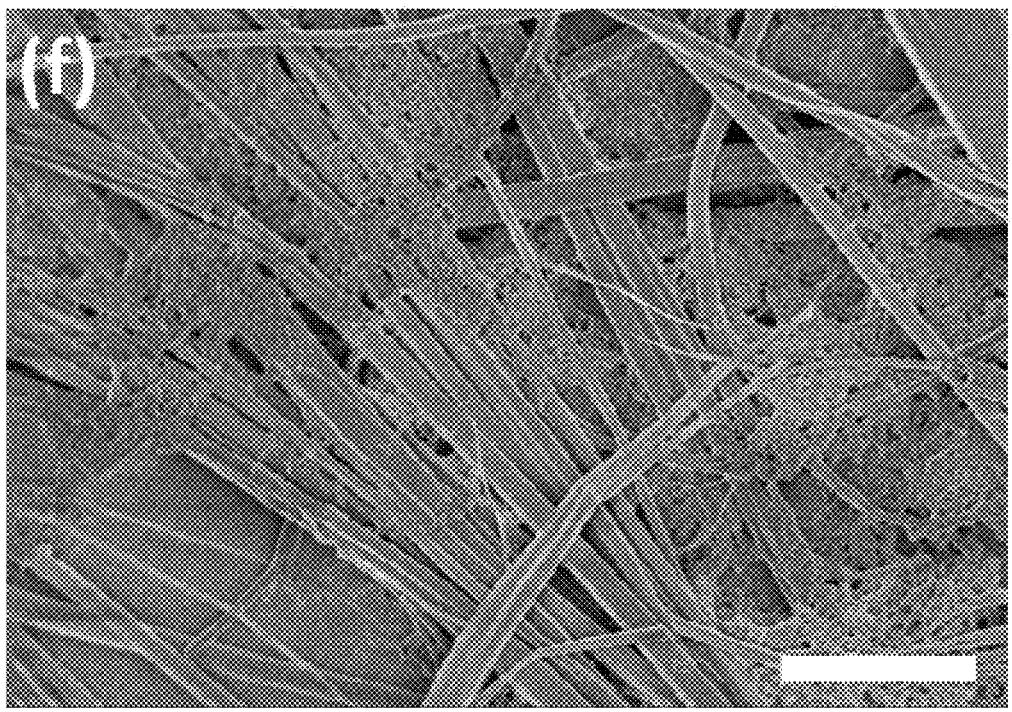
FIG. 4F is an SEM image of ACTC/PTCDI-PE nanofibril composite. Scale bar=5 μm.

By co-assembling PTCDI and ACTC molecules in an appropriate solvent, nanofibril composites with varying interfacial contact were obtained between the two nanofibers depending on the side group structures. In these composites, the ACTC and PTCDI nanofibers maintained similar morphologies as when they are fabricated separately. In the ACTC/PTCDI-DD composite, the ACTC nanofibers were homogenously spread over the much larger PTCDI fibers, forming a continuous nanofibril network (porous film). The composite film possessed few gaps and cracks as shown in the large-area SEM image (FIG. 4B). The good dispersion between the two nanofibers is primarily due to the hydrophobic interdigitation between the long alkyl chains of ACTC and PTCDI-DD. Such a composite is considered to be a cooperative self-assembly rather than a simple self-sorting. Additionally, the alkyl chains dictate the separation distance between the donor and acceptor molecules, which impacts the charge transfer efficiency. In contrast to the ACTC/PTCDI-DD, the ACTC/PTCDI-C6 film showed less uniformity, indicating relatively poor interfacial contact between ACTC and PTCDI-C6 nanofibers (FIG. 4D). This is attributed to the weaker attraction between linear alkyl chains and cyclohexyl groups. The ACTC/PTCDI-PE film showed little interfacial contact as shown in FIG. 4F. In fact, the two materials show an almost complete phase separation owing to the hydrophilic propoxyethyl chains of PTCDI-PE. This same trend is observed using bright field optical microscopy. On the other hand, it was confirmed from the absorption spectra of the ACTC nanofibers, the PTCDI nanofibers, and the composites that no charge transfer band is observed in the longer wavelength range, which typically indicates the formation of a steady-state charge transfer complex. Similar SEM micrographs are illustrated in FIGS. 6A-6B and FIGS. 7A-7F.

Figure 12A:
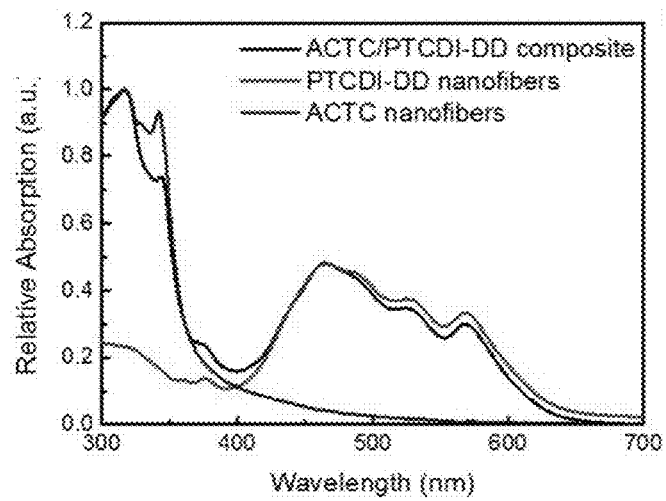
FIG. 12A through 12C shows the relative absorption for example ACTC nanofibers, PTCDI nanofibers, and ACTC/PTCDI nanofiber composites dispersed in ethanol.
Figure 12B:
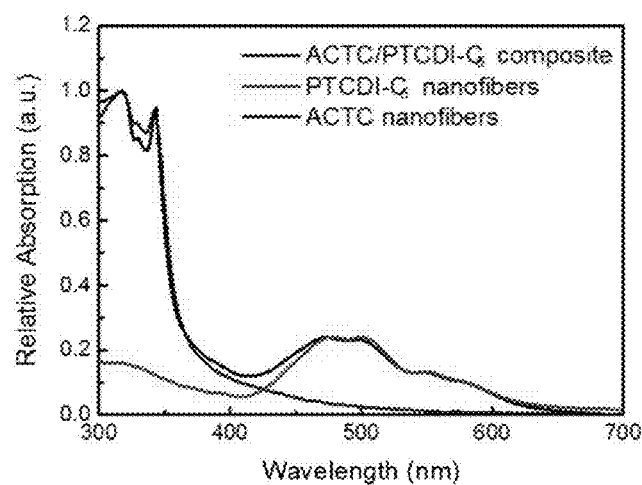
Figure 12C:
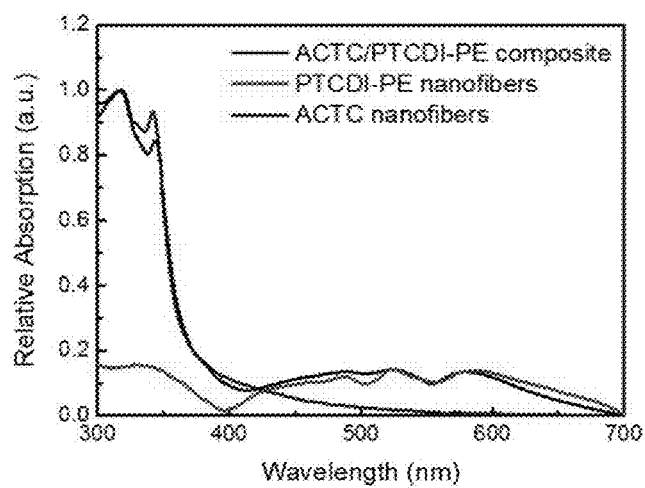
Figure 13A:
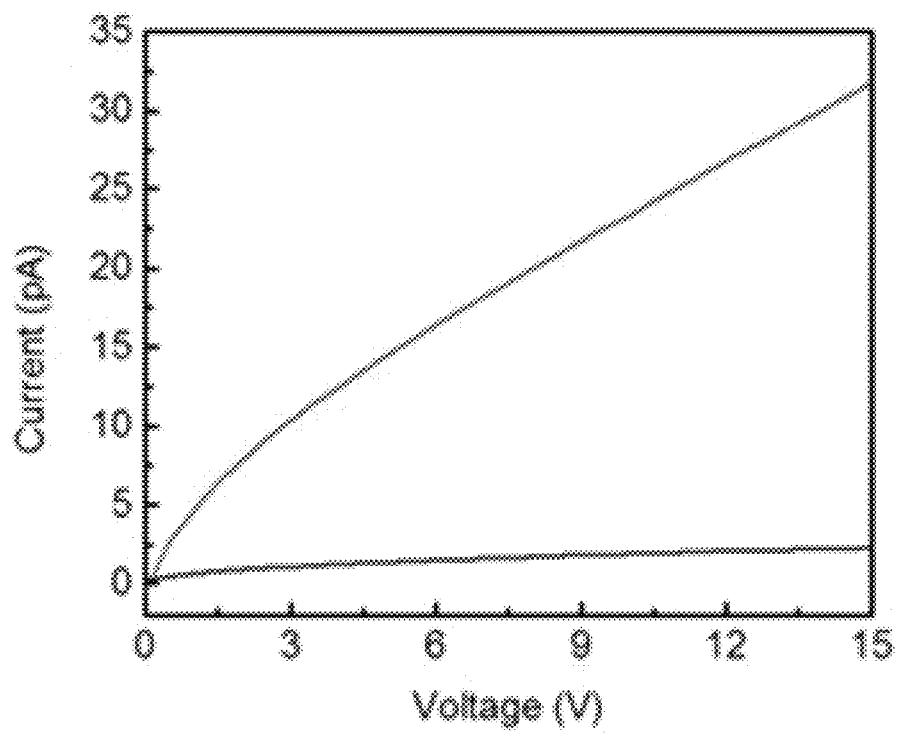
FIG. 13A through 13G are graphs of dark currents (lower) and photocurrents (upper) of ACTC nanofibers, PTCDI nanofibers, and three ACTC/PTCDI composites. The dark current and photocurrent in a typical device of (FIG. 13A) PTCDI-DD nanofibers, (FIG. 13B) ACTC/PTCDI-DD composite (ACTC:PTCDI-DD mole ratio is 1:2), (FIG. 13C) PTCDI-$C_6$ nanofibers, (FIG. 13D) ACTC/PTCDI-$C_6$ composite (ACTC:PTCDI-$C_6$ mole ratio is 1:3), (FIG. 13E) PTCDI-PE nanofibers, (FIG. 13F) ACTC/PTCDI-PE composite (ACTC:PTCDI-PE mole ratio is 1:2), and (FIG. 13G) ACTC nanofibers.
Figure 13B:
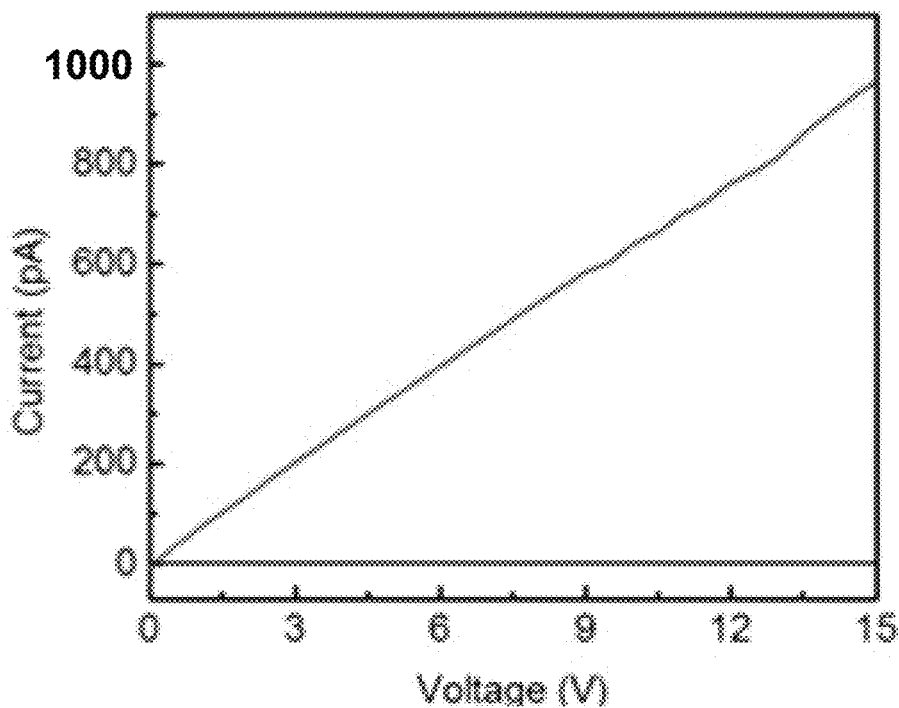
Figure 13C:
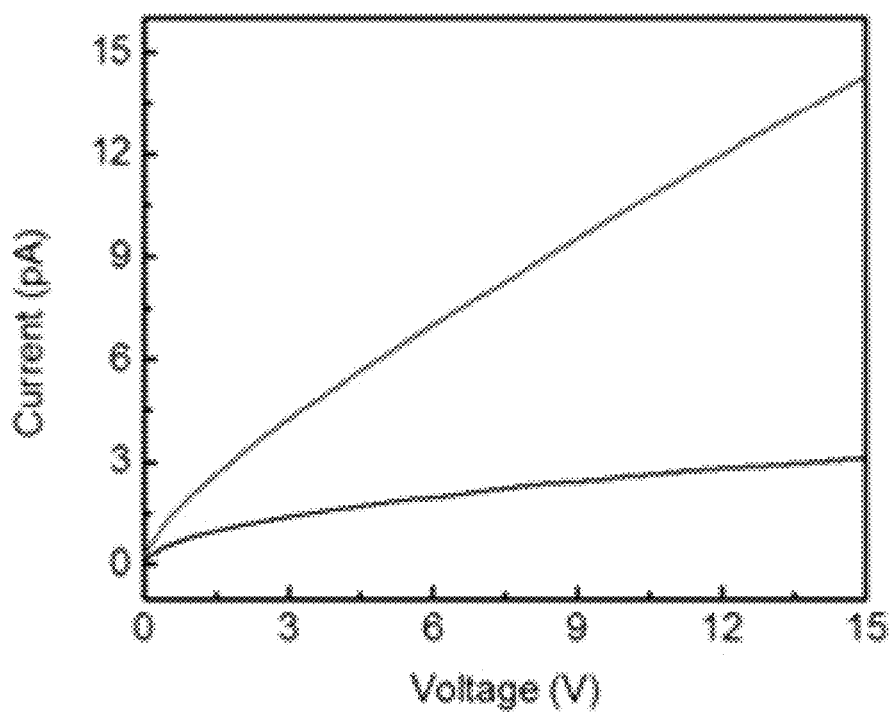
Figure 13D:
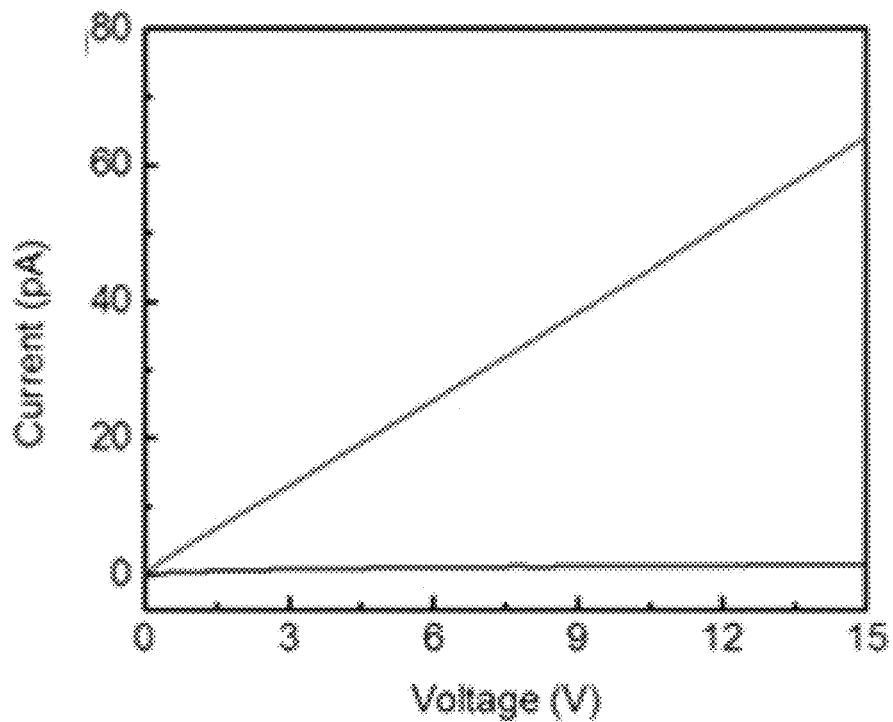
Figure 13E:
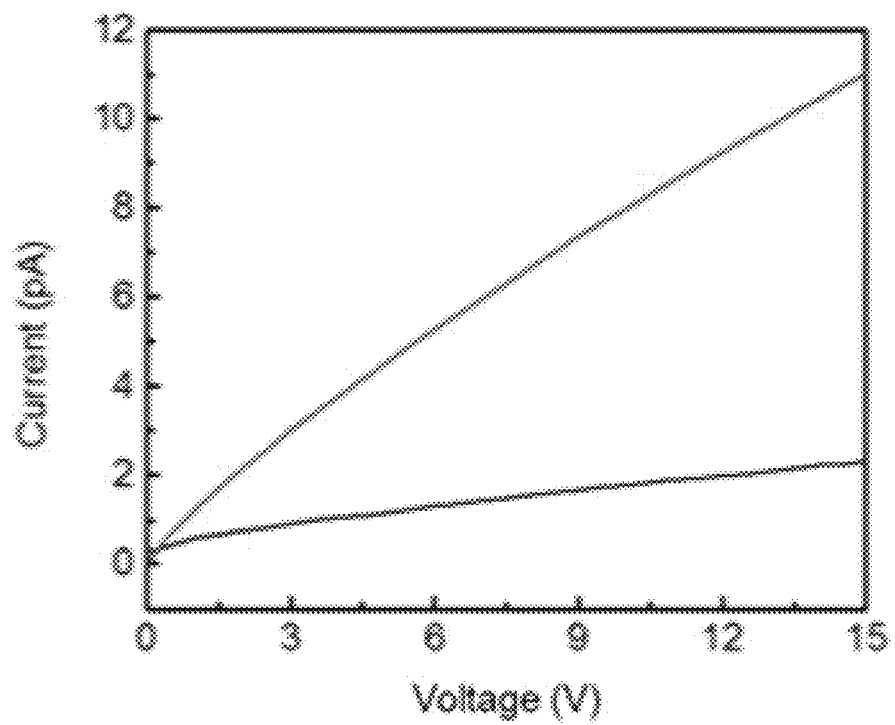
Figure 13F:
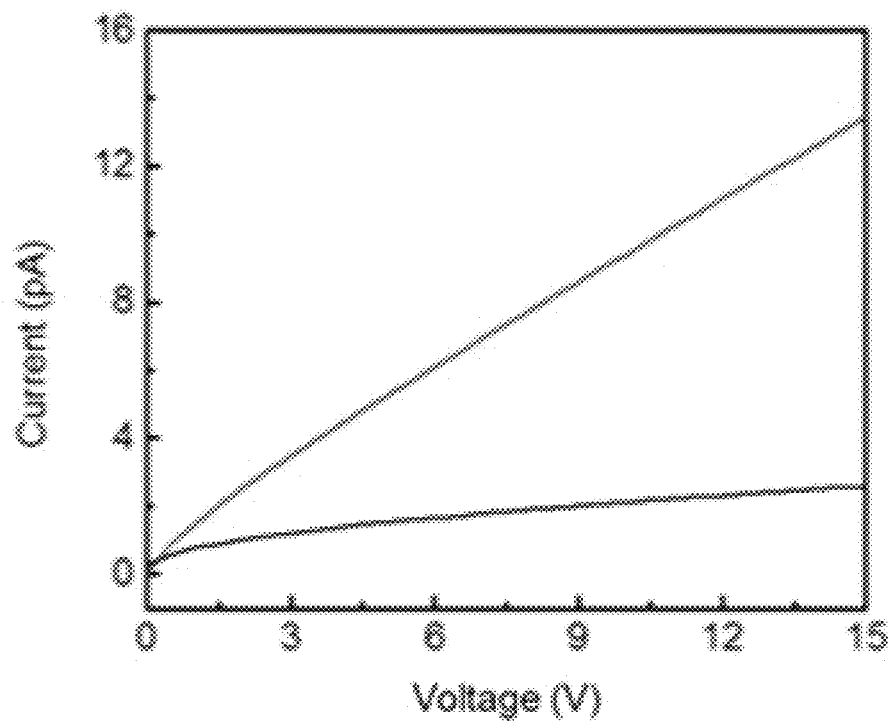
Figure 13G:
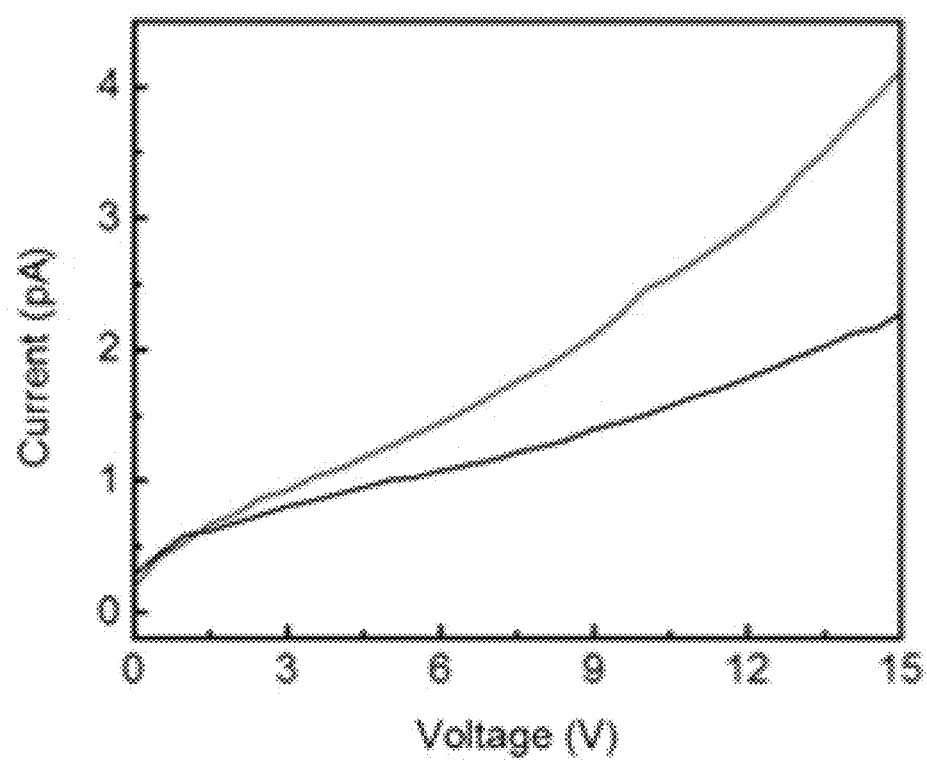
Figure 14:
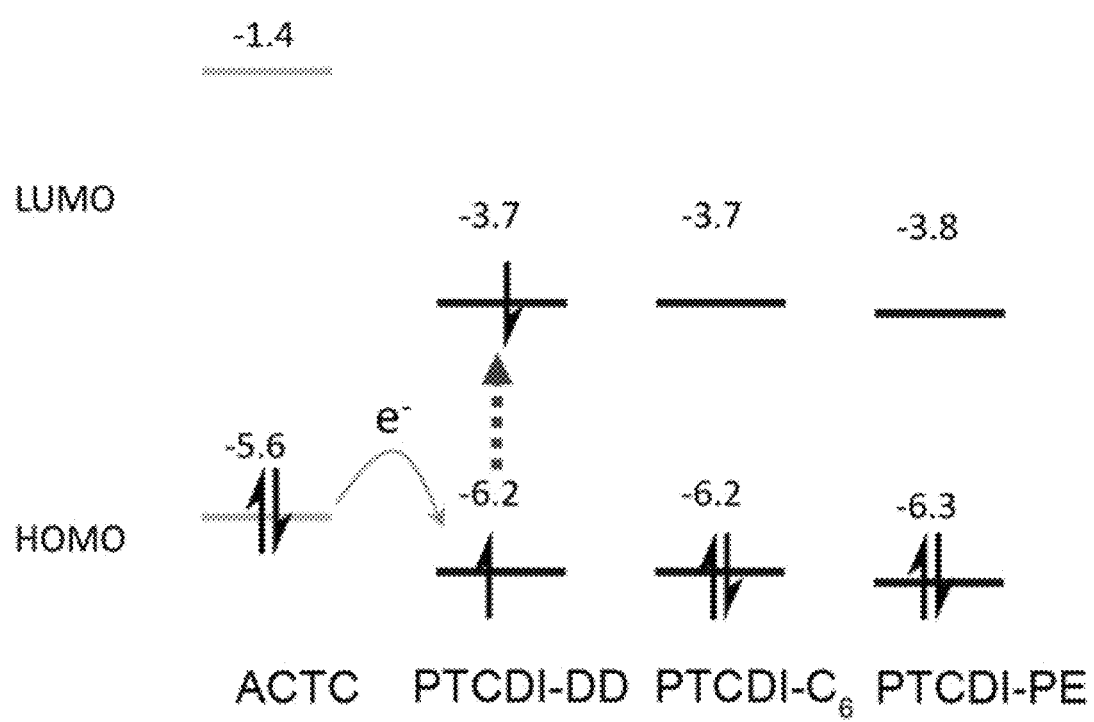
FIG. 14 depicts calculated energy levels for PTCDI-DD, PTCDI-$C_6$, PTCDI-PE, and ACTC. Geometry optimization and energy calculation were performed with density-functional theory (B3LYP/6-31g*) using the Gaussian 03 package. The red dotted arrow indicates the initial excitation of PTCDI-DD molecules. After that, the charge transfer, indicated by the green curved arrow, from the highest occupied molecular orbital (HOMO) of the ACTC to the HOMO of the PTCDI-DD. The calculated energy levels of ACTC and the three PTCDI molecules indicate the similar favorability (driving force) of the PCT process. Because the absorption of ACTC nanofibers is limited to the ultraviolet range, the main PCT process under visible light irradiation is from the HOMO of the ACTC to the HOMO of the PTCDI core. Although all three PTCDIs have very similar HOMO and LUMO levels, the values of photocurrent enhancement ($I_{photo}/I_{dark}$ in each device) in the three composites are quite different due to the different D-A interface as discussed in the context.
Figure 15A:
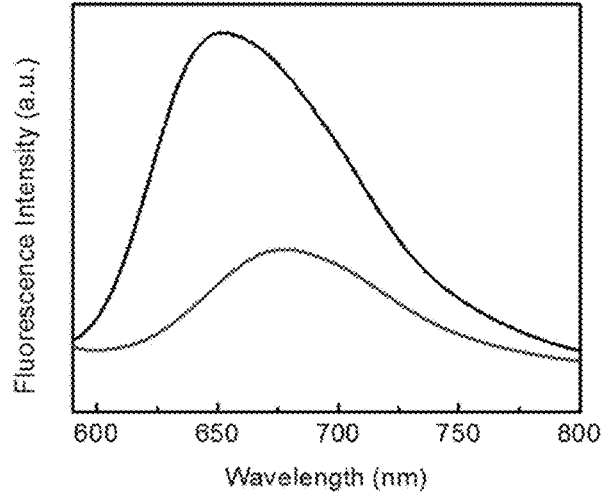
FIG. 15A-15C are graphs showing fluorescence quenching of PTCDI in example ACTC/PTCDI composites. The fluorescence spectra of these composites are shown as red (lower) curves and the fluorescence spectra of the corresponding pure PTCDI nanofibers are shown as black (upper) curves. The fluorescence spectra of (FIG. 15A) the PTCDI-DD nanofibers and the ACTC/PTCDI-DD composite (ACTC:PTCDI-DD mole ratio is 1:2), (FIG. 15B) the PTCDI-C6 nanofibers and the ACTC/PTCDI-C6 composite (ACTC:PTCDI-C6 mole ratio is 1:3), and (FIG. 15C) the PTCDI-PE nanofibers and the ACTC/PTCDI-PE composite (ACTC:PTCDI-PE mole ratio is 1:2). In each case, 1 mL of the quasi-uniform mixtures of PTCDI nanofibers were transferred to transparent glass slides, which have 1 cm×1 cm of exposure area masked by the Scotch tape. Based on the ratio of ACTC to PTCDI in each composite, different amounts of mixture were deposited to maintain the same molar amount of PTCDI in each slide. The slides were left in a vacuum oven to dry at room temperature. Then the Scotch tape was removed from the glass slide.
Figure 15B:
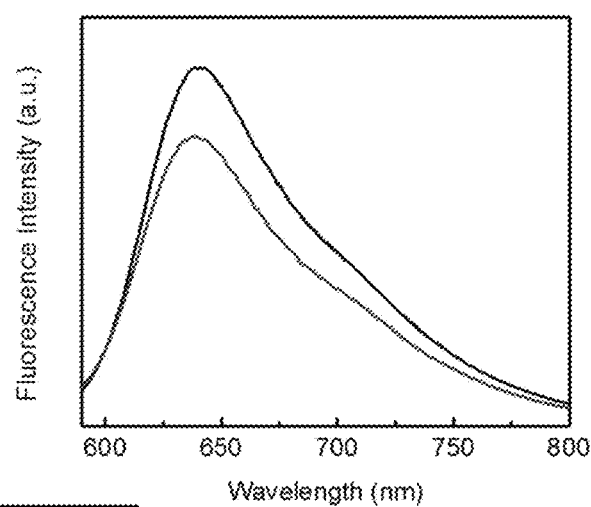
Figure 15C:
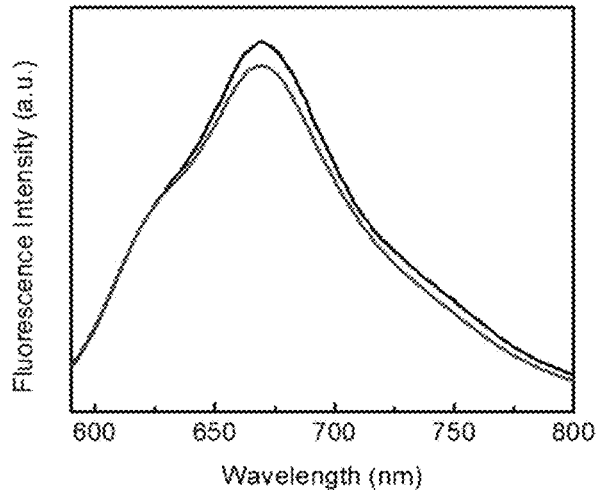
Figure 16:
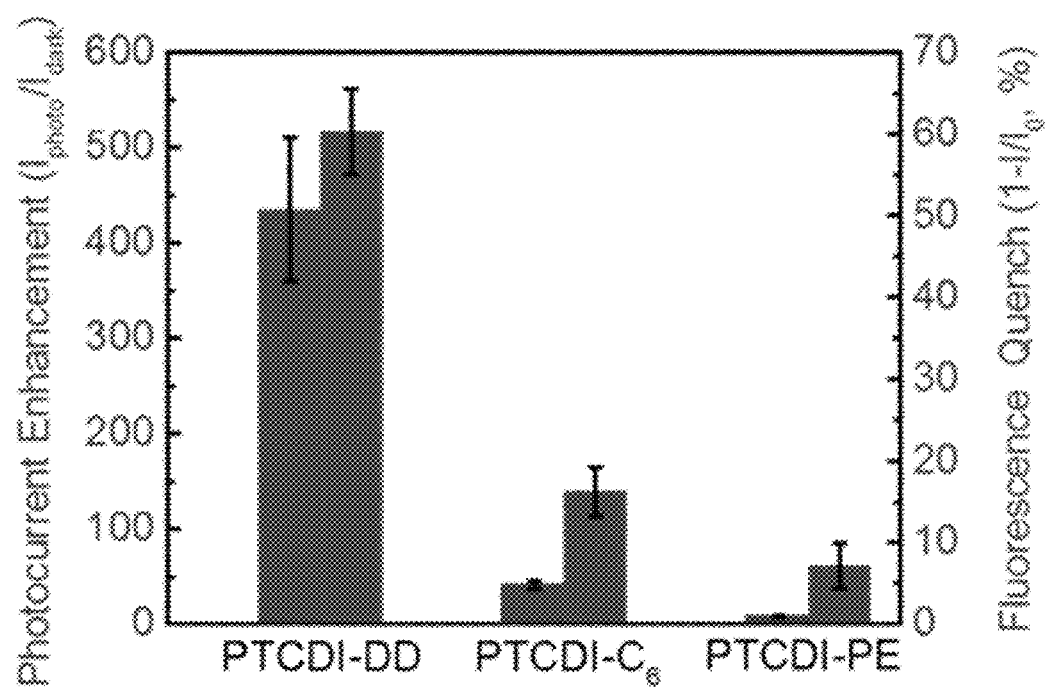
FIG. 16 is a bar comparison graph of fluorescence quenching and photocurrent enhancement for three ACTC/PTCDI composites. The red (left) and green (right) columns denote photocurrent enhancement and yield of fluorescence quenching, respectively. The molar ratio of ACTC:PTCDI used in the three nanofiber composites are 1:2, 1:3, and 1:2 for ACTC/PTCDI-DD, ACTC/PTCDI-$C_6$ and ACTC/PTCDI-PE, respectively.

FIGS. 12A-12C illustrate the relative absorption for example ACTC nanofibers, PTCDI nanofibers, and ACTC/PTCDI nanofiber composites dispersed in ethanol. 2 ml of ethanol was added to 1 mL of the original quasi-uniform mixture of PTCDI nanofibers, ACTC nanofibers, or ACTC/PTCDI 1:1 composites while shaking. The mixtures were transferred to a quartz cuvette and measured with an Agilent Cary 100 series UV-Vis spectrophotometer. The spectra of ACTC/PTCDI composite and ACTC nanofibers were normalized to 1. FIG. 12A illustrates the relative absorption of the ACTC nanofibers, PTCDI-DD nanofibers, and ACTC/PTCDI-DD composite. FIG. 12B illustrates the relative absorption of the ACTC nanofibers, PTCDI-$C_6$ nanofibers, and ACTC/PTCDI-$C_6$ composite. FIG. 12C illustrates the relative absorption of the ACTC nanofibers, PTCDI-PE nanofibers, and ACTC/PTCDI-PE composite. The highest peaks are located at around 320 nm, indicating the similar stacking mode of the pure ACTC nanofibers and the ACTC/PTCDI composite. The spectra of PTCDI nanofibers were normalized and their maxima peak values were set to the same values as the first peak of the PTCDI in the ACTC/PTCDI composites for ease of comparison.

Figure 5A:
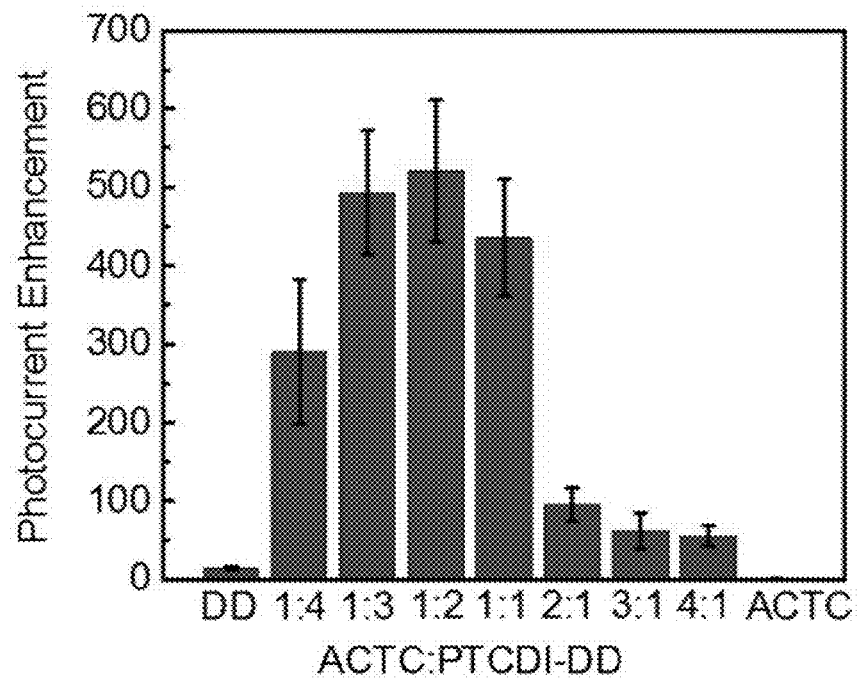
FIGS. 5A, 5B and 5C are graph showing the statistical photocurrent enhancement (Iphoto/Idark) measured for three example nanofibril composites, (A) ACTC/PTCDI-DD, (B) ACTC/PTCDI-$C_6$, and (C) ACTC/PTCDI-PE, depending on the molar ratio of ACTC to PTCDI in the precursor solutions used to fabricate the nanofibril composite through a one-step solution processing.
Figure 5B:
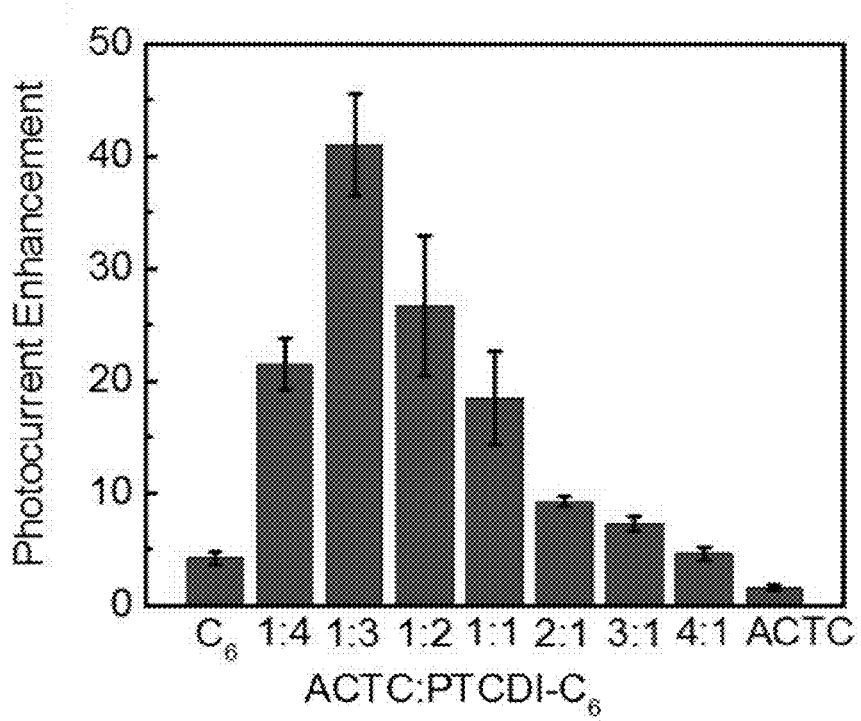
Figure 5C:
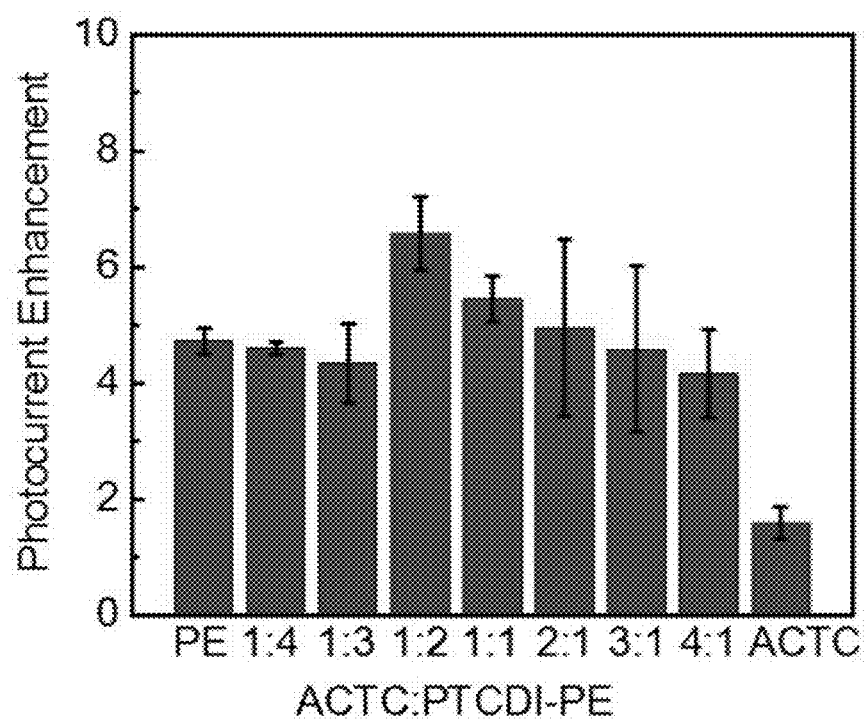
Figure 6A:
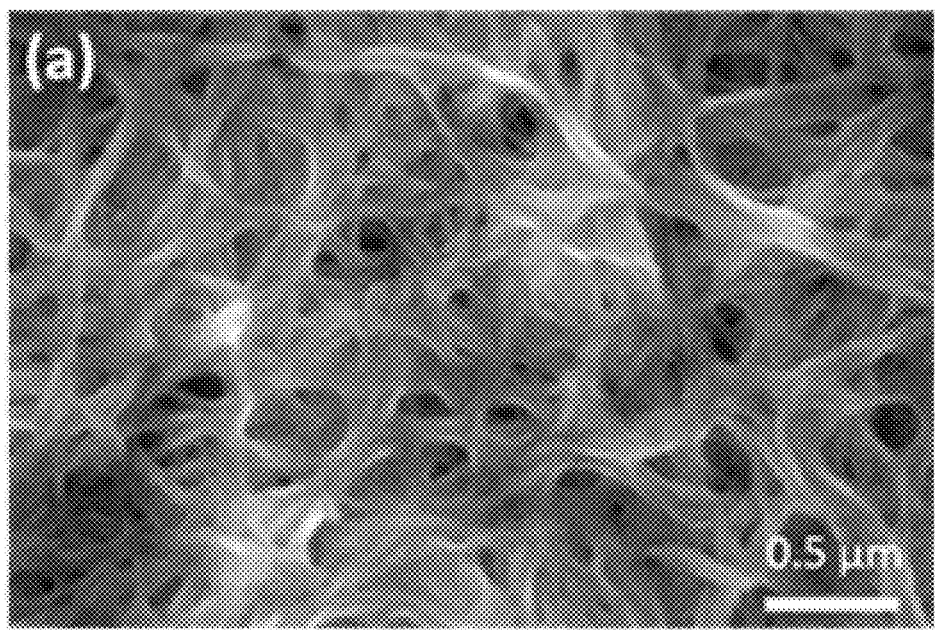
FIGS. 6A and 6B shows SEM images of ACTC nanofibers formed in one example.
Figure 6B:
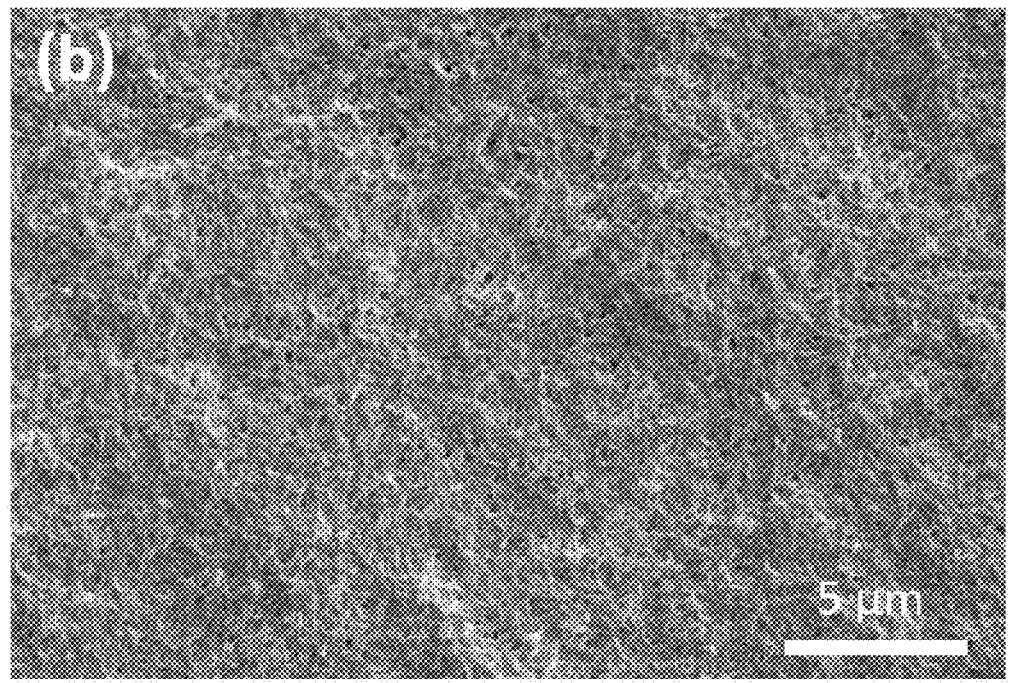
Figure 7A:
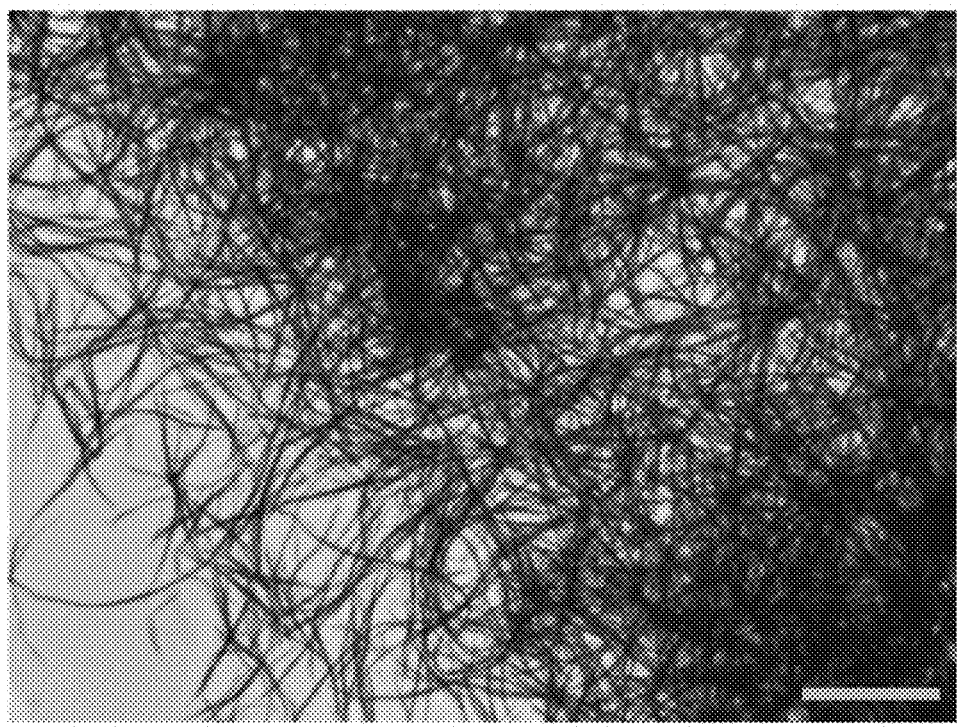
FIG. 7A-7F are images which show morphology comparison between PTCDI nanofibers and corresponding composites (ACTC:PTCDI=1:1). Transmission optical microscopy images of the PTCDI-DD nanofibers in FIG. 7A and the ACTC/PTCDI-DD nanofibril composite in FIG. 7B.
Figure 7B:
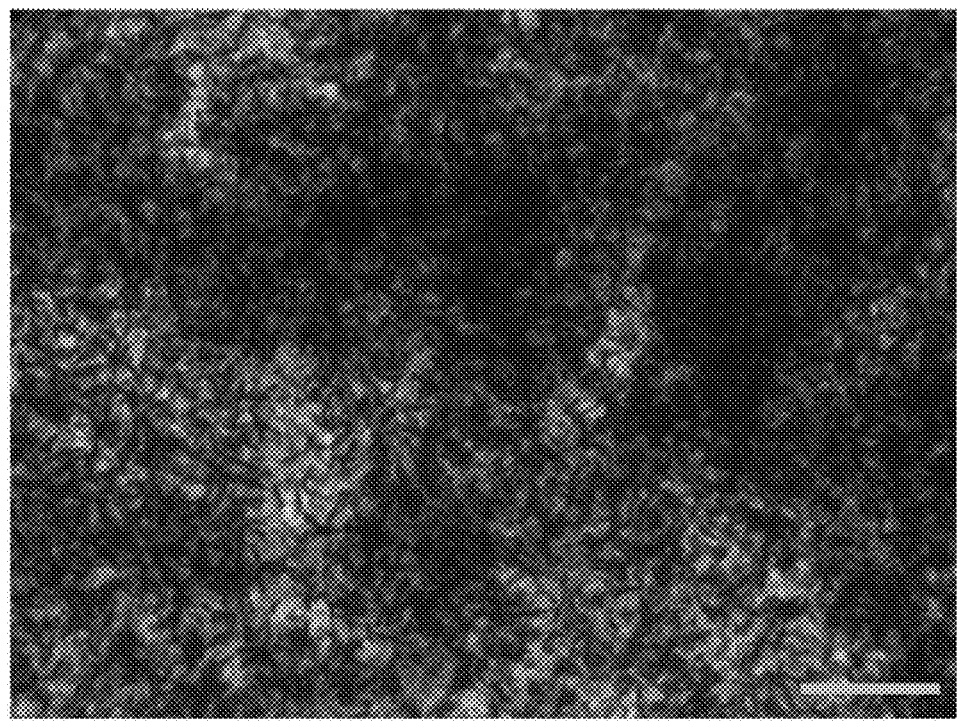
Figure 7C:
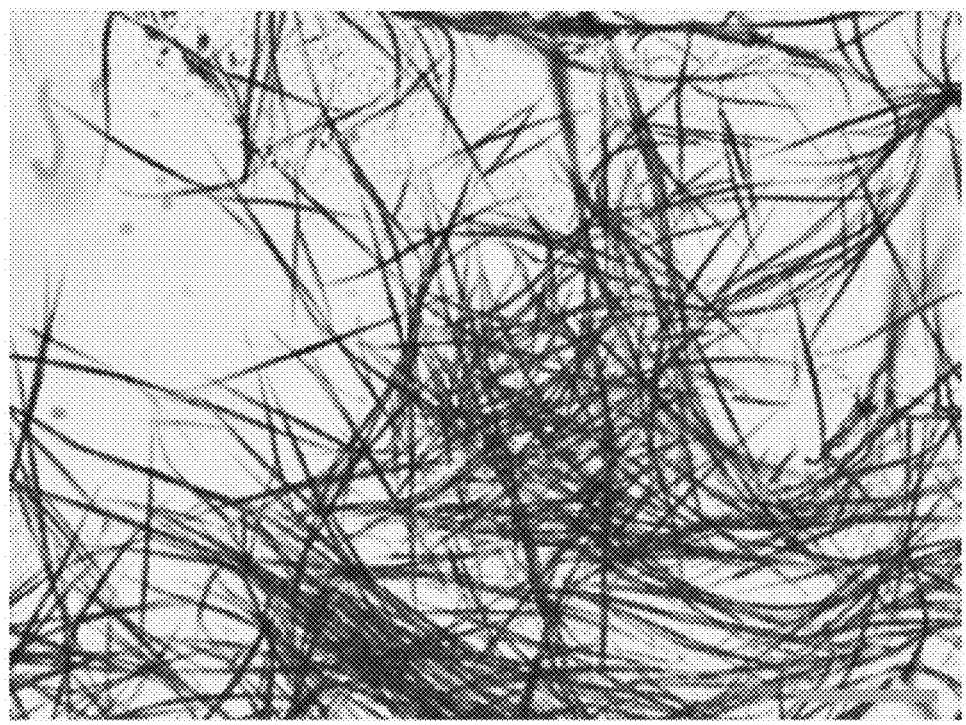
Figure 7D:
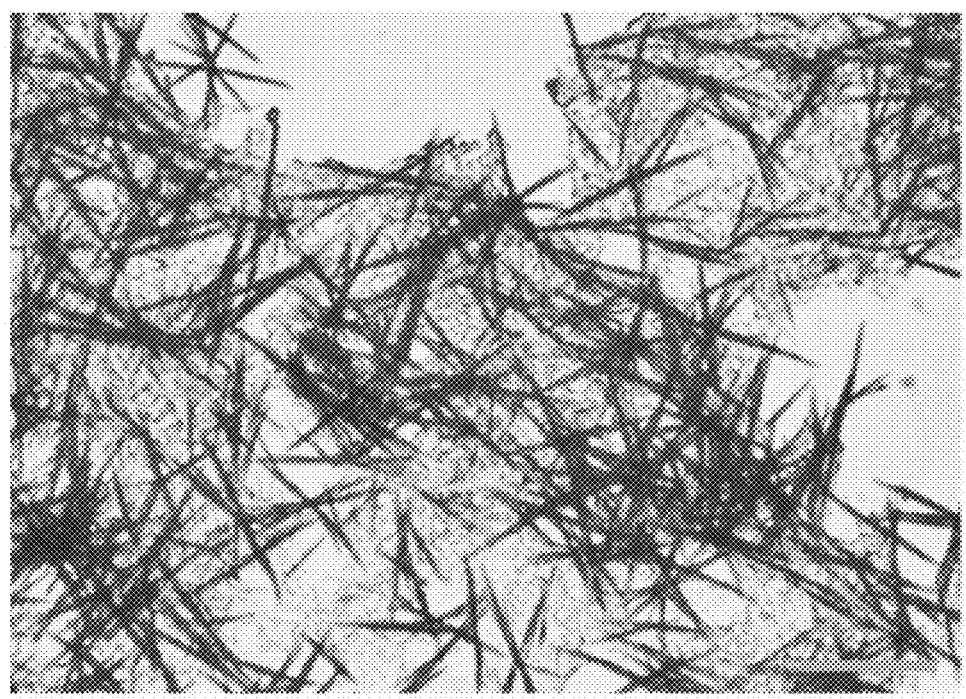
Figure 7E:
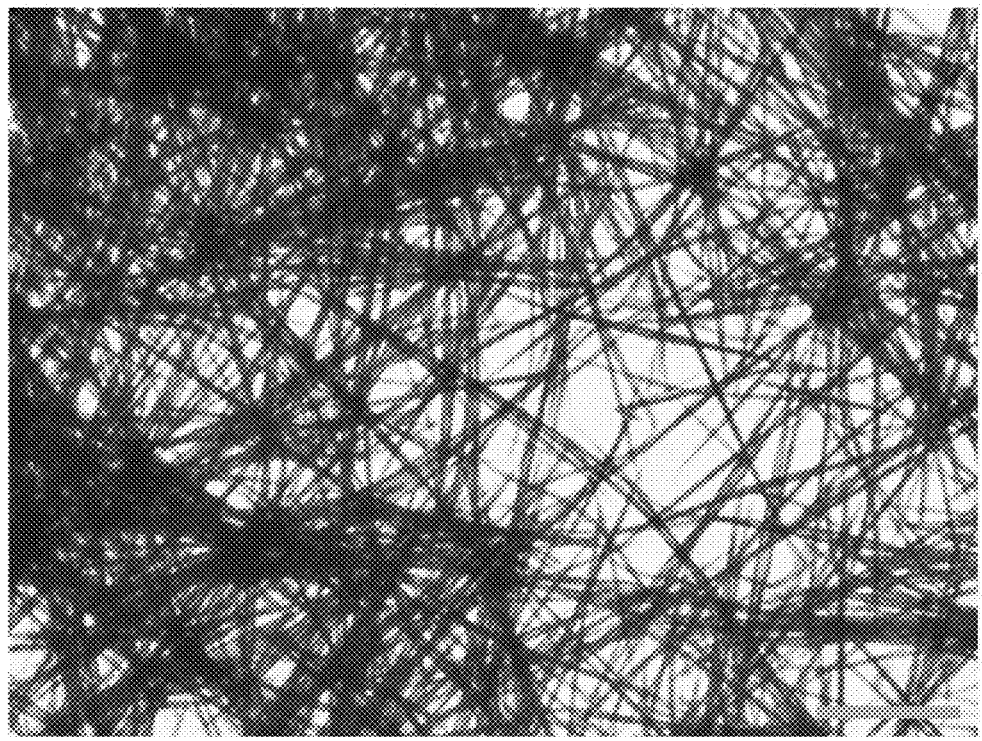
Figure 7F:
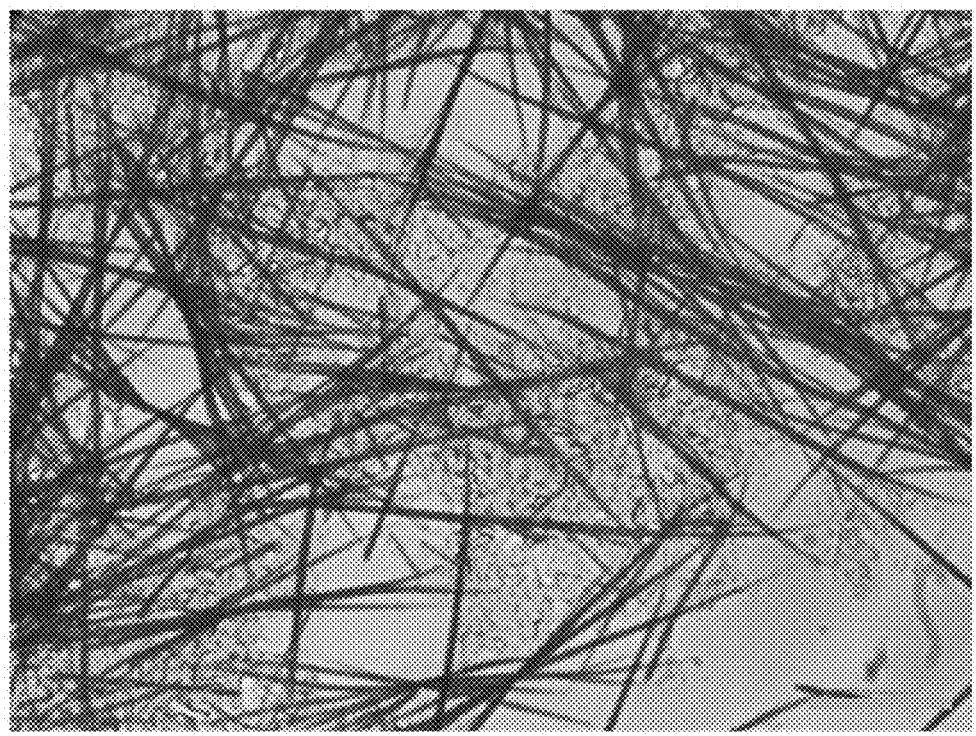

To study the maximum photoconductivity in the three composites, an evaluation of the dependence of the photocurrent enhancement (defined as the ratio of the current under illumination to the current in the dark for each device, Iphoto/Idark) on the molar ratio of ACTC to PTCDI in the precursor solutions used to fabricate the composite was performed (see FIGS. 5A-5C). All I-V curves of the composites display approximately linear behavior, indicating that the density of trap states is low. Although the calculated energy levels of ACTC and PTCDIs indicate an energy-favorable PCT process in all three composites (see FIGS. 13A-13G), the maximum enhancement is quite different over the composites due to the different D-A interface. The ACTC/PTCDI-DD and ACTC/PTCDI-C6 composites show a clear maximum photocurrent enhancement. Increasing the amount of ACTC nanofibers present increases the D-A interfacial area and, thus, enhances the photocurrent. On the other hand, too much ACTC, which is highly resistive, blocks the percolation pathways, hindering current. Thus, optimal ratios for both these films were observed. The ACTC/PTCDI-DD film showed an enhancement one order of magnitude larger than the ACTC/PTCDI-C6 composite. This is attributed to the improved interfacial contact as observed during the morphology study. By contrast, the photocurrent enhancement of the ACTC/PTCDI-PE composite is similar to the pristine PTCDI-PE and showed a negligible dependence on molar ratio due to the lack of interfacial contact between the two materials. The photocurrent enhancement data correlate well with the yields of fluorescence quenching in the three composites (see FIGS. 15A-15C and FIG. 16), which indicates that the enhancement indeed arises from the high PCT efficiency.

Sensing Performance Comparison Among the ACTC/PTCDI Composites.

Figure 8:
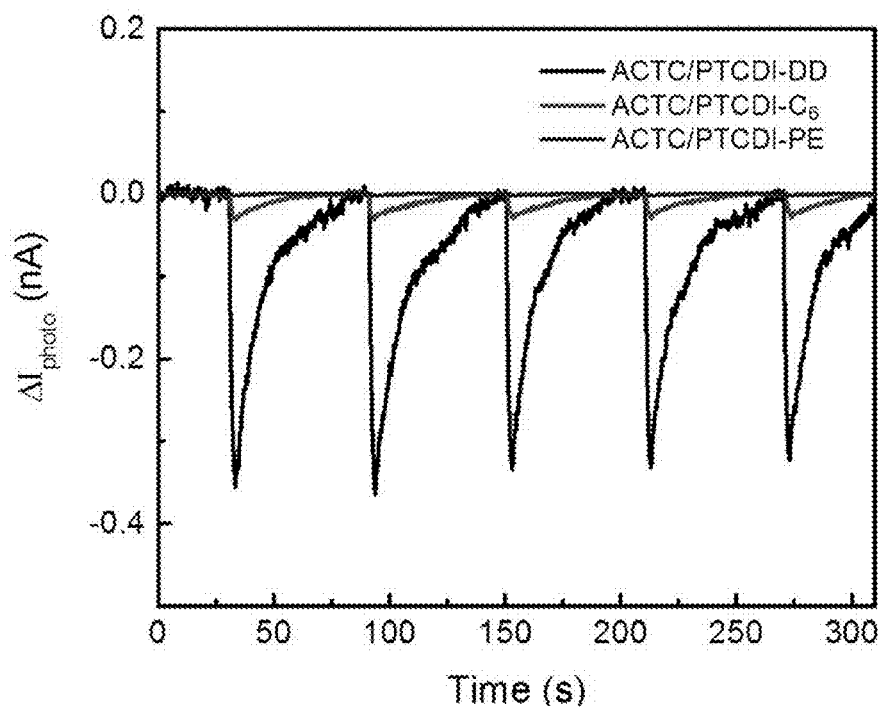
FIG. 8 is a graph of sensor performance comparison among three ACTC/PTCDI composites. Photocurrent changes ($\Delta I_{photo}$) (baseline corrected) of the three nanofibril composites as marked in the figure were measured as a function of the elapsed time upon exposure to saturated n-dodecane vapor at room temperature.

The porous and compatible D-A interface is beneficial for alkane detection. The favorable adsorption of alkanes at the interface results in an increased D-A distance, which is evidenced as a decrease in photocurrent. To verify this mechanism, the photocurrent responses of the three ACTC/PTCDI composites (at their optimal ACTC to PTCDI ratios) were compared upon the exposure to a saturated vapor of n-dodecane at room temperature. A rapid decrease in photocurrent was observed upon exposure, followed by a relatively slow recovery after removing the analyte source for all the three ACTC/PTCDI composites (see FIG. 8). However, the amplitudes of the responses for the three composites are quite different. The photocurrent change of ACTC/PTCDI-DD is over ten times greater than ACTC/PTCDI-C6 and two hundred times greater than ACTC/PTCDI-PE. These results correlate closely with the PCT efficiencies that were estimated above using the photocurrent measurements. This is in line with expectations as both of these phenomena share a common origin, the D-A interface. As designed, the donor and acceptor fibers are interconnected by flexible alkyl chains in the ACTC/PTCDI-DD composite. As the interface and the alkane analytes have similar properties one would expect a higher local concentration of alkanes at the interface. The flexibility of the alkyl chains at the interface provides freedom of movement for the D-A distance upon the adsorption and diffusion of alkane molecules at the interface. Although this movement is in the sub-molecular distance range, it is enough to sufficiently interfere with the PCT efficiency. In ACTC/PTCDI-C6, the PCT efficiency is moderate due to the partially formed D-A interface, and its response, as expected is moderate. In the case of ACTC/PTCDI-PE, the lack of an alkyl-compatible D-A interface results in the lowest response, even though the phase separated ACTC nanofibers in the ACTC/PTCDI-PE composite still adsorb alkane molecules themselves. Whereas, without the efficient PCT process, the observation of a photocurrent response to alkane vapors would be difficult. Additionally, the large photocurrent caused by the high PCT efficiency is desired for chemiresistive sensing materials, which may enlarge the potential detectable concentration range and lower the detection limit with an enhanced signal/noise ratio. Consequently, the interface morphology is closely linked to the sensor performance. The ACTC/PTCDI-DD composite shows the largest response to hexane vapor, indicating its higher sensitivity compared to the other composites.

Alkane Vapor Detection and Recognition by the ACTC/PTCDI-DD Composite.

The greater response of the ACTC/PTCDI-DD composite towards alkane vapor is likely due to its porous morphology and more compatible D-A interface, which is able to adsorb alkane molecules, and then to result in the interruption upon the PCT process. To further verify the ACTC/PTCDI-DD composite's sensitivity to alkanes, the composite was also exposed to the saturated vapors of n-octane, n-decane, and n-dodecane in a sequence of increasing carbon atom number. Overall, the composite responded to all of them, and produced similar photocurrent changes for each alkane over five consecutive exposures. The hexane vapor provided about 12% photocurrent reduction, and with the increasing alkane length, less reduction was observed (for example, 6% for saturated dodecane vapor). To further explore the sensitivity, the ACTC/PTCDI-DD composite was exposed to different concentrations of alkane vapors. Generally, as the vapor was diluted, the amplitudes of photocurrent response decreased. When the alkane vapors were diluted to 1% of their saturated concentrations, the responses of the composite were at least seven times larger than the noise level, indicating an even lower limit of detection (LOD) below these concentrations (FIGS. 17A-17D). Furthermore, although the photocurrent generally decreases during exposure and increases during recovery for all alkane vapors, the signals show dramatically different kinetic fingerprints for different alkanes during both the exposure and recovery periods. By utilizing this rich information, the ACTC/PTCDI-DD composite sensor provides the ability to classify different analytes within the series of alkanes.

Figure 9A:
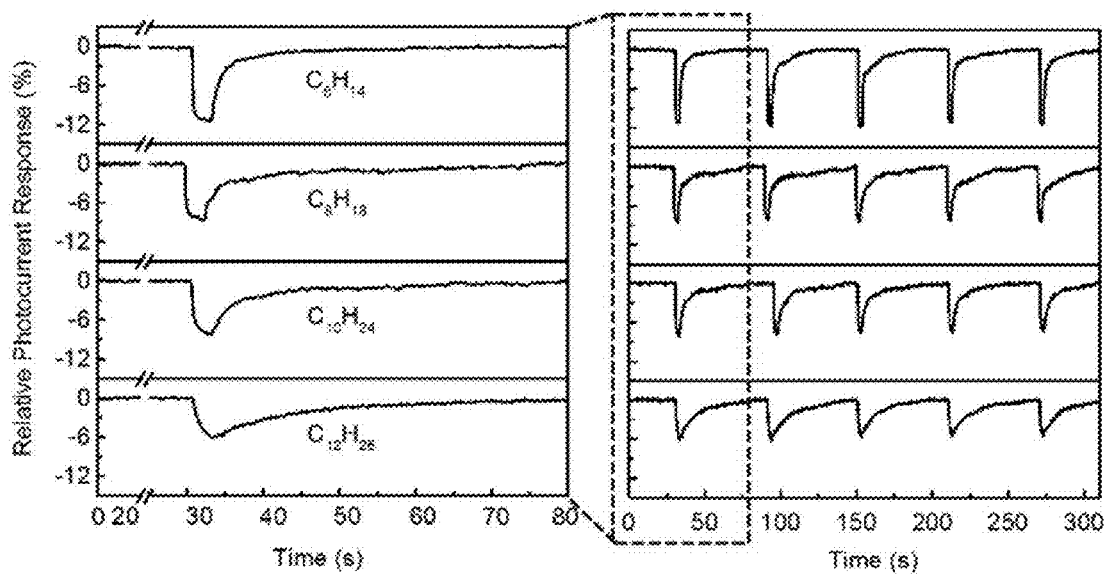
FIG. 9A is a graph showing relative photocurrent response to time curves (baseline corrected) measured at room temperature for saturated vapors of n-hexane ($C_6H_{14}$, $1.6\times10^5$ ppm), n-octane ($C_8H_{18}$, $1.0\times10^4$ ppm), n-decane ($C_{10}H_{22}$, $2.1\times10^3$ ppm), and n-dodecane ($C_{12}H_{26}$, $2.2\times10^2$ ppm); the data were obtained using the ACTC/PTCDI-DD nanofibril composite at an ACTC:PTCDI-DD ratio of 1:2. On the X-axis, time represents the elapsed time in the sensing experiment. The relative photocurrent response is defined as, $(1-I_t/I_0)\times100\%$, where $I_t$ is the photocurrent at time t; $I_0$ is the photocurrent at the time zero (photo current baseline).
Figure 17A:
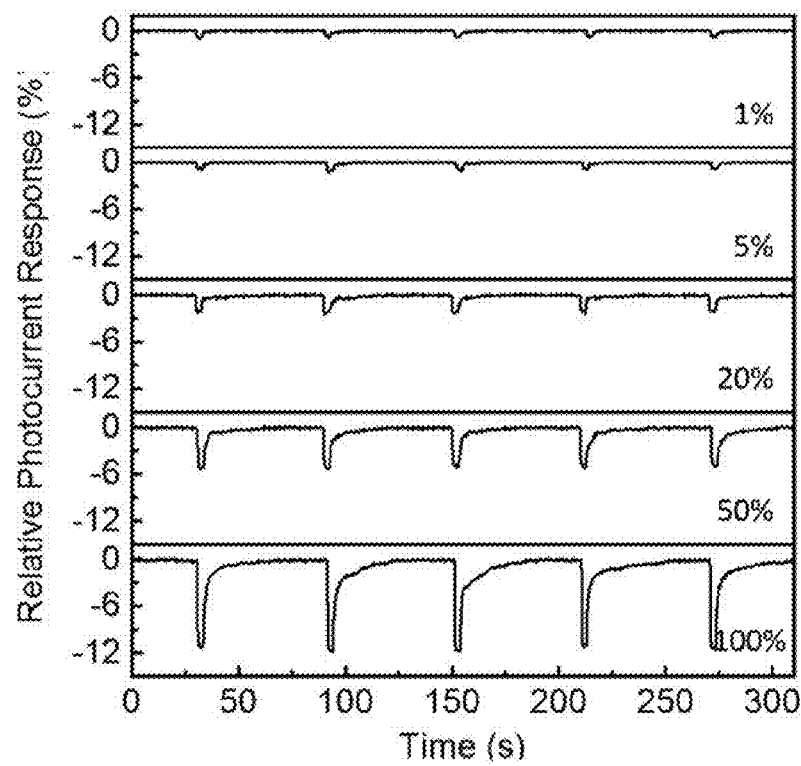
FIG. 17A-17D are graphs of alkane exposures to an ACTC/PTCDI-DD composite to determine the sensor detection limit. The relative photocurrent response (baseline corrected) measured on ACTC/PTCDI-DD composite exposed to 1%, 5%, 20%, 50% and 100% saturated vapor of (FIG. 17A) n-hexane ($C_6H_{14}$), (FIG. 17B) cyclohexane ($C_6H_{12}$), (FIG. 17C) n-octane ($C_8H_{18}$), (FIG. 17D) n-decane ($C_{10}H_{22}$), and n-dodecane ($C_{12}H_{26}$), at room temperature.
Figure 17B:
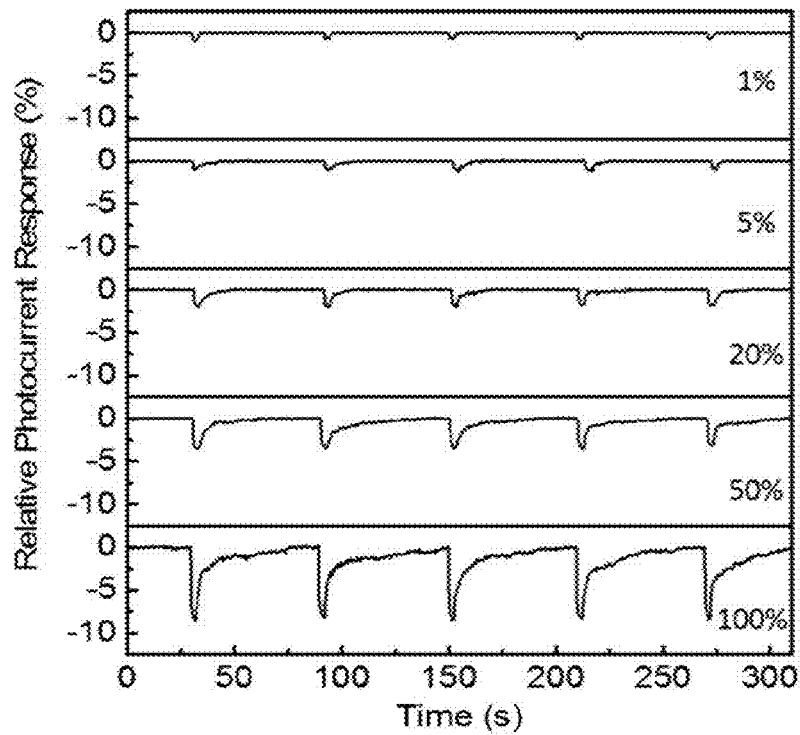
Figure 17C:
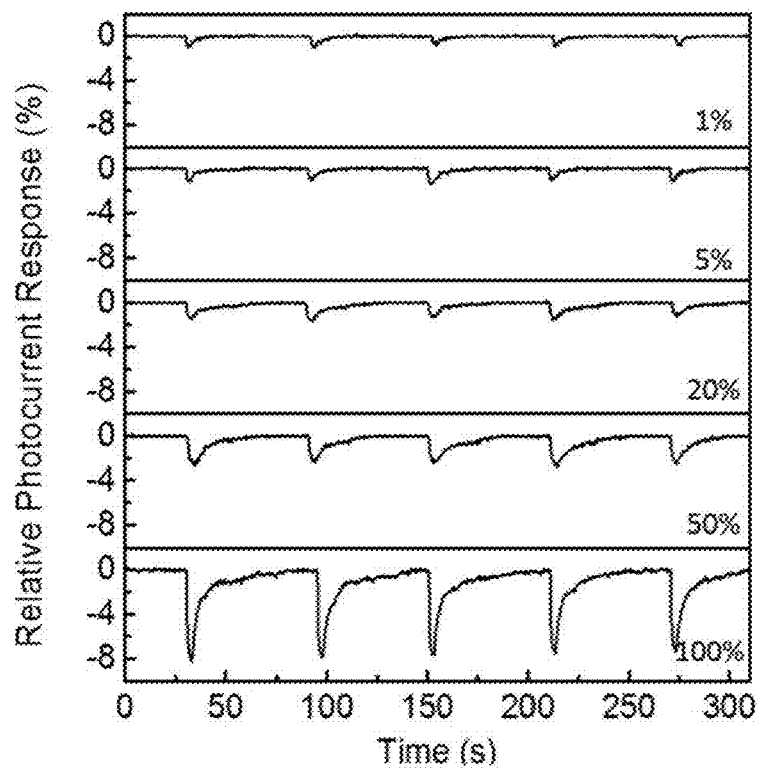
Figure 17D:
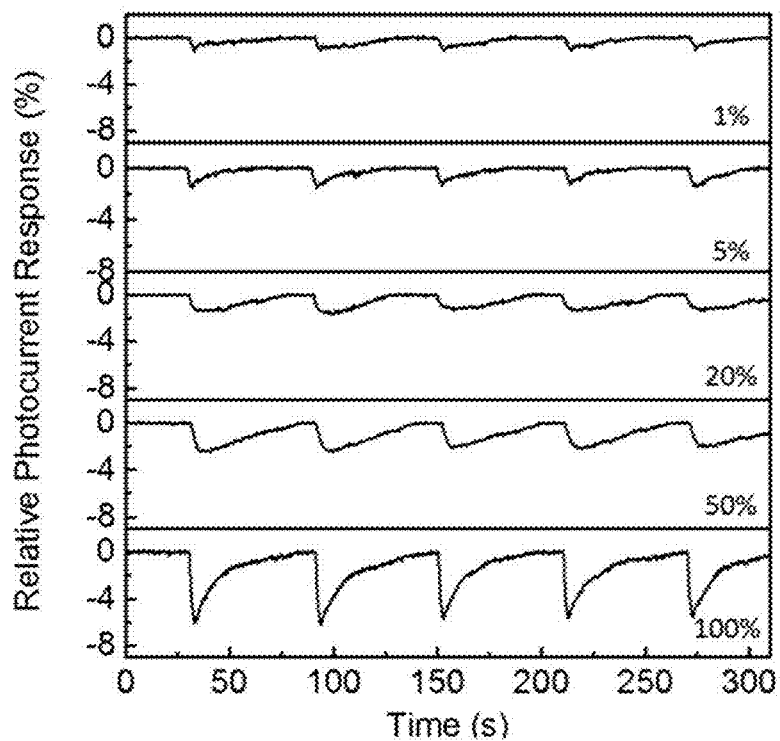
Figure 18A:
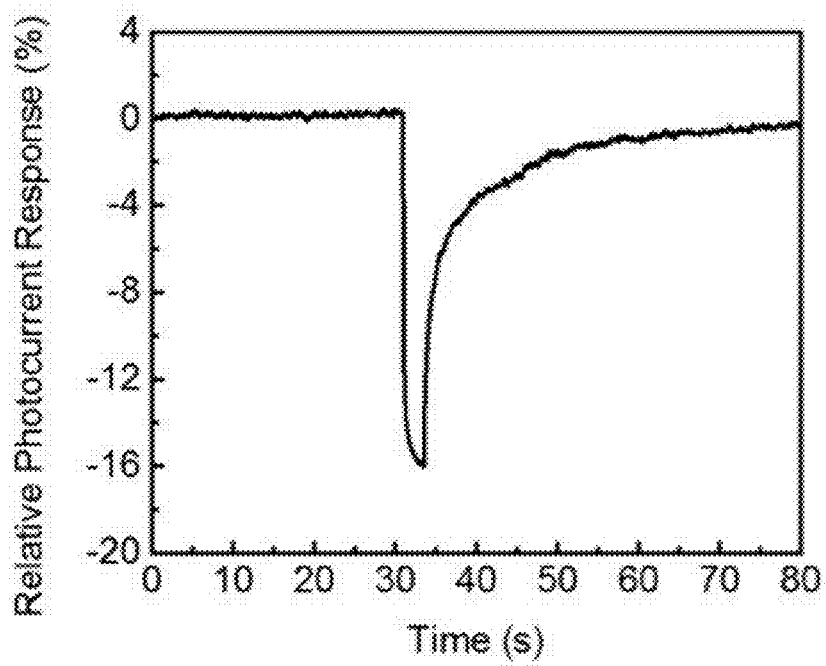
FIGS. 18A and 18B are graphs showing the relative photocurrent response of an ACTC/PTCDI-DD composite to saturated cyclohexane vapor ($1.0\times10^5$ ppm) during (FIG. 18A) one exposure cycle, and (FIG. 18B) the five-cycle test. The ratio of ACTC to PTCDI-DD is 1:2.
Figure 18B:
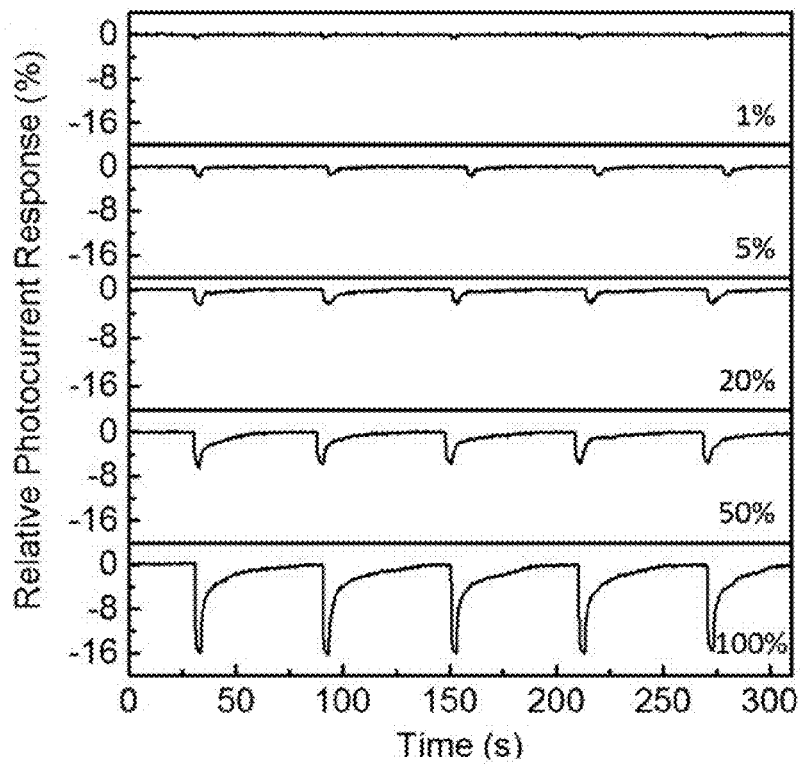

When the sensor was initially exposed to an analyte, the photocurrent of the composite immediately started a rapid decrease (exposure period). This change demonstrates the alkane vapor adsorption by the interdigitated alkyl interface. Easily accessible binding sites are quickly consumed and filled. After this stage, the rates of photocurrent decrease behave differently to each alkane. FIG. 9A shows the relative photocurrent responses to five exposures of the four alkanes, along with the time-magnified curves for the first exposures. For the n-hexane vapor, after the rapid decrease, a stage with relatively stable photocurrent was reached during the exposure. Due to the weak interaction and low molecular weight, the average staying time at the interface is low for short chain alkanes. This stage may imply a quasi-equilibrium state between alkane molecule adsorption and disassociation from the surface. These steady stages gradually disappeared with the increasing length of alkane molecules. In the case of n-dodecane, such stages totally disappeared, due to the stronger interaction with the alkyl interface, which makes the disassociation rate slower than the adsorption rate during the exposure period. The longer staying time may allow larger alkanes to diffuse deeper into ACTC/PTCDI-DD interface. Additionally, because of their larger size, the interruption to the photocurrent should be more effective at the D-A interface. So the larger current decrease observed for n-hexane than the other normal alkanes can be attributed to its higher vapor concentration. Consistently, if all alkanes are produced at the same concentration, the longer alkanes will cause larger photocurrent changes. For example, a saturated vapor of n-dodecane has a similar vapor concentration as the 1% dilution of n-hexane, but the former produces about one magnitude of order higher response than the latter (FIGS. 17A, and 17D). It should also be noted that the analytes are not limited to normal alkanes. For example, cycloalkane vapor is also detectable due to the same adsorption mechanism (see FIGS. 18A and 18B). Due to the bulkier conformation compared to n-hexane, the saturated vapor of cyclohexane caused larger decrease than n-hexane at a similar vapor concentration.

Figure 9B:
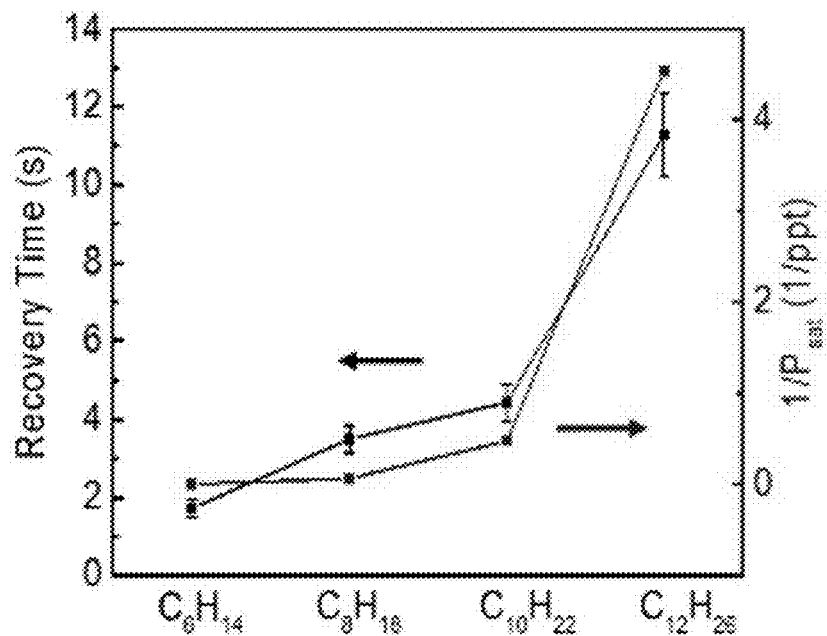
FIG. 9B is a graph of photocurrent recovery times (black dots) for the four alkanes plotted together with the reciprocal values of the corresponding saturated vapor pressure (in part per thousand (ppt) values, blue dots) at room temperature, showing consistency of these two parameters depending on the size of alkanes.

After exposure, the photocurrent also recovered at different rates depending upon the species of alkanes (recovery period). Based on a likely mechanism, the interruption to the photocurrent depends on the alkane molecules adsorbed at the D-A interface. Therefore, the photocurrent gradually recovered to its baseline with the process of alkane molecule desorption. During these processes, the alkane length also controls the photocurrent recovery rates, e.g. with retention times that increase with molecular weight. To quantitatively compare them, different alkane recovery curves were fitted with a single exponential function with good correlation (see FIGS. 19A-19E). Based on the fitting, the recovery time is indexed by the lifetime term, $\tau$. For short alkyl chains, the disassociation rates are faster than those of the longer chains. For hexane, $\tau$ is about 1.6 seconds. With the increasing length of the alkane, $\tau$ increases gradually to over 10 seconds for dodecane. This variation of photocurrent recovery kinetics supports the respective disassociation abilities of the different alkanes at the alkyl interface of ACTC/PTCDI-DD composite. Considering the vaporization process of the alkanes from their pure liquid phase, they disassociate from the homogeneous top layer of the liquid phase, just as the case here that alkanes disassociate from the alkyl surface of ACTC/PTCDI-DD composite. For the vaporization process, when the vapor concentration does not reach the saturated vapor pressure ($P_{sat}$), the disassociation process is dominant. Therefore, the value of $P_{sat}$ could describe the general disassociation ability of molecules from an analogous interface. For example, if the $P_{sat}$ is low, the molecules slowly dissociate from the interface. Herein, the correlation between the two processes can be determined by plotting together the reciprocal values of $P_{sat}$ and $\tau$ for different alkanes to demonstrate the similarity of these two terms (FIG. 9B). It is noted that for the alkane vapors at lower concentrations, the recovery kinetics were maintained even though the amplitudes of the response were much smaller. This indicates that the kinetic characteristics are caused by the thermodynamic nature of alkanes themselves, and could become an important fingerprint for the distinction between the alkanes.

Figure 9C:
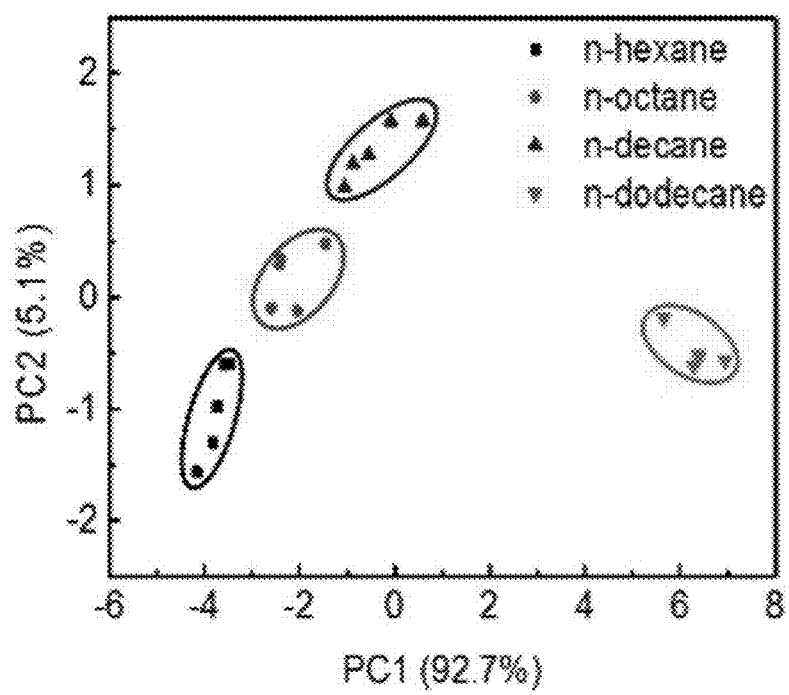
FIG. 9C is a graph of principal component scores for the responses of four alkanes exposures (5 trials for each alkane); the colored circles present the clustering results for the four alkanes.

As discussed above, the kinetics characteristics of the photocurrent responses in both the exposure and recovery periods are quite different for the different sizes of alkanes. They are mainly attributed to their different adsorption and disassociation rates at the interface. Therefore, the kinetic characteristics offer abundant information relating to the different alkanes, which allows the composite sensor to efficiently distinguish a specific alkane among a class of alkanes. To quantitatively identify the differences, principle component analysis (PCA) method was applied to process the photocurrent responses curves for the four alkanes after normalization, as shown in FIG. 9C. For the five trials of each alkane, their principal component scores show a compact clustering among different alkanes and the clusters are separated well. Plus, the amplitude of the response is closely related to the vapor concentration. Therefore, by utilizing both the amplitude and the kinetic characteristics of the signal, the composite sensor is able to determine both the concentration and identify the specific alkane.

FIGS. 20A-20B depict graphs showing a processing method in the principle component analysis (PCA). FIG. 20A depicts each exposure (20 in total) in FIG. 4B replotted together. For each exposure, the data for the first 6 seconds were used for modeling. FIG. 20B depicts data that was re-scaled prior to analysis, i.e., each response curve was centered on its average value and thereafter scaled to a standard deviation of one. Then PCA was performed using the statistics package in Matlab 2014b for the pretreated data in FIG. 20B and the first two components show clear separation between the different alkanes.

Interfacial Morphology and its Impact to Alkane Vapor Detection in the ACTC/PTCDI-DD Composite.

Figure 10A:
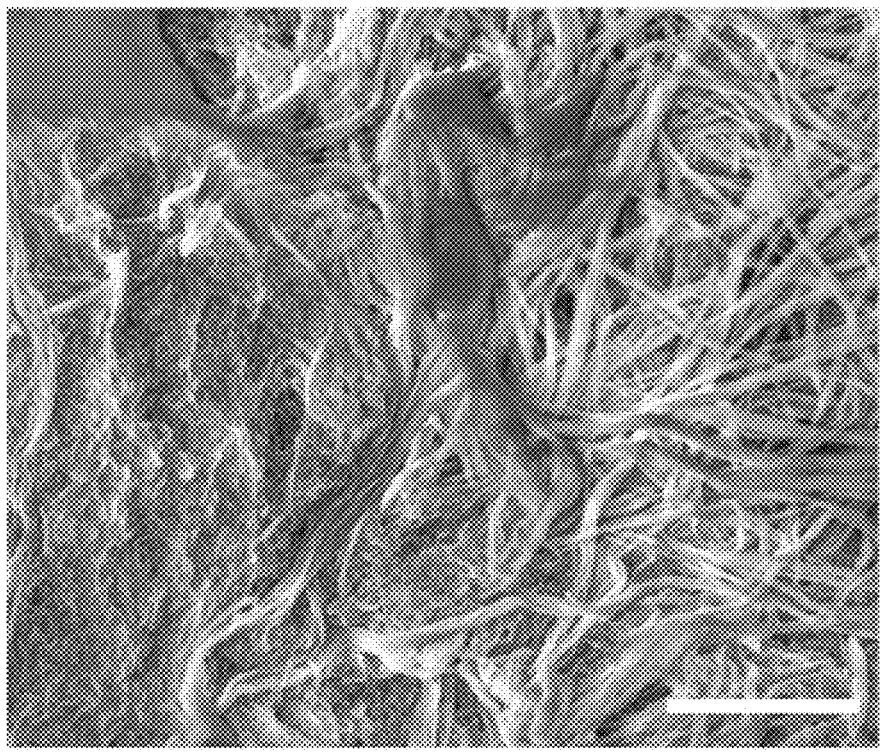
FIG. 10A is a micrograph of a post-mixture of PTCDI-DD nanofibers and ACTC nano fibers.

On the molecular design level, the substitution of long alkyl chains can provide a compatible D-A interface, which plays a valuable role in the ACTC/PTCDI-DD alkane sensor. But that is not a sufficient condition for the desired interface because the alkanes are expected not only to be adsorbed on the surface, but also to affect the D-A distance. Thus, beyond the molecular design, an interface with flexible D-A distance needs to be constructed. To achieve the desired structure, the unique one-step fabrication method was applied to create the nanoporous D-A interface with ultrathin ACTC nanofibers covered on the relatively larger PTCDI fibers, which makes the D-A interface easy to tune. By comparing structures fabricated using other methods, it can be shown that without the particular D-A interface present in the ACTC/PTCDI-DD composite, the sensor performance is absent even with the same molecular composition. In the first control experiment, the PTCDI-DD nanofibers and ACTC nanofibers were prepared separately via a solution-based method. Their concentrated suspensions were mixed and shaken for 4 hours to a visually homogenous state. However, the structure of the post-mixture composite is not uniform on the micrometer scale, as shown in FIG. 10A. The shapes of the PTCDI-DD nanofibers and ACTC nanofibers are not changed after the mixing compared to their pristine structures, and the PTCDI-rich part and ACTC-rich part are segregated by obvious boundaries. Owing to the phase separation, the PCT efficiency is very low for this mixture. The photocurrent is only six times larger than the dark current (FIG. 21A). In the alkane vapor test, the overall amplitudes of photocurrent responses were similar to the ACTC/PTCDI-PE for the short chain alkanes (FIG. 21B). For longer chain alkanes, such as dodecane, the response is even lower and the recovery shows no significant difference from the short chain alkanes. We believe the reason for the poor sensitivity is the lack of sufficient D-A interface.

Figure 10B:
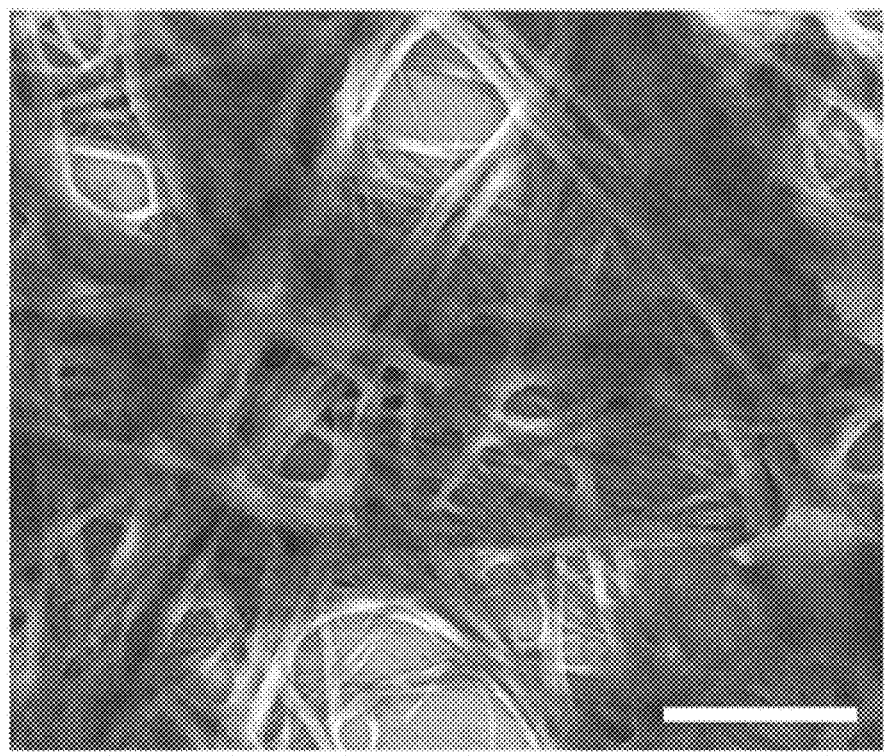
FIG. 10B is a micrograph of PTCDI-DD nanofibers covered by subsequently drop cast ACTC molecules; scale bar=5 µm.

On the other hand, to overcome the phase segregation of donors and acceptors, the second control was prepared by drop casting a molecular solution of ACTC molecules onto PTCDI-DD nanofibers that were already deposited on a substrate. This method was previously used to fabricate highly photoconductive structures with high yield of charge transfer. The morphology of this composite as shown in FIG. 10B, clearly indicates that the PTCDI-DD nanofibers retained their structure after surface coating. The ACTC molecules, after drop casting, form a uniform thin film on the surface of the PTCDI-DD nanofibers. This ACTC drop casting composite shows a photocurrent enhancement of a factor of ca. 700 compared to the dark current, which is significantly larger than the post-mixing composite (FIG. 22A). Therefore, the drop casting method provides effective D-A interface between PTCDI-DD and ACTC molecules. However, the dense coating of ACTC changes the porosity of the PTCDI nanofiber film, likely blocking the small pores and shrinking the larger ones, which should result in decrease of detection sensitivity, particularly for the larger alkanes. This is consistent with the vapor testing results shown in FIG. 22B, where the ACTC drop cast material showed very inhibited sensor responses. For saturated hexane vapor, the relative photocurrent response was less than 4%. With increasing alkane length, the photocurrent response drops dramatically. Again, the kinetic characteristics of the photocurrent responses for different alkanes are lost in this control composite. For most alkane vapors, once the exposure is over, the current recovers at a similarly fast rate.

Figure 10C:
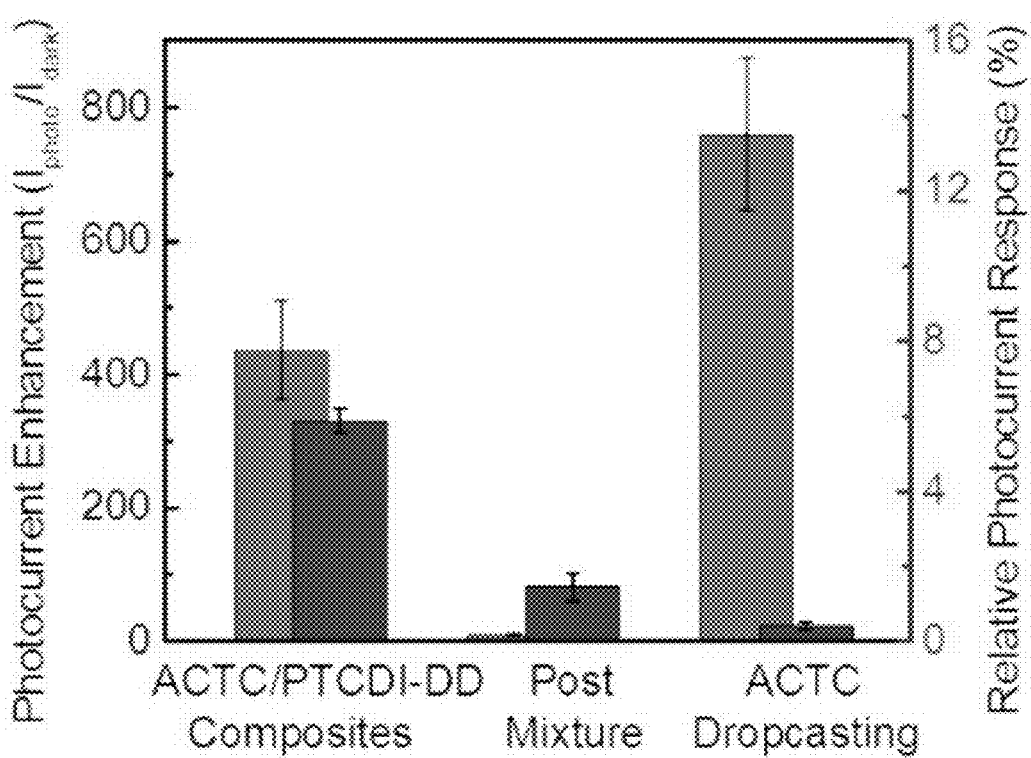
FIG. 10C is a bar graph showing a comparison of the relative photocurrent responses (right) and photocurrent enhancements (left) among the three morphologies of the ACTC/PTCDI-DD composites.

FIG. 10C shows the comparison of the photocurrent enhancements and relative photocurrent responses to dodecane vapor measured over the three ACTC/PTCDI-DD composites, the homogeneous one, the post-mixed one, and the ACTC drop casting one. These two terms do not show a consistent tendency because of their different requirements for the D-A interface. The photocurrent enhancement is primarily determined by the effective D-A interface (regarding both the distance and contact area), while the sensing response relies largely on the adsorption of alkanes at the D-A interface, which in turn depends on the porosity (accessibility) of the D-A composite. The homogeneous ACTC/PTCDI-DD fibril composite demonstrated the largest sensing response, mainly due to the optimal D-A interface, which not only possesses the large area D-A contact (affording high photocurrent), but also provides a uniform bulk D-A heterojunction structure consistent with the porosity formed by the co-assembly of the ACTC and PTCDI-DD nanofibers, thus maximizing the adsorption of alkanes at the D-A interface.

General Selectivity Over Common Solvents.

Figure 11A:
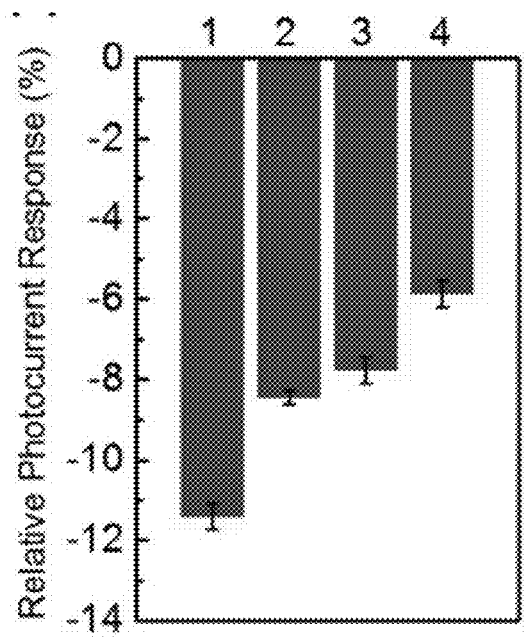
FIGS. 11A and 11B are graphs of general selectivity of an ACTC/PTCDI-DD composite sensor. The bars in each column represents the relative photocurrent positive response of the ACTC/PTCDI-DD composite to the saturated vapors of (FIG. 11A) (1) n-hexane ($C_6H_{14}$), (2) n-octane ($C_8H_{18}$), (3) n-decane ($C_{10}H_{22}$), and (4) n-dodecane ($C_{12}H_{26}$)
Figure 11B:
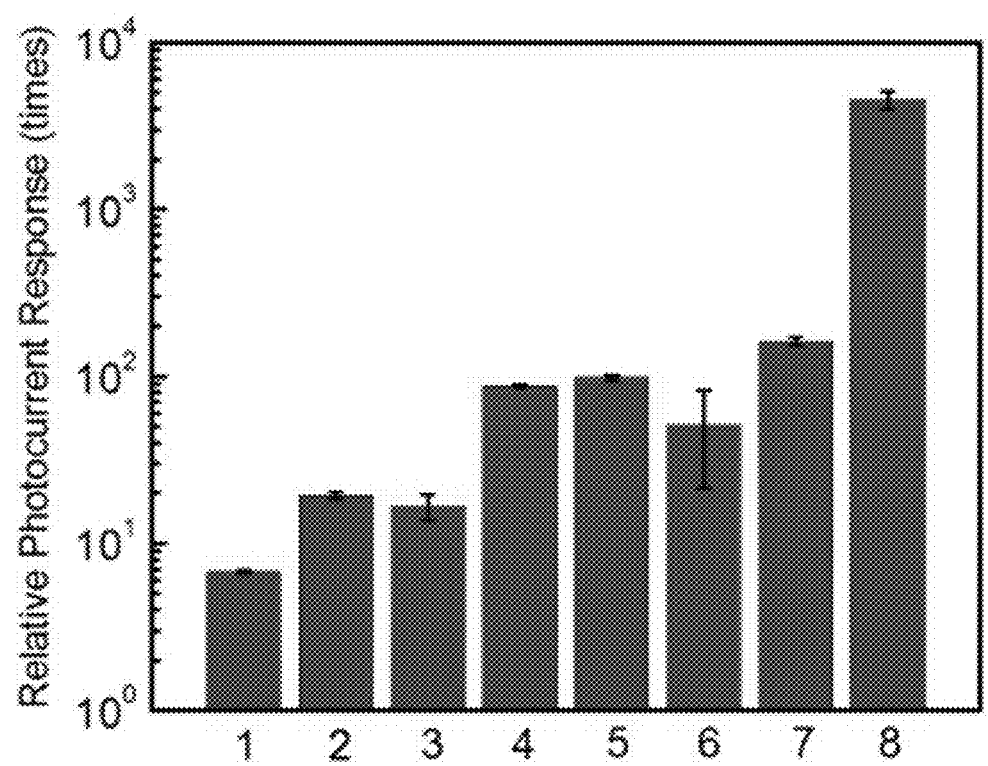

The general selectivity, as another evaluation criterion for sensors, is outstanding for the ACTC/PTCDI-DD composite. The sensing mechanism for alkanes is based on the interruption of the PCT process at the D-A interface in the ACTC/PTCDI-DD composite through adsorption. For the interferents, the adsorption could also happen on the fiber surface, including the D-A interface. However, their effects on the photocurrent are different as shown in FIGS. 23A-23B, where eight interferent vapors were selected to represent common volatile chemical species. During the test, all the eight vapors increased the photocurrent, as opposed to the decrease observed in response to the alkanes. The results are summarized in FIGS. 11A-11B. This divergence demonstrates the outstanding selectivity of ACTC/PTCDI-DD composite for alkane vapors, which arises from the differences in dipole moments and electron donating abilities between the alkanes and interferents. Before the vapor exposure, the forward and backward charge transfer of the D-A composite are in a kinetic equilibrium. With the interfering molecules accumulated at the D-A interface, the charge transfer process might be enhanced by the strong built-in dipole of the interferents, which is also observed in the organic thin film solar cells. With greater charge separation, the photocurrent increases during the exposure of the polar interferents. Additionally, in some chemicals, the dipole structures may include some electron donating groups, such as the amine group in hexylamine. With suitable energy levels, such groups are able to donate electrons to the PTCDI fiber upon light irradiation. With this additional electron source, the PTCD-DD achieves a larger photocurrent, as shown in FIG. 11B, column 8. Among the selected interferents, the hexylamine vapor brings nearly two orders greater response than other interferents. Due to the nonpolar structure and non-electron donating ability of alkanes, their adsorption only enlarges the D-A distance, thus weakening the charge transfer process. Therefore, the difference of dipole moment is likely the origin of the outstanding general selectivity of the ACTC/PTCDI-DD composite.

Detection in the Liquid State.

In all above experiments, the sensors are exposed to the vapors to produce a photocurrent change. However, due to the sensing mechanism, the detection range is not limited to the vapor state. To broaden the application fields and further verify the sensor mechanism, small amounts of alkanes and interferents were dropped onto the surface of the ACTC/PTCDI-DD fiber composite when the photocurrent was being measured (see the responses to alkanes in FIG. 24 and the responses to the interferents in FIGS. 25A-25B). Overall, the results for both alkanes and interferents agree with the trends observed in the vapor exposure experiments, but the amplitudes of photocurrent responses are much larger, owing to the much higher concentrations of analytes at the D-A interface. A few seconds after the initial contact, the short chain alkanes, n-hexane, cyclohexane, and n-octane, evaporated and the photocurrents recovered to the baseline quickly, which demonstrates the robustness of the D-A interface with ACTC and PTCDI-DD. In contrast, the recovery for the larger alkanes took longer due to their higher boiling points (condensed stronger on the surface).

Through molecular and materials structure design, the ACTC/PTCDI-DD nanofiber composite demonstrated outstanding sensitivity and selectivity to alkanes, which results from its porous and compatible D-A interface. By comparing the three composites fabricated from different side-chain substituted PTCDI and ACTC molecules, the ACTC/PTCDI-DD composite showed the most homogeneous D-A interface due to the solvophilic compatibility of ACTC and PTCDI-DD; and such compatibility also contributes to the adsorption of alkanes onto the ACTC/PTCDI-DD interface. As designed, the adsorbed alkanes caused slight swelling within the interface, which was shown by the PCT efficiency changes between the ACTC and PTCDI-DD due to its sensitive dependence in the D-A distance. To realize the tunable charge transfer process, a co-assembly method was developed to fabricate the ACTC/PTCDI-DD nanofiber composite. As shown in previous sections, this composite features large area D-A interface while still maintaining the highly porous structure intrinsic to fibril materials. Combination of these features enhances the diffusion and adsorption of the gas analytes, thus enabling sensitive detection of alkane vapor via monitoring the photocurrent response. Due to the reversible interaction between the alkanes and the D-A interface or CNT junction, the current recovers to the baseline in minute level, which makes the sensor ready for the next detection. The ACTC/PTCDI-DD composite also shows good general selectivity toward alkanes against the common volatile interferents (e.g., solvents), which all display the opposite photocurrent responses. Additionally, the kinetic characteristics of the photocurrent response can be employed to distinguish a specific alkane among the alkane family. In summary, with sophisticated D-A interface design, nanofiber composites can be developed into effective chemiresistive sensor for trace vapor detection of alkanes at room temperature.

Carbon Nanotube Composite Sensors

Consistent with the principles outlined above with respect to FIG. 2, carbon nanotubes were coated with poly-3-hexylthiophene. Single-walled (enriched (6,5) and (7,6) semiconducting) were purchased from Southwest Nano and poly-3-hexylthiophene (P3HT) was purchased from Reike Materials. Both were placed in chloroform with excess P3HT. Sonication was used to create a suspension; where the P3HT coats the CNTs and renders them soluble. Centrifugation is used to remove any CNTs that are not coated. Supernatant is removed and either centrifuged again or deposited onto electrodes to make sensors. Electrodes with 100 microns of separation (gap) were coated with the material by drop casting. Drop casting was repeated until the electrical resistance is in the target range (~100 kOhms).

FIG. 26 is an AFM image of the coated carbon nanotubes. Similar materials were formed with various poly-3-alkylthiophenes including butyl, hexyl, octyl and dodecyl as the alkyl group. Each material was associated with a pair of electrodes and tested for response to hexane (diluted to 8% of saturated vapor concentration). FIG. 27A-B are response curves for each material. Composites with larger alkyl groups tended to respond more strongly to larger alkanes. Similarly, composites with smaller alkyl groups tended to respond more strongly to smaller alkanes consistent with desired selectivity. The sensors were also exposed to three different concentrations of the analytes (2%, 4%, and 8% of the saturated vapor). FIG. 27C-E illustrate the selectivity of each sensor to different analytes. Mathematical models can be readily used to distinguish signals and categorize responses. FIG. 27F is a graph of principal component analysis results of the sensor responses. As can be seen, hexane and octane are readily distinguishable. Further, dodecane and decane are distinct from octane and hexane while occupying the same space as one another. Thus, longer alkanes are distinguishable from shorter alkanes.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A nanofiber composite sensor for detecting alkanes comprising a network of contacting nanofibers having multiple contact points each forming an interfiber interface of interdigitated alkyl chains, wherein the alkanes are adsorbed at the interfiber interface to increase an interfiber distance between first and second nanofibers and decrease charge transfer efficiency.

2. The composite sensor of claim 1, wherein the alkanes are in vapor or liquid phase.

3. The composite sensor of claim 1, wherein the interdigitated alkyl chains comprise at least one hydrophobic branched or straight alkyl chain ($C_nH_{2n+1}$ or $O-C_nH_{2n+1}$), wherein n=1-30.

4. The composite sensor of claim 1, wherein the first nanofiber is a donor nanofiber formed of a donor molecule and the second nanofiber is an acceptor nanofiber formed of an acceptor molecule with a photoinduced charge transfer process between them to provide a homogeneous donor-acceptor interface at the interfiber interface.

5. The composite sensor of claim 4, wherein the donor nanofiber is formed from a dodecyl-substituted arylene-ethynylene tetracycle (ACTC).

6. The composite sensor of claim 4, wherein the donor nanofiber comprises oligothiophene, polythiophene, oligofluorene, polyfluoene, oligocarbazole, polycarbazole, arylene-ethynylene tetracycline, dithiophene, [1]benzothieno[3,2-b][1]benzothiophene, anthracene, tetracene, pentacene, pyrene, perylene, oligo(p-phenylene vinylene) (OPV), poly(p-phenylene vinylene) (PPV), or combinations thereof.

7. The composite sensor of claim 4, wherein the donor nanofiber is formed of:

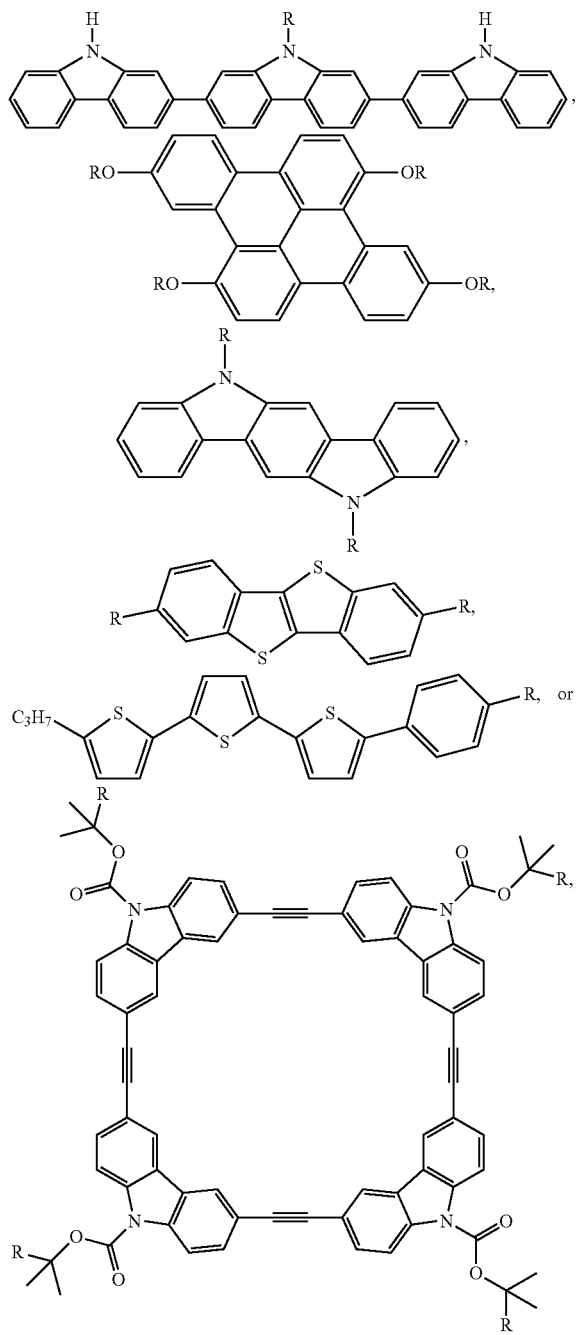

wherein R=($C_nH_{2n+1}$ or O—$C_nH_{2n+1}$) and n=1-30.

8. The composite sensor of claim 4, wherein the acceptor nanofiber comprises 3,4,9,10-perylenedicarboximide (PTCDI), naphthalene diimide (NDI), pyrrolo[3,4-c]pyrrole-1,4-dione (PPO), or combinations thereof.

9. The composite sensor of claim 1, wherein the first and second nanofibers comprise single-walled or multiple-wall carbon nanotube fibers non-covalently bonded with a carbon nanotube dispersant including the interdigitated alkyl chains, such that the first nanofibers and second nanofibers are compositionally homogeneous.

10. The composite sensor of claim 9, wherein the carbon nanotube dispersant comprises a monomer, oligomer, or polymer that contains at least one of thiophene, pyrene, carbazole, fluorene, phenylene, arylene, vinylene, aniline, imine, azole, pyrrole, porphyrin, phthalocyanine, acenes, DNA, naphthalene, anthracene, perylene, styrene, or a combination thereof.

11. The composite sensor of claim 10, wherein the network is formed by casting a solution of the carbon nanotube dispersant with the carbon nanotube dispersed therein on a substrate and forming a uniform thin film on the substrate.

12. The composite sensor of claim 1, further comprising a pair of electrodes electrically associated with the network such that an electrical conductivity measurement occurs across the network.

13. The composite sensor of claim 1, wherein the sensing material is fabricated into chemiresistors such that the alkane vapor is detected via monitoring the electrical current change.

14. A method of detecting alkanes, comprising:
a) exposing a network of contacting nanofibers having multiple contact points each forming an interfiber interface of interdigitated alkyl chains to a suspected target compound source;
b) measuring an electrical response of the network of nanofibers caused by the alkanes adsorbing at the interfiber interface and increasing an interfiber distance between first and second nanofibers so as to decrease the charge transfer efficiency; and
c) displaying a detection metric based on the electrical response.

15. The method of claim 14, wherein a temperature of detection is 32-167° F. (0-75° C.).

16. The method of claim 14, wherein the sensor is reusable.

17. The method of claim 14, wherein a limit of detection of the method is below a 1% saturated vapor pressure of the analyte.

18. The method of claim 14, wherein the electrical response of the network of nanofibers is discernible between alkanes of different lengths.

19. The method of claim 14, wherein the electrical response detects the alkanes in less than 3 seconds and provides the detection metric within 6 seconds.

20. The method of claim 14, wherein the detection metric is selected from the group consisting of a change in conductivity, change in resistance, change in voltage, change in current, and combinations thereof.

21. The method of claim 14, wherein the first nanofiber is a donor nanofiber and the second nanofiber is an acceptor nanofiber.

22. The method of claim 14, wherein the first and second nanofibers are single-walled or multiple-wall carbon nanotube fibers non-covalently bonded with a carbon nanotube dispersant including the interdigitated alkyl chains.

* * * * *